US012766197B2

(12) United States Patent
Verovskaya et al.

(10) Patent No.: US 12,766,197 B2
(45) Date of Patent: Oct. 20, 2026

(54) LIPID COMPOSITIONS FOR IN VIVO DELIVERY

(71) Applicant: LIFE TECHNOLOGIES CORPORATION, Carlsbad, CA (US)

(72) Inventors: Evgenia Verovskaya, Oceanside, CA (US); Joel Jessee, Stuart, FL (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 428 days.

(21) Appl. No.: 18/344,694

(22) Filed: Jun. 29, 2023

(65) Prior Publication Data

US 2024/0000966 A1 Jan. 4, 2024

Related U.S. Application Data

(60) Provisional application No. 63/510,733, filed on Jun. 28, 2023, provisional application No. 63/357,584, filed on Jun. 30, 2022.

(51) Int. Cl.

| | |
|---|---|
| ***A61K 47/69*** | (2017.01) |
| ***A61K 9/1271*** | (2025.01) |
| ***A61K 9/1277*** | (2025.01) |
| ***A61K 39/145*** | (2006.01) |
| *A61K 39/00* | (2006.01) |

(52) U.S. Cl.

CPC ........ *A61K 47/6911* (2017.08); *A61K 9/1271* (2013.01); *A61K 9/1277* (2013.01); *A61K 39/145* (2013.01); *A61K 2039/53* (2013.01); *A61K 2039/55555* (2013.01); *A61K 2039/575* (2013.01)

(58) Field of Classification Search

None

See application file for complete search history.

(56) References Cited

U.S. PATENT DOCUMENTS

2011/0165223 A1* 7/2011 Sgouros ............... A61K 9/0019 424/277.1

2011/0200624 A1* 8/2011 Jessee ............... A61K 47/6835 435/325

2016/0081944 A1* 3/2016 Lee ........................ C12N 15/88 424/491

FOREIGN PATENT DOCUMENTS

WO WO-2020077007 A1 * 4/2020 .............. A61P 25/16

WO WO-2020262150 A1 * 12/2020 ............. A61K 47/28

OTHER PUBLICATIONS

Aqeel Ahmad, Javed Masood Khan, and Shafiul Haque. "Strategies in the design of endosomolytic agents for facilitating endosomal escape in nanoparticles." Biochimie, vol. 160, 2019, pp. 61-75. (Year: 2019).*

Linde Schoenmaker et al. "mRNA-lipid nanoparticle COVID-19 vaccines: Structure and stability." International Journal of Pharmaceutics 601 (2021) 120586, pp. 1-13. (Year: 2021).*

(Continued)

*Primary Examiner* — Isaac Shomer

(57) ABSTRACT

Provided herein, are compositions, methods and kits for inducing an immune response in a subject. In aspects, a lipid composition is described, which includes at least one ionizable lipid comprising a charge (N), at least one peptide, and a nucleic acid molecule comprising a charge (P). In aspects, methods are provided for delivery of a payload to an immune cell using a lipid composition comprising at least one ionizable lipid, at least one endosomal release peptide, and a payload.

10 Claims, 28 Drawing Sheets

Specification includes a Sequence Listing.

(56) References Cited

OTHER PUBLICATIONS

English Translation of WO2020262150A1. Obtained from https://patents.google.com/patent/WO2020262150A1/en?oq=WO+2020262150+ on Sep. 25, 2025. Originally published in Japanese on Dec. 30, 2020, 14 printed pages. (Year: 2020).*

Aqeel Ahmad, Javed Masood Khan, and Shafiul Haque. "Strategies in the design of endosomolytic agents for facilitating endosomal escape in nanoparticles." Biochimie 160 (2019), pp. 61-75. (Year: 2019).*

* cited by examiner

| Target | Antigen | Fluorophone |
|---|---|---|
| Pan B Cells | B220 | APC-Cy7 |
| Dendritic Cells | MHCII | SB436 |
| Hematopoietic Cells | CD45.2 | FITC |
| Dendritic Cells | CD11c | APC |
| T Cells | CD3 | PE-Cy7 |
| T Cells | CD4 | SB600 |
| T Cells | CD8 | SB702 |
| Dead Cells | FVD | eFluor506 |

Lipid-mRNA complexation :
H10N8 Influenza Virus Hemagglutinin mRNA Formulated LP11 lipids and LP12 lipids were Injected.

Intramuscular injection (each quadriceps)

Intravenous injection (lateral tail vein)

| Group | Injection | # of animal | Route | Sample # |
|---|---|---|---|---|
| 1 | Saline | 5 | IM | 1~5 |
| 2 | LP12:HA mRNA 0.2 ug | 5 | IM | 6~10 |
| 3 | LP12:HA mRNA 1 ug | 5 | IM | 11~15 |
| 4 | LP12:HA mRNA 5 ug | 5 | IM | 16~20 |
| 5 | LP11:HA mRNA 0.2 ug | 5 | IM | 21~25 |
| 6 | LP11:HA mRNA 1 ug | 5 | IM | 26~30 |
| 7 | LP11:HA mRNA 5 ug | 5 | IM | 31~35 |
| 8 | Saline | 5 | IV | 36~40 |
| 9 | LP12:HA mRNA 10 ug | 5 | IV | 41~45 |
| 10 | LP12:HA mRNA 20 ug | 5 | IV | 46~50 |
| 11 | LP11:HA mRNA 10 ug | 5 | IV | 51~55 |
| 12 | LP11:HA mRNA 20 ug | 5 | IV | 56~60 |
| | | Total 60 | | |

FIG. 13

*PMA+ ionomycin and ConA were used for positive stimuli for T cell activation

LIPID COMPOSITIONS FOR IN VIVO DELIVERY

RELATED APPLICATIONS

This application claims the benefit of priority under 35 U.S.C. § 119 (e) to U.S. Provisional Application No. 63/510,733 filed on Jun. 28, 2023, and to U.S. Provisional Application No. 63/357,584 filed on Jun. 30, 2022, the contents of which are hereby expressly incorporated herein by reference in their entirety as though fully set forth herein.

SEQUENCE LISTING

The instant application contains a Sequence Listing which has been submitted electronically in ST.26 XML format and is hereby incorporated by reference in its entirety. Said XML document, created on Jun. 28, 2023, is named TP109375WO1_SL.XML and is 34,000 bytes in size.

TECHNICAL FIELD

The present invention is in the field of lipid compositions and formulations suitable for the delivery of one or more biologically active agents to a cell (e.g., an immune cell) and methods and kits for using the same.

BACKGROUND

Designing lipid compositions and formulations capable of targeting payloads to specific organs, tissues, or cell types without the use of canonical biomolecular targeting techniques remains a challenge. Improved compositions and methods for delivering biologically active payloads to specific tissues and/or cell types, in particular to immune system tissues and cells, are greatly to be desired. Provided herein are compositions and methods which address this and other needs in the art.

BRIEF SUMMARY

In aspects, provided herein are methods for delivering a payload to a spleen cell in a subject, including: (i) providing a lipid complex comprising at least one ionizable lipid, at least one peptide where the peptide comprises LLELLESL (SEQ ID NO: 1), and at least one payload molecule; and (ii) administering the lipid complex to a subject. In some embodiments, the lipid complex further comprises at least one neutral lipid.

In some embodiments, the peptide has at least 80% sequence identity to GLFEALLELLESLWELLLEA (SEQ ID NO: 6). In some embodiments, the peptide comprises a sequence selected from the group consisting of SEQ ID NOs: 2-24. In other embodiments, the lipid complex further includes a second peptide which comprises at least one of SEQ ID NO: 25 and/or SEQ ID NO: 26.

In some embodiments, the peptide is at a concentration from about 0.001 to about 0.5 mg/mL, or from about 0.05 mg/mL to about 0.5 mg/mL. In some embodiments, the peptide is at a concentration from about 0.001 to about 0.5 mg/mL. In some embodiments, the peptide is at a concentration from about 0.05 mg/mL to about 0.5 mg/mL. In some embodiments, the peptide is at a concentration of about 0.001 mg/mL. In other embodiments, the peptide is at a concentration of about 0.05 mg/mL. In other embodiments, the peptide is at a concentration of about 0.5 mg/mL.

In certain embodiments, the payload is a nucleic acid. In some embodiments, the at least one ionizable lipid comprises a charge (N), the payload nucleic acid comprises a charge (P), and the lipid complex comprises an N/P ratio from 0.01 to 0.2, or from 0.05 to 0.5, or from 0.1 to 1.0, or from 0.5 to 2.0, or from 1.0 to 5.0.

In some embodiments, the N/P ratio is from about 0.01 to about 0.2. In some embodiments, the N/P ratio is from about 0.05 to about 0.5. In some embodiments, the N/P ratio is from about 0.1 to about 1.0. In some embodiments, the N/P ratio is from about 0.5 to about 2.0. In some embodiments, the N/P ratio is from about 1.0 to about 5.0. In some embodiments, the N/P ratio is less than about 0.1. In some embodiments, the N/P ratio is about 0.1. In some embodiments, the N/P ratio is about 0.2. In some embodiments, the N/P ratio is about 0.5. In some embodiments, the N/P ratio is about 1.0. In some embodiments, the N/P ratio is about 2.0.

In some embodiments, the payload comprises an RNA molecule. In some embodiments, the RNA molecule includes mRNA, siRNA, shRNA, miRNA, self-replicating RNA (srRNA), self-amplifying RNA, stRNA, sgRNA, crRNA, tracrRNA, or combinations thereof. In some embodiments, the RNA molecule includes more than one mRNA molecule. In some embodiments, the RNA molecule includes at least two mRNA molecules. In some embodiments, the RNA molecule includes an sgRNA molecule and an mRNA molecule. In some embodiments, the RNA molecule includes an sgRNA molecule.

In other embodiments, the payload further includes a protein.

In some embodiments, the nucleic acid payload encodes an immunogen. In some embodiments, the nucleic acid payload encodes for hemagglutinin (HA) or for ovalbumin.

In some embodiments, the ionizable lipid includes a lipid according to Formula (I), Formula (II), Formula (III), Formula (IV), or Formula (V), or combinations thereof. In some embodiments, the ionizable lipid includes at least one lipid according to Formula (I). In some embodiments, the ionizable lipid includes at least one lipid according to Formula (II). In some embodiments, the ionizable lipid includes at least one lipid according to Formula (III). In some embodiments, the ionizable lipid includes at least one lipid according to Formula (IV). In some embodiments, the ionizable lipid includes at least one lipid according to Formula (V).

In some embodiments, the ionizable lipid includes a lipid according to Formula (IA) or Formula (IB), or combinations thereof. In some embodiments, the ionizable lipid includes a lipid according to Formula (IA). In some embodiments, the ionizable lipid includes a lipid according to Formula (IB). In some embodiments, the at least one ionizable lipid includes a lipid according to Formula (IA) and an ionizable lipid according to Formula (IB).

In some embodiments, the ionizable lipid includes a lipid according to Formula (IIA), Formula (IIB), or Formula (IIC), or combinations thereof. In some embodiments, the ionizable lipid includes a lipid according to Formula (IIA). In some embodiments, the ionizable lipid includes a lipid according to Formula (IIB). In some embodiments, the ionizable lipid includes a lipid according to Formula (IIC).

In some embodiments, the neutral lipid includes cholesterol, sterol, dioleoylphosphatidylethanolamine (DOPE), diphytanoylphosphatidylethanolamine (DPhPE), Lyso-PE (1-acyl-2-hydroxy-sn-glycero-3-phosphoethanolamine), Lyso-PC (1-acyl-3-hydroxy-sn-glycero-3-phosphocholine), distearoylphosphatidylcholine (DSPC), dioleoylphosphatidylcholine (DOPC), dipalmitoylphosphatidylcholine (DPPC), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanol amine (SOPE), and 1,2-dioleoyl-sn-glycero-3-phophoethanolamine (trans DOPE), or combinations thereof.

In other embodiments, the lipid complex includes liposomes. In some embodiments, the lipid complex includes lipid nanoparticles. In some embodiments, the lipid complex includes a lipid nanoparticle population, wherein the nanoparticle has a diameter from about 20 nm to about 1 μm. In some embodiments, the nanoparticle has a diameter from about 10 nm to about 900 nm. In some embodiments, the nanoparticle has a diameter from about 20 nm to about 800 nm. In some embodiments, the nanoparticle has a diameter from about 20 nm to about 700 nm. In some embodiments, the nanoparticle has a diameter from about 20 nm to about 600 nm. In some embodiments, the nanoparticle has a diameter from about 20 nm to about 500 nm. In some embodiments, the nanoparticle has a diameter from about 20 nm to about 400 nm. In some embodiments, the nanoparticle has a diameter from about 20 nm to about 300 nm. In some embodiments, the nanoparticle has a diameter from about 20 nm to about 200 nm. In some embodiments, the nanoparticle has a diameter from about 20 nm to about 100 nm. In some embodiments, the nanoparticle has a diameter from about 20 nm to about 50 nm.

In embodiments, the administering includes systemic administration or local administration. In some embodiments, the local administration comprises intramuscular administration or subcutaneous administration. In embodiments, the administering comprises intravenous administration. In embodiments, the administering comprises administration to the brain, spinal cord, eye or lymph node of a subject.

In some embodiments, the subject includes a mammalian subject. In some embodiments, the subject includes a human.

In some embodiments, the payload is delivered to a dendritic cell of the spleen. In some embodiments, the lipid complex targets an spleen cell of the subject about 1.2×, 1.3×, 1.4×, 1.5×, 1.6×, 1.7×, 1.8×, 1.9×, 2.0×, 2.5× or more compared to targeting with administration of a lipid complex comprising the ionizable lipid and the payload without the peptide.

Provided herein are methods for expressing a protein in spleen tissue in a subject, including administering the lipid complex described herein to the subject via systemic administration.

In aspects, provided herein are compositions for delivery of a payload to a spleen cell. Provided herein is a composition having at least one ionizable lipid, and at least one peptide, wherein the peptide has comprises LLELLESL (SEQ ID NO: 1) and is present at a concentration less than 1.0 mg/ml, and at least one payload molecule. In other embodiments, the peptide is at a concentration of about 1.0 mg/mL. In other embodiments, the peptide is at a concentration of about 0.05 mg/mL.

Also provided herein are compositions including at least one ionizable lipid having a charge (N), at least one peptide, wherein the peptide, wherein the peptide has comprises LLELLESL (SEQ ID NO: 1), and at least one payload comprising a nucleic acid having a charge (P). The compositions have an N/P ratio from 0.01 to 0.2, or from 0.05 to 0.5, or from 0.1 to 1.0, or from 0.5 to 2.0, or from 1.0 to 5.0. In some embodiments, the N/P ratio is the ratio of positively charged groups (including amine (N) groups) to negatively charged groups including phosphate (P) and peptide groups.

Also provided herein is a composition including: at least one ionizable lipid having a charge (N), at least one endosomal release peptide, and at least one payload comprising a nucleic acid having a charge (P), wherein the composition has an N/P ratio of about 0.01 to about 0.5.

In some embodiments, the composition further comprises at least one neutral lipid. In some embodiments of the composition, the peptide has at least 80% sequence identity to GLFEALLELLESLWELLLEA (SEQ ID NO: 6). In some embodiments, the peptide comprises a sequence selected from the group consisting of SEQ ID NOs: 2-24. In other embodiments, the composition further includes a second peptide which comprises at least one of SEQ ID NO: 25 and/or SEQ ID NO: 26.

In some embodiments, the peptide is at a concentration from about 0.001 to about 0.5 mg/mL, or from about 0.05 mg/mL to about 0.5 mg/mL. In some embodiments, the peptide is at a concentration from about 0.001 to about 0.5 mg/mL. In some embodiments, the peptide is at a concentration from about 0.05 mg/mL to about 0.5 mg/mL. In some embodiments, the peptide is at a concentration of about 0.001 mg/mL. In other embodiments, the peptide is at a concentration of about 0.05 mg/mL. In other embodiments, the peptide is at a concentration of about 0.5 mg/mL.

In some embodiments, the N/P ratio is from about 0.01 to about 0.2. In some embodiments, the N/P ratio is from about 0.05 to about 0.5. In some embodiments, the N/P ratio is from about 0.1 to about 1.0. In some embodiments, the N/P ratio is from about 0.5 to about 2.0. In some embodiments, the N/P ratio is from about 1.0 to about 5.0. In some embodiments, the N/P ratio is less than about 0.1. In some embodiments, the N/P ratio is about 0.1. In some embodiments, the N/P ratio is about 0.2. In some embodiments, the N/P ratio is about 0.5. In some embodiments, the N/P ratio is about 1.0. In some embodiments, the N/P ratio is about 2.0.

In some embodiments, the payload comprises an RNA molecule. In some embodiments, the RNA molecule includes mRNA, siRNA, shRNA, miRNA, self-replicating RNA (srRNA), self-amplifying RNA, stRNA, sgRNA, crRNA, tracrRNA, or combinations thereof. In some embodiments, the RNA molecule includes more than one mRNA molecule. In some embodiments, the RNA molecule includes at least two mRNA molecules. In some embodiments, the RNA molecule includes an sgRNA molecule and an mRNA molecule. In some embodiments, the RNA molecule includes an sgRNA molecule.

In other embodiments, the payload further includes a protein.

In some embodiments, the nucleic acid payload encodes an immunogen. In some embodiments, the nucleic acid payload encodes for hemagglutinin (HA) or for ovalbumin.

In some embodiments, the ionizable lipid includes a lipid according to Formula (I), Formula (II), Formula (III), Formula (IV), or Formula (V), or combinations thereof. In some embodiments, the ionizable lipid includes at least one lipid according to Formula (I). In some embodiments, the ionizable lipid includes at least one lipid according to Formula (II). In some embodiments, the ionizable lipid includes at least one lipid according to Formula (III). In some embodiments, the ionizable lipid includes at least one lipid according to Formula (IV). In some embodiments, the ionizable lipid includes at least one lipid according to Formula (V).

In some embodiments, the ionizable lipid includes a lipid according to Formula (IA) or Formula (IB), or combinations thereof. In some embodiments, the ionizable lipid includes a lipid according to Formula (IA). In some embodiments, the ionizable lipid includes a lipid according to Formula (IB). In some embodiments, the at least one ionizable lipid includes a lipid according to Formula (IA) and an ionizable lipid according to Formula (IB).

In some embodiments, the ionizable lipid includes a lipid according to Formula (IIA), Formula (IIB), or Formula (IIC), or combinations thereof. In some embodiments, the ionizable lipid includes a lipid according to Formula (IIA). In some embodiments, the ionizable lipid includes a lipid according to Formula (IIB). In some embodiments, the ionizable lipid includes a lipid according to Formula (IIC).

In some embodiments, the neutral lipid includes cholesterol, sterol, dioleoylphosphatidylethanolamine (DOPE), diphytanoylphosphatidylethanolamine (DPhPE), Lyso-PE (1-acyl-2-hydroxy-sn-glycero-3-phosphoethanolamine), Lyso-PC (1-acyl-3-hydroxy-sn-glycero-3-phosphocholine), distearoylphosphatidylcholine (DSPC), dioleoylphosphatidylcholine (DOPC), dipalmitoylphosphatidylcholine (DPPC), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanol amine (SOPE), and 1,2-dioleoyl-sn-glycero-3-phophoethanolamine (trans DOPE), or combinations thereof.

In other embodiments, the composition includes liposomes. In some embodiments, the composition includes lipid nanoparticles. In some embodiments, the composition includes a lipid nanoparticle population, wherein the nanoparticle has a diameter from about 20 nm to about 1 μm. In some embodiments, the nanoparticle has a diameter from about 10 nm to about 900 nm. In some embodiments, the nanoparticle has a diameter from about 20 nm to about 800 nm. In some embodiments, the nanoparticle has a diameter from about 20 nm to about 700 nm. In some embodiments, the nanoparticle has a diameter from about 20 nm to about 600 nm. In some embodiments, the nanoparticle has a diameter from about 20 nm to about 500 nm. In some embodiments, the nanoparticle has a diameter from about 20 nm to about 400 nm. In some embodiments, the nanoparticle has a diameter from about 20 nm to about 300 nm. In some embodiments, the nanoparticle has a diameter from about 20 nm to about 200 nm. In some embodiments, the nanoparticle has a diameter from about 20 nm to about 100 nm. In some embodiments, the nanoparticle has a diameter from about 20 nm to about 50 nm.

In some embodiments, the composition is for administration to a subject via intramuscular administration, subcutaneous administration, intravitreal administration, administration to the brain, or administration to the spinal cord.

In embodiments, provided herein are methods of inducing an immune response in a subject including: administering to the subject the compositions described herein wherein the payload is an immunogen or encodes for an immunogen. In embodiments, the administering includes systemic administration or local administration, wherein the local administration comprises intramuscular administration or subcutaneous administration. In embodiments, the administering comprises intravenous administration. In embodiments, the administering comprises administration to the brain, spinal cord, eye or lymph node of a subject. In some embodiments, the subject includes a mammalian subject. In some embodiments, the subject includes a human.

In some embodiments, provided herein are methods for delivering a payload to an immune cell of a subject, where the method includes administering any of the compositions described herein to the subject via intravenous administration or via intramuscular administration.

In some embodiments, provided herein are methods for targeting a payload to an immune cell of a subject, the method including administering the compositions described herein to the subject. In embodiments, the immune cell includes T cell, B cell, dendritic cell (DC), T helper cell, cytotoxic T cell (CTL), natural killer cell (NK), macrophage, or combinations thereof. In other embodiments; the immune cell includes a spleen immune cell. In some embodiments, the immune cell includes a spleen dendritic cell.

In some embodiments, the composition targets an immune cell of the subject about 1.2×, 1.3×, 1.4×, 1.5×, 1.6×, 1.7×, 1.8×, 1.9×, 2.0×, 2.5× or more compared to targeting with administration of a composition comprising the ionizable lipid and the payload without the peptide.

In aspects, provided herein is a method for preparing a population of lipid formulations containing a payload molecule, including: (a) mixing a payload molecule with a peptide in an aqueous solution, wherein the peptide comprises LLELLESL (SEQ ID NO: 1); (b) injecting a lipid solution comprising an ionizable lipid into the aqueous solution, wherein the injecting comprises extrusion, in-line mixing, microfluidic mixing, evaporation, or vortexing; and (c) producing the population of lipid formulations complexed with the payload molecule.

Also provided herein is a method for preparing a population of lipid formulations containing a payload molecule, including: (a) contacting a peptide comprising LLELLESL (SEQ ID NO: 1) with a lipid phase, wherein the lipid phase comprises an ionizable lipid, (b) contacting the components of step (a) with a payload in an aqueous solution; (c) mixing the components of step (b) by extrusion, in-line mixing, microfluidic mixing, evaporation, or vortexing; and (d) producing the population of lipid formulations complexed with the payload molecule.

In some embodiments, the lipid solution of (b) or the lipid phase of (a) further comprises at least one neutral lipid. In some embodiments, the peptide comprises at least 80% sequence identity to GLFEALLELLESLWELLLEA (SEQ ID NO: 6). In some embodiments, the payload molecule is a nucleic acid.

In other aspects, provided herein is a kit including a composition having at least one ionizable lipid and at least one peptide where the peptide comprises LLELLESL (SEQ ID NO: 1). In some embodiments, the kit further includes at least one neutral lipid. In some embodiments, the ionizable lipid and neutral lipid are in a separate container from the peptide. In some embodiments, the ionizable lipid and neutral lipid are in the same container as the peptide.

Other aspects of the invention are disclosed infra.

DESCRIPTION OF THE DRAWINGS

FIG. 1A depicts results with different ionizable lipid formulations containing peptide. FIGS. 1B and 1C depict results of formulations with and without peptide.

FIG. 4A is a graph showing results from formulations varying in N/P ratio from 4.0 to 0.125. The intensity of bioluminescence in the region of interest (ROI) used to calculate total flux (photons/second). FIG. 4B are representative bioluminescence images showing the tissue specific delivery of the formulations with N/P 2 to the spleen of a mouse and not to the liver or lung. Scale bar is radiance (p/sec/$cm^2$/sr).

FIG. 8A are representative in vivo bioluminescence images. Scale bar is radiance (p/sec/$cm^2$/sr). FIG. 8B is a graph depicting the intensity of bioluminescence in the region of interest (ROI) used to calculate total flux (photons/second).

FIG. 10A depicts representative fluorescent images of HEK293 cells at different time points after transfection (Red: Cy5 mRNA, blue: DAPI nucleus; scale bars show 10 μm.) In grayscale, the red is the lighter signal and the blue is the darker signal. FIG. 10B is a graph depicting quantitation of cellular uptake over time following transfection.

FIG. 14A is a graph showing the response via intramuscular (IM) delivery of the indicated mRNA doses at 0.01 mg/kg, 0.05 mg/kg, or 0.25 mg/kg. FIG. 14B is a graph showing the response via intravenous (IV) delivery of the indicated mRNA doses at 0.5 mg/kg or 1 mg/kg.

FIG. 15A is an exemplary image showing and ELISPOT assay. FIG. 15B is a graph showing IFN-gamma secretion in response to HA peptide stimulation from splenocytes after intramuscular delivery. FIG. 15C is a graph showing IFN-gamma secretion in response to HA peptide stimulation from splenocytes after intravenous delivery.

DETAILED DESCRIPTION

Figure 1A:
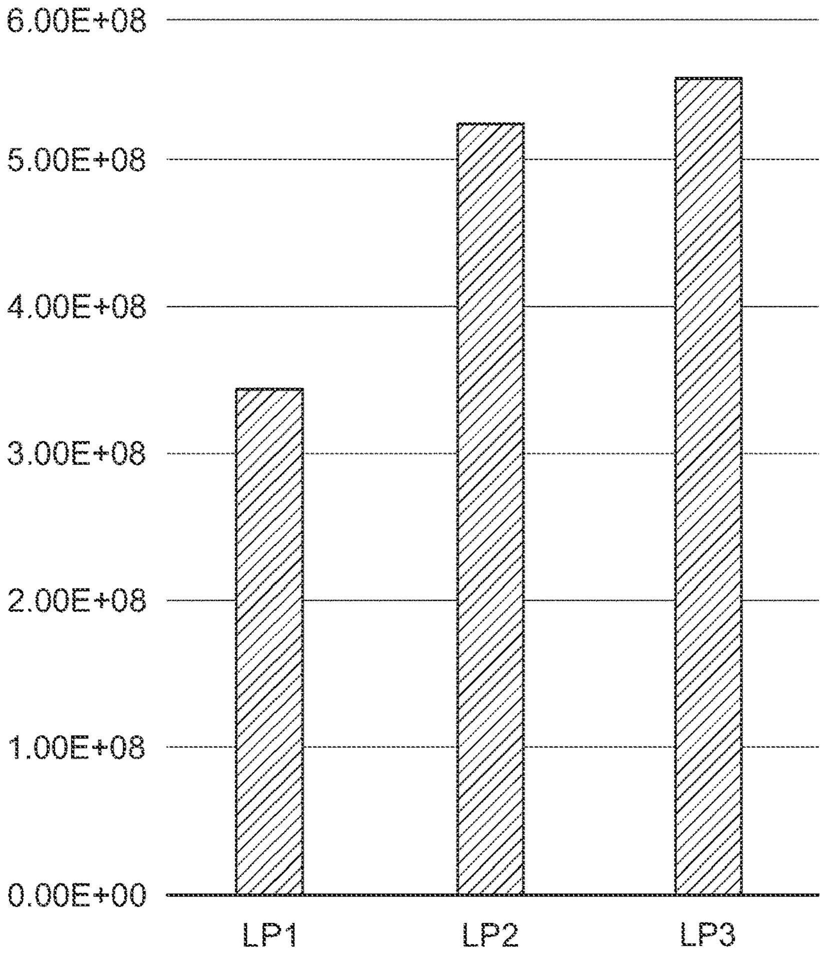
FIGS. 1A-1C are graphs depicting in vivo luciferase flux localized to spleens 4 hours after intravenous administration of lipid-peptide formulations.

We have developed compositions particularly effective for in vivo delivery of payload molecules to specific tissues and/or cell types, in particular to immune system tissues and cells. The compositions include at least one ionizable lipid, an endosomal release peptide and a payload, and provide effective and efficient delivery of the payload specifically to the spleen following intravenous administration, particularly to dendritic cells of the spleen. Following local administration (e.g., intramuscular injection), the compositions provide effective and efficient delivery of the payload specifically to the injection site tissue, and to regional immune cells. For example, antigen-specific humoral and cellular immune responses were obtained following systemic or local administration of antigen-encoding mRNA complexed with the provided formulations.

In a therapeutic application, it is important to achieve the desired biological endpoint with the least amount of formulation administered for example to lessen the chance, or lower the level, of associated toxicities and/or off-target effects. As demonstrated herein, use of the peptide combined with the ionizable lipid in the provided composition results in effective and efficient delivery/uptake of the payload nucleic acids, even with the low levels of lipid and/or nucleic acid in the compositions. This improved efficiency allows for administration of less of a formulation (for example, lower mRNA and/or lipid levels) to achieve the therapeutic effect, for example, a specific immune response.

Exemplary payloads for delivery to immune system tissues and cells via the provided lipid complex compositions include nucleic acid molecules, protein molecules and/or other bioactive agents. In some embodiments, the payload for delivery to an immune cell is a therapeutic agent or a diagnostic agent. In some embodiments, the lipid complex compositions further include at least one neutral lipid.

Provided herein, are compositions, methods and kits for inducing an immune response in a subject. In aspects, a lipid composition is described, which includes at least one ionizable lipid comprising a charge (N), at least one peptide, wherein the peptide comprises the sequence LLELLESL (SEQ ID NO:1), and a nucleic acid molecule comprising a charge (P), wherein the composition comprises an N/P ratio from 0.01 to 0.2, or from 0.05 to 0.5, or from 0.1 to 1.0, or from 0.5 to 2.0, or from 1.0 to 5.0. In some embodiments, the N/P ratio may be less than about 0.1. In some embodiments, the N/P ratio is the ratio of positively charged groups (including amine (N) groups) to negatively charged groups including phosphate (P) and peptide groups. In some embodiments, the lipid composition further comprises at least one neutral lipid. In some embodiments, the peptide comprises SEQ ID NO. 1 and a polycationic nucleic acid binding domain. In some embodiments, the peptide comprises at least 80% sequence identity to GLFEALLELLESLWELLLEA (SEQ ID NO: 6).

In another aspect, provided is a composition for delivery of a payload to a spleen cell, where the composition comprises at least one ionizable lipid and at least one peptide comprising the sequence LLELLESL (SEQ ID NO: 1). In some embodiments, the composition for delivery of a payload to a spleen cell further comprises at least one neutral lipid. In some embodiments, in the composition for delivery of a payload to a spleen cell, the peptide comprising SEQ ID NO. 1 is present at a concentration of less than 1.0 mg/ml. In some embodiments, the peptide comprises at least 80% sequence identity to GLFEALLELLESLWELLLEA (SEQ ID NO: 6). In some embodiments, the composition for delivery of a payload to a spleen cell further comprises at least one payload.

Provided herein are, inter alia, methods, compositions and kits for targeting a payload to an immune cell, such as a spleen cell in vitro, ex vivo, or in a subject. In some embodiments of such methods, Provided herein are, inter alia, methods, compositions and kits for inducing an immune response in a subject.

Provided herein are, inter alia, methods and compositions for making a population of lipid formulations containing a payload.

General Definitions

The following definitions are included for the purpose of understanding the present subject matter and for constructing the appended patent claims. The abbreviations used herein have their conventional meanings within the chemical and biological arts.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this invention. The following definitions are provided to facilitate understanding of certain terms used frequently herein and are not meant to limit the scope of the present disclosure.

The term "about" when used in reference to numerical ranges, cutoffs, or specific values is used to indicate that the recited values may vary by up to as much as 25% from the listed value. As many of the numerical values used herein are experimentally determined, it should be understood by those skilled in the art that such determinations can, and often times will, vary among different experiments. The values used herein should not be considered unduly limiting by virtue of this inherent variation. The term "about" is used to encompass variations of ±25% or less, variations of ±20% or less, variations of 10% or less, variations of ±5% or less, variations of ±1% or less, variations of ±0.5% or less, or variations of ±0.1% or less from the specified value. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

In the descriptions herein and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

Compounds are generally described herein using standard nomenclature. For a recited compound having asymmetric center(s), all of the stereoisomers of the compound and mixtures thereof are encompassed unless otherwise specified. Non-limiting examples of stereoisomers include enantiomers, diastereomers, and E or Z isomers. Where a recited compound exists in various tautomeric forms, the compound is intended to encompass all tautomeric forms. Certain compounds are described herein using general formulas that include variables (e.g., X, $L_1$, $L_2$, $L_3$, Y, etc.). Unless otherwise specified, each variable within such a formula is defined independently of any other variable, and any variable that occurs more than one time in a formula is defined independently at each occurrence. If moieties are described as being "independently" selected from a group, each moiety is selected independently from the other. Each moiety therefore can be identical to or different from the other moiety or moieties. The number of carbon atoms in a hydrocarbyl moiety can be indicated by the prefix "$C_x$-$C_y$," where x is the minimum and y is the maximum number of carbon atoms in the moiety. Thus, for example, "$C_1$-$C_6$ alkyl" refers to an alkyl substituent containing from 1 to 6 carbon atoms. Illustrating further, $C_3$-$C_6$ cycloalkyl means a saturated hydrocarbyl ring containing from 3 to 6 carbon ring atoms. A prefix attached to a multiple-component substituent only applies to the first component that immediately follows the prefix. To illustrate, the term "carbocyclylalkyl" contains two components: carbocyclyl and alkyl. Thus, for example, $C_3$-$C_6$ carbocyclyl $C_1$-$C_6$ alkyl refers to a $C_3$-$C_6$ carbocyclyl appended to the parent molecular moiety through a $C_1$-$C_6$ alkyl group.

Unless otherwise specified, when a linking element links two other elements in a depicted chemical structure, the leftmost-described component of the linking element is bound to the left element in the depicted structure, and the rightmost-described component of the linking element is bound to the right element in the depicted structure. To illustrate, if the chemical structure is -$L_S$-M-$L_{S''}$- and M is —N($R_B$)S(O)—, then the chemical structure is -$L_S$-N($R_B$)S(O)-$L_{S''}$-.

If a linking element in a depicted structure is a bond, then the element left to the linking element is joined directly to the element right to the linking element via a covalent bond. For example, if a chemical structure is depicted as -$L_S$-M-$L_{S'}$ and M is selected as bond, then the chemical structure will be -$L_S$-$L_{S''}$-. If two or more adjacent linking elements in a depicted structure are bonds, then the element left to these linking elements is joined directly to the element right to these linking elements via a covalent bond. For instance, if a chemical structure is depicted as -$L_S$-M-$L_{S''}$-M'-$L_{S''}$-, and M and $L_{S'}$ are selected as bonds, then the chemical structure will be -$L_S$-M'-$L_{S''}$-. Likewise, if a chemical structure is depicted as -$L_S$-M-$L_{S''}$-M'-$L_{S''}$-, and M, $L_{S'}$ and M' are bonds, then the chemical structure will be -$L_S$-$L_{S''}$. When a chemical formula is used to describe a moiety, the dash(es) indicates the portion of the moiety that has the free valence(s).

If a moiety is described as being "optionally substituted", the moiety may be either substituted or unsubstituted. If a moiety is described as being optionally substituted with up to a particular number of non-hydrogen radicals that moiety may be either unsubstituted, or substituted by up to that particular number of non-hydrogen radicals or by up to the maximum number of substitutable positions on the moiety, whichever is less. Thus, for example, if a moiety is described as a heterocycle optionally substituted with up to three non-hydrogen radicals, then any heterocycle with less than three substitutable positions will be optionally substituted by up to only as many non-hydrogen radicals as the heterocycle has substitutable positions. For example, tetrazolyl (which has only one substitutable position) will be optionally substituted with up to one non-hydrogen radical. Similarly, if an amino nitrogen is described as being optionally substituted with up to two non-hydrogen radicals, then a primary amino nitrogen will be optionally substituted with up to two non-hydrogen radicals, whereas a secondary amino nitrogen will be optionally substituted with up to only one non-hydrogen radical.

Where a moiety is substituted with oxo or thioxo, it means that the moiety contains a carbon atom covalently bonded to at least two hydrogens (e.g., CH2), and the two hydrogen radicals are substituted with oxo or thioxo to form C═O or C═S, respectively. The term "alkenyl" means a straight or branched hydrocarbyl chain containing one or more double bonds. Each carbon-carbon double bond may have either E (cis) or Z (trans) geometry within the alkenyl moiety, relative to groups substituted on the double bond carbons. Examples of alkenyl radicals include, but are not limited to, ethenyl, E- and Z-propenyl, isopropenyl, E- and Z-butenyl, E- and Z-isobutenyl, E- and Z-pentenyl, E- and Z-hexenyl, E,E-, E,Z-, Z,E- and Z,Z-hexadienyl and the like.

The term "alkenylene" refers to a divalent unsaturated hydrocarbyl chain which may be linear or branched and which has at least one carbon-carbon double bond. Non-limiting examples of alkenylene groups include —C(H)═C(H)—, —C(H)═C(H)—$CH_2$—, —C(H)═C(H)—$CH_2$—$CH_2$—, —$CH_2$—C(H)═C(H)—$CH_2$—, —C(H)═C(H)—CH—($CH_3$)—, and —$CH_2$—C(H)═C(H)—CH—($CH_2CH_3$)—.

The term "alkyl" means a straight or branched saturated hydrocarbyl chain. Non-limiting examples of alkyl groups include methyl, ethyl, n-propyl, isopropyl, n-butyl, isobutyl, sec-butyl, t-butyl, pentyl, iso-amyl, and hexyl.

The term "alkylene" denotes a divalent saturated hydrocarbyl chain which may be linear or branched. Representative examples of alkylene include, but are not limited to, —$CH_2$—, —$CH_2CH_2$—, —$CH_2CH_2CH_2$—, —$CH_2CH_2CH_2CH_2$—, and —$CH_2CH(CH_3)CH_2$—.

The term "alkynyl" means a straight or branched hydrocarbyl chain containing one or more triple bonds. Non-limiting examples of alkynyl include ethynyl, 1-propynyl, 2-propynyl, 3-propynyl, decynyl, 1-butynyl, 2-butynyl, and 3-butynyl.

The term "alkynyl," alone or in combination with any other term, refers to a straight-chain or branched-chain hydrocarbon radical having one or more triple bonds containing the specified number of carbon atoms, or where no number is specified, in one embodiment from 2 to about 10 carbon atoms. Examples of alkynyl radicals include, but are not limited to, ethynyl, propynyl, propargyl, butynyl, pentynyl and the like.

The term "alkoxy" refers to an alkyl ether radical, wherein the term "alkyl" is defined above. Examples of suitable alkyl ether radicals include, but are not limited to, methoxy, ethoxy, n-propoxy, isopropoxy, n-butoxy, isobutoxy, sec-butoxy, tert-butoxy and the like.

The term "aryl," alone or in combination with any other term, refers to a carbocyclic aromatic radical (such as phenyl or naphthyl) containing the specified number of carbon atoms, in one embodiment from 6-15 carbon atoms (i.e. ($C_{6-15}$) aryl), and in another embodiment from 6-10 carbon atoms (i.e. ($C_{6-10}$) aryl), optionally substituted with one or more substituents selected from alkyl, alkoxy, (for example methoxy), nitro, halogen, (for example chloro), amino, carboxylate and hydroxy. Examples of aryl radicals include, but are not limited to phenyl, p-tolyl, 4-hydroxyphenyl, 1-naphthyl, 2-naphthyl, indenyl, indanyl, azulenyl, fluorenyl, anthracenyl and the like.

The term "aralkyl", alone or in combination, means an alkyl radical as defined above in which one hydrogen atom is phenyl, benzyl, 2-phenylethyl and the like.

The term "aralkoxycarbonyl", alone or in combination, means a radical of the formula —C(O)—O-aralkyl in which the term "aralkyl" has the significance given above. An example of an aralkoxycarbonyl radical is benzyloxycarbonyl.

The term "aryloxy", alone or in combination, means a radical of the formula aryl-O— in which the term "aryl" has the significance given above.

The term "alkynylene" refers to a divalent unsaturated hydrocarbon group which may be linear or branched and which has at least one carbon-carbon triple bonds. Representative alkynylene groups include, by way of example, —C≡C—, —C≡C—$CH_2$—, —C≡C—$CH_2$—$CH_2$—, —$CH_2$—C≡C—$CH_2$—, —C≡C—CH($CH_3$)—, and —$CH_2$—C≡C—CH($CH_2CH_3$)—.

The term "alkanoyl", alone or in combination, means an acyl radical derived from an alkanecarboxylic acid, examples of which include acetyl, propionyl, butyryl, valeryl, 4-methylvaleryl, and the like.

The term "aryloxyalkanoyl" means an acyl radical of the formula aryl-O-alkanoyl wherein aryl and alkanoyl have the significance given above.

The term "aralkanoyl" means an acyl radical derived from an aryl-substituted alkanecarboxylic acid such as phenylacetyl, 3-phenylpropionyl (hydrocinnamoyl), 4-phenylbutyryl, (2-naphthyl) acetyl, 4-chlorohydrocinnamoyl, 4-aminohydrocinnamoyl, 4-phenylbutyryl, (1-naphthyl) acetyl, 4-chlorohydrocinnamoyl, 4-aminohydrocinnamoyl, 4-methoxyhydrocinnamoyl, and the like.

The term "aroyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-benzyloxycarbonyl)benzoyl, 1-naphthoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The term "aminocarbonyl" alone or in combination, means an amino-substituted carbonyl (carbamoyl) group derived from an amino-substituted carboxylic acid wherein the amino group can be a primary, secondary or tertiary amino group continuing substituents selected from hydrogen, alkyl, aryl, aralkyl, cycloalkyl, cycloalkylalkyl radicals and the like.

The term "aminoalkanoyl" means an acyl radical derived from an amino substituted alkanecarboxylic acid wherein the amino group can be a primary, secondary or tertiary amino group containing substituents selected from the group consisting of hydrogen, cycloalkyl, cycloalkylalkyl radicals and the like, examples of which include N,N-dimethylaminoacetyl and N-benzylaminoacetyl.

The term "carbocycle" or "carbocyclic" or "carbocyclyl" refers to a saturated (e.g., "cycloalkyl"), partially saturated (e.g., "cycloalkenyl" or "cycloalkynyl") or completely unsaturated (e.g., "aryl") 3- to 8-membered carbon ring system containing zero heteroatom ring atom. "Ring atoms" or "ring members" are the atoms bound together to form the ring or rings. A carbocyclyl may be, without limitation, a single ring, two fused rings, or bridged or spiro rings. A substituted carbocyclyl may have either cis or trans geometry. Representative examples of carbocyclyl groups include, but are not limited to, cyclopropyl, cyclobutyl, cyclopentyl, cyclohexyl, cycloheptyl, cyclooctyl, cyclopentenyl, cyclopentadienyl, cyclohexadienyl, adamantyl, decahydro-naphthalenyl, octahydro-indenyl, cyclohexenyl, phenyl, naphthyl, indanyl, 1,2,3,4-tetrahydro-naphthyl, indenyl, isoindenyl, decalinyl, and norpinanyl. A carbocycle group can be attached to the parent molecular moiety through any substitutable carbon ring atom. Where a carbocycle group is a divalent moiety linking two other elements in a depicted chemical structure, the carbocycle group can be attached to the two other elements through any two substitutable ring atoms. Likewise, where a carbocycle group is a trivalent moiety linking three other elements in a depicted chemical structure, the carbocycle group can be attached to the three other elements through any three substitutable ring atoms, respectively. The carbocycle may be attached at any endocyclic carbon atom which results in a stable structure. Carbocycles in one embodiment have 5-7 carbons.

The term "cycloalkyl" refers to a saturated carbocyclyl group containing zero heteroatom ring member. Non-limiting examples of cycloalkyls include cyclopropyl, cyclobutyl, cyclopentyl, cyclohexyl, cycloheptyl, cyclooctyl, decalinyl and norpinanyl.

The term "cycloalkyl", alone or in combination, means an alkyl radical which contains from about 3 to about 8 carbon atoms and is cyclic. Examples of such cycloalkyl radicals include cyclopropyl, cyclobutyl, cyclopentyl, cyclohexyl and the like.

The term "cycloalkylalkyl" means an alkyl radical as defined above which is substituted by a cycloalkyl radical containing from about 3 to about 8, in one embodiment from about 3 to about 6, carbon atoms.

The term "cycloalkylcarbonyl" means an acyl group derived from a monocyclic or bridged cycloalkanecarboxylic acid such as cyclopropanecarbonyl, cyclohexanecarbonyl, adamantanecarbonyl, and the like, or from a benz-fused monocyclic cycloalkanecarboxylic acid which is optionally substituted by, for example, alkanoylamino, such as 1,2,3,4-tetrahydro-2-naphthoyl, 2-acetamido-1,2,3,4-tetrahydro-2-naphthoyl.

The term "cycloalkylalkoxycarbonyl" means an acyl group derived from a cycloalkylalkoxycarboxylic acid of the formula cycloalkylalkyl-O—COOH wherein cycloalkylalkyl has the significance given above.

The term "carbocyclylalkyl" refers to a carbocyclyl group appended to the parent molecular moiety through an alkylene group. For instance, $C_3$-$C_6$carbocyclyl$C_1$-$C_6$alkyl refers to a $C_3$-$C_6$carbocyclyl group appended to the parent molecular moiety through $C_1$-$C_6$alkylene.

The term "cycloalkenyl" refers to a non-aromatic, partially unsaturated carbocyclyl moiety having zero heteroatom ring member. Representative examples of cycloalkenyl groups include, but are not limited to, cyclobutenyl, cyclopentenyl, cyclohexenyl, and octahydronaphthalenyl.

The prefix "halo" indicates that the substituent to which the prefix is attached is substituted with one or more independently selected halogen radicals. For example, "$C_1$-$C_6$haloalkyl" means a $C_1$-$C_6$alkyl substituent wherein one or more hydrogen atoms are replaced with independently selected halogen radicals. Non-limiting examples of $C_1$-$C_6$haloalkyl include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The term "heterocycle" or "heterocyclo" or "heterocyclyl" refers to a saturated (e.g., "heterocycloalkyl"), partially unsaturated (e.g., "heterocycloalkenyl" or "heterocycloalkynyl") or completely unsaturated (e.g., "heteroaryl") ring system where at least one of the ring atoms is a heteroatom (i.e., nitrogen, oxygen or sulfur), with the remaining ring atoms being independently selected from the group consisting of carbon, nitrogen, oxygen and sulfur. A heterocycle may be, without limitation, a single ring, two fused rings, or bridged or spiro rings. A heterocycle group can be linked to the parent molecular moiety via any substitutable carbon or nitrogen atom(s) in the group. Where a heterocycle group is a divalent moiety that links two other elements in a depicted chemical structure, the heterocycle group can be attached to the two other elements through any two substitutable ring atoms. Likewise, where a heterocycle group is a trivalent moiety that links three other elements in a depicted chemical structure, the heterocycle group can be attached to the three other elements through any three substitutable ring atoms, respectively.

In the instant compounds, "Het" indicates a heterocycle containing 4-12 carbon atom, where at least one nitrogen atom is present in the ring(s). A heterocyclyl may be, without limitation, a monocycle which contains a single ring. Non-limiting examples of monocycles include furanyl, dihydrofuranyl, tetrahydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazolyl (including 1,2,3-oxadiazolyl, 1,2,4-oxadiazolyl (also known as "azoximyl"), 1,2,5-oxadiazolyl (also known as "furazanyl"), and 1,3,4-oxadiazolyl), oxatriazolyl (including 1,2,3,4-oxatriazolyl and 1,2,3,5-oxatriazolyl), dioxazolyl (including 1,2,3-dioxazolyl, 1,2,4-dioxazolyl, 1,3,2-dioxazolyl, and 1,3,4-dioxazolyl), pyridinyl, piperidinyl, diazinyl (including pyridazinyl (also known as "1,2-diazinyl"), pyrimidinyl (also known as "1,3-diazinyl"), and pyrazinyl (also known as "1,4-diazinyl")), piperazinyl, triazinyl (including s-triazinyl (also known as "1,3,5-triazinyl"), astriazinyl (also known 1,2,4-triazinyl), and v-triazinyl (also known as "1,2,3-triazinyl), oxazinyl (including 1,2,3-oxazinyl, 1,3,2-oxazinyl, 1,3,6-oxazinyl (also known as "pentoxazolyl"), 1,2,6-oxazinyl, and 1,4-oxazinyl), isoxazinyl (including o-isoxazinyl and p-isoxazinyl), oxazolidinyl, isoxazolidinyl, oxathiazinyl (including 1,2,5-oxathiazinyl or 1,2,6-oxathiazinyl), oxadiazinyl (including 1,4,2-oxadiazinyl and 1,3,5,2-oxadiazinyl), morpholinyl, azepinyl, and diazepinyl.

A heterocyclyl may also be, without limitation, a bicycle containing two fused rings, such as, for example, naphthyridinyl (including [1,8]naphthyridinyl, and [1,6]naphthyridinyl), thiazolpyrimidinyl, thienopyrimidinyl, pyrimidopyrimidinyl, pyridopyrimidinyl, pyrazolopyrimidinyl, indolizinyl, pyrindinyl, pyranopyrrolyl, 4H-quinolizinyl, purinyl, pyridopyridinyl (including pyrido[3,4-b]-pyridinyl, pyrido[3,2-b]-pyridinyl, and pyrido[4,3-b]-pyridinyl), pyridopyrimidine, and pteridinyl. Other non-limiting examples of fused-ring heterocycles include benzo-fused heterocyclyls, such as indolyl, isoindolyl, indoleninyl (also known as "pseudoindolyl"), isoindazolyl (also known as "benzpyrazolyl" or indazolyl), benzazinyl (including quinolinyl (also known as "1-benzazinyl") and isoquinolinyl (also known as "2-benzazinyl")), benzimidazolyl, phthalazinyl, quinoxalinyl, benzodiazinyl (including cinnolinyl (also known as "1,2-benzodiazinyl") and quinazolinyl (also known as "1,3-benzodiazinyl")), benzothiazolyl, 4,5,6,7-tetrahydrobenzo[d]thiazolyl, benzothiadiazolyl, benzimidazolyl, benzotriazolyl, benzoxazinyl (including 1,3,2-benzoxazinyl, 1,4,2-benzoxazinyl, 2,3,1-benzoxazinyl, and 3,1,4-benzoxazinyl), benzisoxazinyl (including 1,2-benzisoxazinyl and 1,4-benzisoxazinyl), and tetrahydroisoquinolinyl.

A heterocyclyl may also be, without limitation, a spiro ring system, such as, for example, 1,4-dioxa-8-azaspiro[4.5]decanyl. A heterocyclyl may comprise one or more sulfur atoms as ring members; and in some cases, the sulfur atom(s) is oxidized to SO or $SO_2$. The nitrogen heteroatom(s) in a heterocyclyl may or may not be quaternized, and may or may not be oxidized to N-oxide. In addition, the nitrogen heteroatom(s) may or may not be N-protected.

A heterocycle or carbocycle may be further substituted. Unless specified, the term "substituted" refers to substitution by independent replacement of one, two, or three or more of the hydrogen atoms with substituents including, but not limited to, —F, —Cl, —Br, —I, hydroxy, protected hydroxy, $—NO_2$, $—N_3$, —CN, $—NH_2$, protected amino, oxo, thioxo, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, $—CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, $—OCO_2$—$C_1$-$C_{12}$-alkyl, $—OCO_2$—$C_2$-$C_8$-alkenyl, $—OCO_2$—$C_2$-$C_8$-alkynyl, $—OCO_2$—$C_3$-$C_{12}$-cycloalkyl, $—OCO_2$-aryl, $—OCO_2$-heteroaryl, $—OCO_2$-heterocycloalkyl, $—OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocycloalkyl, $—NHCO_2$—$C_1$-$C_{12}$-alkyl, $—NHCO_2$—$C_2$-$C_8$-alkenyl, $—NHCO_2$—$C_2$-$C_8$-alkynyl, $—NHCO_2$—$C_3$-$C_{12}$-cycloalkyl, $—NHCO_2$-aryl, $—NHCO_2$-heteroaryl, $—NHCO_2$-heterocycloalkyl, $—NHC(O)NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, $—NHC(S)NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, $—NHC(NH)NH_2$, —NHC(NH)NH—$C_1$-$C_{12}$-alkyl, —NHC(NH)NH—$C_2$-$C_8$-alkenyl, NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, $—SO_2NH_2$, $—SO_2NH$—$C_1$-$C_{12}$-alkyl, $—SO_2NH$—$C_2$-$C_8$-alkenyl, $—SO_2NH$—$C_2$-$C_8$-alkynyl, $—SO_2NH$—$C_3$-$C_{12}$-cycloalkyl, $—SO_2NH$-aryl, $—SO_2NH$-heteroaryl, $—SO_2NH$-heterocycloalkyl, $—NHSO_2$—$C_1$-$C_{12}$-alkyl, $—NHSO_2$-$C_2$-$C_8$-alkenyl, $—NHSO_2$—$C_2$-$C_8$-alkynyl, $—NHSO_2$—$C_3$-$C_{12}$-cycloalkyl, $—NHSO_2$-aryl, $—NHSO_2$-heteroaryl, $—NHSO_2$-heterocycloalkyl, $—CH_2NH_2$, $—CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, -heteroaryl, —S-heterocycloalkyl, or methylthiomethyl. It is understood that the aryls, heteroaryls, alkyls, and the like can be further substituted.

The term "N-protecting group" or "N-protected" refers to those groups capable of protecting an amino group against undesirable reactions. Commonly used N-protecting groups are described in Greene and Wuts, *Protecting Groups in Chemical Synthesis* ($3^{rd}$ ed., John Wiley & Sons, NY (1999)). Non-limiting examples of N-protecting groups include acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, benzoyl, 4-chlorobenzoyl, 4-bromobenzoyl, or 4-nitrobenzoyl; sulfonyl groups such as benzenesulfonyl or p-toluenesulfonyl; sulfenyl groups such as phenylsulfenyl (phenyl-S—) or triphenylmethylsulfenyl (trityl-S—); sulfinyl groups such as p-methylphenylsulfinyl (p-methylphenyl-S(O)—) or t-butylsulfinyl (t-Bu-S(O)—); carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxy carbonyl, dimethyl-3,5-dimethoxybenzyloxycarbonyl, benzhydryloxycarbonyl, t-butyloxycarbonyl, diisopropylmethoxycarbonyl, isopropyloxy carbonyl, ethoxycarbonyl, methoxycarbonyl, allyloxycarbonyl, 2,2,2-trichloro-ethoxy-carbonyl, phenoxy carbonyl, 4-nitro-phenoxy carbonyl, cyclopentyloxycarbonyl, adamantyloxycarbonyl, cyclohexyloxycarbonyl, or phenylthiocarbonyl; alkyl groups such as benzyl, p-methoxybenzyl, triphenylmethyl, or benzyloxymethyl; p-methoxyphenyl; and silyl groups such as trimethylsilyl. Preferred N-protecting groups include formyl, acetyl, benzoyl, pivaloyl, t-butylacetyl, phenylsulfonyl, benzyl, t-butyloxycarbonyl (Boc) and benzyloxycarbonyl (Cbz).

The term "halogen" means fluorine, chlorine, bromine or iodine.

The terms "biologically active agent", "bioactive agents" or the like, generally refers to a composition, complex, compound or molecule which has a biological effect or that modifies, causes, promotes, enhances, blocks or reduces a biological effect, or that enhances or limits the production or activity of, reacts with and/or binds to a second molecules which has a biological effect. The second molecule can, but need not be, an endogenous molecule (e.g., a molecule, such as a protein or nucleic acid, normally present in the target cell). A biological effect may be, but is not limited to, one that stimulates or causes an immunoreactive response; one that impacts a biological process in a cell, tissue or organism (e.g., in an animal); one that imparts a biological process in a pathogen or parasite; one that generated or causes to be generated a detectable signal; one that regulates the expression of a protein or polypeptide; one that stops or inhibits the expression of a protein or polypeptide; or one that causes or enhances the expression of a protein or polypeptide. Biologically active compositions, complexes, compounds or molecules may be used in investigative, therapeutic, prophylactic and diagnostic methods and compositions and generally act to cause.

The term "transfection enhancer" or "transfection enhancing agent" as used herein refers to a compound when added to a transfection agent increases the efficiency of transfection (i.e., increases the percent of cells transfected), increases the level of expression of a transfection agent, or reduces the requirement for the amount of payload, for example nucleic acid or protein, required to give a biological response, or any combination of the enhancements above. In some embodiments, the transfection enhancer also helps deliver molecules that help downregulate expression such as siRNA, LNA's and the like. In some embodiments, the transfection enhancing agent is a peptide including, for example, a cell surface ligand, a fusion agent, and/or a nuclear localization agent such as a nuclear receptor ligand peptide. Transfection enhancing agents include the peptides and polypeptides described, for example, in Table 1 of U.S. Pat. No. 10,538,784, the contents of which is hereby incorporated by reference in its entirety.

The term "nucleic acid binding moiety" as used herein refers to a compound or molecule capable binding to nucleic acid. In some embodiments, the binding molecule is capable of noncovalently binding to nucleic acid, while in other embodiments, the binding molecule links covalently to a transfection enhaner, a cell surface ligand, a nuclear localization sequence, and/or a fusion agent. The binding molecule can include but is not limited to spermine, spermine derivative, spermidine, histones or fragments thereof, protamines or fragments thereof, HMG proteins or fragments thereof, poly-lysine, poly-arginine, poly-histidine, polyamines and cationic peptides, nucleic acid intercalaters, protein nucleic acid sequences or aptamers. In addition, this includes but is not limited to analogs or derivatives of the above compounds.

The term "polycationic nucleic acid binding moiety" as used herein refers to a moiety containing multiple positive charges at physiological pH that allow the moiety to bind a negatively charged nucleic acid. A polycationic nucleic acid binding moiety may be linked to, for example, a transfection enhancer such as a cell surface ligand, a fusion agent, and/or a nuclear localization peptide. The linkage may be covalent. Suitable polycationic nucleic acid binding moieties include polyamines and polybasic peptides containing, for example, multiple lysine, arginine, ornithine, or histidine residues, such as between about 8-20 such residues. Non limiting examples are the cationic peptides that are repeats of lysine or arginine, for example a sequence having between 8-20 lysine residues or between 8-20 arginine residues.

The terms "polypeptide," "peptide" and "protein" are used interchangeably herein to refer to a polymer of amino acid residues, wherein the polymer may in embodiments be conjugated to a moiety that does not consist of amino acids. The terms also apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed or chemically synthesized as a single moiety.

The term "lysis agent" or "endosomal release agent" as used herein refers to a molecule, compound, protein or peptide which is capable of breaking down an endosomal membrane or cell membrane and freeing the transfection agent, such as payload transporter including an RNA or DNA transporter, into the cytoplasm of the cell. This term includes but is not limited to viruses, synthetic compounds, fusion peptides, cell penetration peptides, lytic peptides, or derivatives thereof. The term "lytic peptide" refers to a chemical grouping which penetrates a membrane such that the structural organization and integrity of the membrane is lost. As a result of the presence of the lysis agent, the membrane undergoes lysis, fusion or both. Examples of lysis agents/endosomal release agents include choroquine, polyamines and polyamidoamines. Suitable agents are described in, for example, Pei and Buyanova, *Bioconjugate Chem,* 30:273-283 (2009) and Juliano, *Nucleic Acid Therapeutics,* 28:166-177 (2018).

The term "surface ligand" or "cell surface ligand" refers to a chemical compound or structure which will bind to a surface receptor of a cell. The term "cell surface receptor" as used herein refers to a specific chemical grouping on the surface of a cell to which the ligand can attach. Cell surface receptors can be specific for a particular cell, i.e., found predominantly in one cell rather than in another type of cell (e.g., LDL and asialoglycoprotein receptors are specific for hepatocytes). The receptor facilitates the internalization of the ligand and attached molecules. A cell surface receptor includes but is not limited to a folate receptor, biotin receptor, lipoic acid receptor, low-density lipoprotein receptor, asialoglycoprotein receptor, insulin-like growth factor type II/cation-independent mannose-6-phosphate receptor, calcitonin gene-related peptide receptor, insulin-like growth factor I receptor, nicotinic acetylcholine receptor, hepatocyte growth factor receptor, endothelin receptor, bile acid receptor, bone morphogenetic protein receptor, cartilage induction factor receptor or glycosylphosphatidylinositol (GPI)-anchored proteins (e.g., β-adrenergic receptor, T-cell activating protein, Thy-1 protein, GPI-anchored 5' nucleotidase). These are nonlimiting examples.

A "receptor" is a molecule to which a ligand binds specifically and with relatively high affinity. A receptor is usually a protein or a glycoprotein, but may also be a glycolipid, a lipidpolysaccharide, a glycosaminoglycan or a glycocalyx. For purposes of this disclosure, epitopes to which an antibody or its fragments binds is construed as a receptor since the antigen: antibody complex undergoes endocytosis. Furthermore, surface ligand includes anything which is capable of entering the cell through cytosis (e.g. endocytosis, potocytosis, pinocytosis). As used herein, the term "ligand" refers to a chemical compound or structure which will bind to a receptor. This includes but is not limited to ligands such as asialoorosomucoid, asialoglycoprotein, lipoic acid, biotin, apolipoprotein E sequence, insulin-like growth factor II, calcitonin gene-related peptide, thymopoietin, hepatocyte growth factor, endothelin-1, atrial natriuretic factor, RGD-containing cell adhesion peptides and the like. The ligand may also be a plant virus movement protein or peptide derived from such a protein. Suitable peptides and proteins are described, for example, in U.S. Pat. No. 10,538,784, the contents of which are hereby incorporated by reference in their entirety. One skilled in the art will readily recognize that a ligand chosen will depend on which receptor is being bound. Since different types of cells have different receptors, this provides one method of targeting a payload, such as a polypeptide or a nucleic acid molecule, to specific cell types, depending on which cell surface ligand is used. Thus, use of a cell surface ligand may depend on the targeted cell type.

Compositions

Provided herein, are lipid compositions comprising at least one ionizable lipid, at least one peptide comprising the sequence LLELLESL (SEQ ID NO: 1), and at least one payload molecule. In some embodiments, the lipid compositions further comprise at least one neutral lipid. In some embodiments, the peptide comprises at least 80% sequence identity to GLFEALLELLESLWELLLEA (SEQ ID NO: 1. In some embodiments, the peptide comprises a sequence selected from the group consisting of SEQ ID NOS: 1-24.

Exemplary payloads for delivery to tissues and cells via the provided lipid complex compositions include nucleic acid molecules, protein molecules and/or other bioactive agents. In some embodiments, the payload for delivery to an immune cell is a therapeutic agent or a diagnostic agent.

In some embodiments of the lipid compositions, the payload, such as one or more nucleic acids (e.g. mRNAs, siRNAs, sgRNAs), lipids, and amounts thereof may be selected to provide a specific N/P ratio. The N/P ratio of the composition refers to the molar ratio of ionizable (in physiological pH) nitrogen atoms in one or more lipids to the number of phosphate groups in a nucleic acid (e.g., an RNA). For example, Schoenmaker et al (International Journal of Pharmaceutics; 601 (2021), incorporated herein by reference in its entirety) discusses RNA-lipid nanoparticle N/P ratios (eg, mRNA and siRNA payloads) for example at Table 1 and p. 4.

In certain embodiments, a lower N/P ratio is preferred. Provided herein, are lipid compositions comprising at least one ionizable lipid having a charge (N), at least one peptide, wherein the peptide comprises the sequence LLELLESL (SEQ ID NO: 1), and a nucleic acid molecule comprising a charge (P), wherein the composition comprises an N/P ratio of 0.01, or of 0.02, or of 0.04, or of 0.06, or of 0.08, or of 0.10, or of 0.12, or of 0.14, or of 0.16, or of 0.18, or of 0.20. Provided herein, are lipid compositions comprising at least one ionizable lipid having a charge (N), at least one neutral lipid, at least one peptide, wherein the peptide comprises at least 80% sequence identity to GLFEALLELLESLWELLLEA (SEQ ID NO: 6), and a nucleic acid molecule comprising a charge (P), wherein the composition comprises an N/P ratio of 0.01, or of 0.02, or of 0.04, or of 0.06, or of 0.08, or of 0.10, or of 0.12, or of 0.14, or of 0.16, or of 0.18, or of 0.20. In other examples, the N/P ratio is from 0.01 to 0.10. In other examples, the N/P ratio is from 0.01 to 0.20. In other examples, the N/P ratio is from 0.01 to 0.25. In other examples, the N/P ratio is from 0.01 to 0.33. In other examples, the N/P ratio is from 0.01 to 0.5. In other examples, the N/P ratio is from 0.01 to 1. In other examples, the N/P ratio is from 0.05 to 0.1. In other examples, the N/P ratio is from 0.05 to 0.125. In other examples, the N/P ratio is from 0.5 to 0.15. In other examples, the N/P ratio is from 0.05 to 0.167. In other examples, the N/P ratio is from 0.05 to 0.20. In other examples, the N/P ratio is from 0.05 to 0.25. In other examples, the N/P ratio is from 0.05 to 0.33. In other examples, the N/P ratio is from 0.05 to 0.5. In other examples, the N/P ratio is from 0.05 to 1.0. In some embodiments, the N/P ratio may be less than about 0.1. In some embodiments the N/P ratio is 0.1. In some embodiments, the N/P ratio is 0.025. In other embodiments, the N/P ratio is 0.01. In some embodiments the N/P ratio is 0.005.

In certain embodiments, the one or more nucleic acids (e.g. mRNAs, siRNAs, sgRNAs), lipids, and amounts thereof may be selected to provide an N/P ratio from about 2.0 to about 8.0, such as 2, 3, 4, 5, 6, 7, and 8. In certain embodiments, the N/P ratio may be from about 2.0 to about 5.0. In some embodiments, the N/P ratio may be about 4.0. In other embodiments, the N/P ratio is from about 5 to about 8. For example, the N/P ratio may be about 5.0, about 5.5, about 5.67, about 6.0, about 6.5, or about 7.0.

In other embodiments, the one or more nucleic acids, lipids, and amounts thereof may be selected to provide an N/P ratio from about 5 to about 50, such as 5, 6, 7, 8, 9, 10, 12, 14, 16, 18, 20, 22, 24, 26, 28, 30, 32, 34, 36, 38, 40, 42, 44, 46, 48, or 50. In certain embodiments, the N/P ratio may be from about 5 to about 10. In other embodiments, the N/P ratio is from about 5 to about 20. In other embodiments, the N/P ratio may be from about 10 to about 20, about 10 to about 30, about 15 to about 30, about 15 to about 40, about 20 to about 30, about 20 to about 40, about 20 to about 50, about 30 to about 50, about 30 to about 40, or about 35 to about 50.

The ionizable lipid and peptide compositions provided herein encompass complexes in the form of lipid nanoparticles, liposomes (e.g., lipid vesicles) and lipoplexes. As used herein, the term "liposome" encompasses any compartment enclosed by a lipid bilayer. The term liposome includes unilamellar vesicles which are comprised of a single lipid bilayer and generally have a diameter in the range of about 20 to about 400 nm. Liposomes can also be multilamellar having a diameter in the range of approximately 1 μm to approximately 10 μm. Multilamellar liposomes may consist of several (anywhere from two to hundreds) unilamellar vesicles forming one inside the other in diminishing size, creating a multilamellar structure of concentric phospholipid spheres separated by layers of water. Alternatively, multilamellar liposomes may consist of many smaller nonconcentric spheres of lipid inside a large liposome. In embodiments, liposomes include multilamellar vesicles (MLV), large unilamellar vesicles (LUV), and small unilamellar vesicles (SUV). In some embodiments, the compositions include liposomes which contain any suitable ionizable lipid and neutral lipids, along with the peptide as provided herein.

In some embodiments, the compositions include lipid nanoparticles (LNPs). LNP composition are typically sized on the order of micrometers or small and may include a lipid bilayer. In some embodiments, the lipid nanoparticle composition comprises a lipid formulation, wherein the size is from about 20 nm to about 1 μm. In some embodiments, the lipid nanoparticle composition comprises a lipid formulation, wherein the size is from about 20 nm to about 900 μm. In some embodiments, the lipid nanoparticle composition comprises a lipid formulation, wherein the size is from about 20 nm to about 800 μm. In some embodiments, the lipid nanoparticle composition comprises a lipid formulation, wherein the size is from about 20 nm to about 700 μm. In some embodiments, the lipid nanoparticle composition comprises a lipid formulation, wherein the size is from about 20 nm to about 600 μm. In some embodiments, the lipid nanoparticle composition comprises a lipid formulation, wherein the size is from about 20 nm to about 500 μm. In some embodiments, the lipid nanoparticle composition comprises a lipid formulation, wherein the size is from about 20 nm to about 400 μm. In some embodiments, the lipid nanoparticle composition comprises a lipid formulation, wherein the size is from about 20 nm to about 300 μm. In some embodiments, the lipid nanoparticle composition comprises a lipid formulation, wherein the size is from about 20 nm to about 200 μm. In some embodiments, the lipid nanoparticle composition comprises a lipid formulation, wherein the size is from about 20 nm to about 100 μm. In some embodiments, the lipid nanoparticle composition comprises a lipid formulation, wherein the size is from about 20 nm to about 50 μm. In some embodiments, the lipid nanoparticle composition comprises a lipid formulation, wherein the size is from about 100 nm to about 900 μm. In some embodiments, the lipid nanoparticle composition comprises a lipid formulation, wherein the size is from about 100 nm to about 800 μm. In some embodiments, the lipid nanoparticle composition comprises a lipid formulation, wherein the size is from about 100 nm to about 700 μm. In some embodiments, the lipid nanoparticle composition comprises a lipid formulation, wherein the size is from about 100 nm to about 600 μm. In some embodiments, the lipid nanoparticle composition comprises a lipid formulation, wherein the size is from about 100 nm to about 500 μm. In some embodiments, the lipid nanoparticle composition comprises a lipid formulation, wherein the size is from about 100 nm to about 400 μm. In some embodiments, the lipid nanoparticle composition comprises a lipid formulation, wherein the size is from about 100 nm to about 300 μm. In some embodiments, the lipid nanoparticle composition comprises a lipid formulation, wherein the size is from about 100 nm to about 200 μm. In some embodiments, the lipid nanoparticle composition comprises a lipid formulation, wherein the size is from about 100 nm to about 150 μm.

The characteristics of a lipid nanoparticle (e.g., an LNP without payload or an LNP with payload) may depend on the components thereof. For example, a lipid nanoparticle including cholesterol as a structural lipid may have different characteristics than a lipid nanoparticle that includes a different structural lipid. Similarly, the characteristics of a lipid nanoparticle (e.g., an LNP without payload or an LNP with payload) may depend on the absolute or relative amounts of its components. For instance, a lipid nanoparticle including a higher molar fraction of a phospholipid may have different characteristics than a lipid nanoparticle including a lower molar fraction of a phospholipid. Characteristics may also vary depending on the method and conditions of preparation of the nanoparticle composition.

Lipid nanoparticles may be characterized by a variety of methods. For example, microscopy (e.g., transmission electron microscopy or scanning electron microscopy) may be used to examine the morphology and size distribution of a nanoparticle composition. Dynamic light scattering or potentiometry (e.g., potentiometric titrations) may be used to measure zeta potentials. Dynamic light scattering may also be utilized to determine particle sizes. Instruments such as the Zetasizer Nano ZS (Malvern Instruments Ltd, Malvern, Worcestershire, UK) may also be used to measure multiple characteristics of a nanoparticle composition, such as particle size, polydispersity index, and zeta potential.

The lipid complex compositions provided herein may be relatively homogenous. A polydispersity index may be used to indicate the homogeneity of a nanoparticle composition, e.g., the particle size distribution of the lipid nanoparticles. A small (e.g., less than 0.3) polydispersity index generally indicates a narrow particle size distribution. A lipid nanoparticle may have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a lipid nanoparticle (e.g., an LNP without payload or an LNP with payload) may be from about 0.10 to about 0.20.

The zeta potential of a lipid nanoparticle (e.g., an LNP without payload or an LNP with payload) may be used to indicate the electrokinetic potential of the composition. For example, the zeta potential may describe the surface charge of a nanoparticle composition. Lipid nanoparticles with relatively low charges, positive or negative, are generally desirable, as more highly charged species may interact undesirably with cells, tissues, and other elements in the body. In some embodiments, the zeta potential of a lipid nanoparticle may be from about −10 mV to about +20 mV, from about −10 mV to about +15 mV, from about −10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

In some embodiments, the payload of the lipid complex composition is an RNA molecule. For example, the payload RNA molecule comprises mRNA, siRNA, shRNA, miRNA, self-replicating RNA (srRNA), self-amplifying RNA, stRNA, sgRNA, or combinations thereof. In some embodiments, the payload RNA molecule includes more than one mRNA molecule (e.g., at least 2 mRNA molecules, at least 3 mRNA molecules, at least four mRNA molecules, or at least 5 mRNA molecules). In some embodiments, the payload includes at least one sgRNA. In other embodiments, the payload of the lipid complex composition molecule includes an sgRNA molecule and an mRNA molecule.

In some embodiments, the lipid composition payload includes a gene editing reagent (or a gene editing composition), and the gene editing reagent includes a gene editing protein, an RNA molecule, and/or a ribonucleoprotein (RNP). In various examples, the gene editing protein includes a zinc finger nuclease (ZFN), a transcription activator-like effector nuclease (TALEN), a Cas protein, a MegaTal, a Cre recombinase, a Hin Recombinase, or a Flp recombinase. In some embodiments, the RNA molecule includes sgRNA, a crRNA, and/or a tracrRNA. Accordingly, in some embodiments, the lipid complex composition payload includes an RNP and an sgRNA. In some embodiments, the RNP can include a Cas protein and a sgRNA, a crRNA or a tracrRNA.

In other embodiments, the RNA may encode a gene editing protein (e.g., an RNA encoding a ZFN, TALEN, Cas protein, Cre recombinase, etc). Accordingly, in some embodiments, the lipid complex composition payload includes an RNA encoding a gene editing protein and an sgRNA. In some embodiments, the lipid complex composition payload can include an RNA encoding a Cas protein and a sgRNA, a crRNA or a tracrRNA.

In some embodiments, the nucleic acid payload of the lipid complex compositions is a single-stranded molecule. In some embodiments, the payload may include donor DNA. In still other embodiments, the DNA payload may be a plasmid DNA or linear DNA. In some examples, the payload may be an RNP and include a Cas protein and a sgRNA, a crRNA or a tracrRNA.

In certain embodiments, the gene editing payload induces single-strand or double-strand breaks in DNA within the cells. In some embodiments the gene editing reagent (or gene editing composition) further comprises a repair template polynucleotide. In various embodiments, the repair template comprises (a) a first flanking region comprising nucleotides in a sequence complementary to about 40 to about 90 base pairs on one side of the single or double strand break and a second flanking region comprising nucleotides in a sequence complementary to about 40 to about 90 base pairs on the other side of the single or double strand break; or (b) a first flanking region comprising nucleotides in a sequence complementary to at least about 20, 25, 30, 35, 40, 45, 50, 60, 70, 80, or 90 base pairs on one side of the single or double strand break and a second flanking region comprising nucleotides in a sequence complementary to at least about 20, 25, 30, 35, 40, 45, 50, 60, 70, 80, or 90 base pairs on the other side of the single or double strand break. Non-limiting descriptions relating to gene editing (including repair templates) using the CRISPR-Cas system are discussed in Ran et al. (2013) Nat Protoc. 2013 November; 8 (11): 2281-2308, the entire content of which is incorporated herein by reference. Embodiments involving repair templates are not limited to those comprising the CRISPR-Cas system.

Non-limiting examples of Cas proteins include Cas1, Cas1B, Cas2, Cas3, Cas4, Cas5, Cas6, Cas7, Cas8, Cas9 (also known as Csn1 and Csx12), CaslO, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx1O, Csx16, CsaX, Csx3, Csx1, Csx15, Csf1, Csf2, Csf3, Csf4, homologs thereof, or modified versions thereof. These enzymes are known; for example, the amino acid sequence of *S. pyogenes* Cas9 protein may be found in the SwissProt database under accession number Q99ZW2 and in the NCBI database as under accession number Q99ZW2.1. UniProt database accession numbers A0A0G4DEU5 and CDJ55032 provide another example of a Cas9 protein amino acid sequence. Another non-limiting example is a *Streptococcus thermophilus* Cas9 protein, the amino acid sequence of which may be found in the UniProt database under accession number Q03JI6.1. In some embodiments, the unmodified CRISPR enzyme has DNA cleavage activity, such as Cas9. In certain embodiments the CRISPR enzyme is Cas9, and may be Cas9 from *S. pyogenes* or *S. pneumoniae*. In various embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. In aspects of the invention, nickases may be used for genome editing via homologous recombination.

In certain embodiments, the payload may include a Cas9 nickase used in combination with guide sequence(s), e.g., two guide sequences, which target respectively sense and antisense strands of the DNA target. This combination allows both strands to be nicked and used to induce NHEJ.

In still some examples, the payload of the lipid composition includes an RNA molecule, and the RNA molecule includes sgRNA, a crRNA, a tracrRNA, or combinations thereof.

In some embodiments, the payload of the lipid composition is an immunogen. In some embodiments, the nucleic acid payload of the lipid composition encodes for an immunogen. In some examples the payload nucleic acid of the lipid composition encodes for a hemagglutinin (HA) protein or fragment thereof. In some examples the nucleic acid payload of the lipid composition encodes for ovalbumin or fragment thereof. In examples, the lipid composition delivers a payload which induces an immune response in a subject to the protein or nucleic acid-encoded protein of the lipid composition.

Exemplary transfection enhancing peptides for use in the lipid composition are provided herein. In some embodiments, such peptides comprise the sequence LLELLESL (SEQ ID NO: 1) and optionally comprise a polycationic nucleic acid binding moiety. In some embodiments, the peptide comprises ALLELLESL (SEQ ID NO: 2), ELLELLESL (SEQ ID NO: 3), LLELLESLW (SEQ ID NO: 4) and/or LLELLESLY (SEQ ID NO: 5). In some embodiments, the peptide comprises one or more PSYYRYD (SEQ ID NO: 25) or PSYYRGD (SEQ ID NO: 26) sequences and optionally comprises a polycationic nucleic acid binding moiety.

As described herein, suitable polycationic nucleic acid binding moieties include without limitation polyamines and polybasic peptides containing, for example, poly-arginine, poly-lysine, poly-histidine, and/or poly-ornithine sequences with, for example, lengths of about 8 to about 20 residues.

The peptides for use in the compositions provided herein are at least 10 amino acids in length. In some embodiments, the peptides are at least 10 to about 100, at least 10 to about 75, at least 10 to about 50, at least 10 to about 40, at least 10 to about 30, or at least 10 to about 20 amino acids in length. In certain embodiments, the peptides are about 15 to about 25, about 15 to about 30, about 15 to about 40, about 15 to about 50, about 15 to about 60, or about 15 to about 70 amino acids in length. In some embodiments, the peptides are about 20 to about 30, about 20 to about 40, about 20 to about 50, about 20 to about 60, about 20 to about 70, or about 20 to about 80 amino acids in length.

In some examples, the peptide has at least 80% sequence identity to SEQ ID NO: 6 (GLFEALLELLESLWELLLEA). In other examples, the peptide includes SEQ ID NO: 6, or fragments thereof. In other examples, the peptide has at least 85% sequence identity to SEQ ID NO: 6. In other examples, the peptide has at least 90% sequence identity to SEQ ID NO: 6. In other examples, the peptide has at least 91% sequence identity to SEQ ID NO: 6. In other examples, the peptide has at least 92% sequence identity to SEQ ID NO: 6. In other examples, the peptide has at least 93% sequence identity to SEQ ID NO: 6. In other examples, the peptide has at least 94% sequence identity to SEQ ID NO: 6. In other examples, the peptide has at least 95% sequence identity to SEQ ID NO: 6. In other examples, the peptide has at least 96% sequence identity to SEQ ID NO: 6. In other examples, the peptide has at least 97% sequence identity to SEQ ID NO: 6. In other examples, the peptide has at least 98% sequence identity to SEQ ID NO: 6. In other examples, the peptide has at least 99% sequence identity to SEQ ID NO: 6. In other examples, the peptide has 100% sequence identity to SEQ ID NO: 6.

"Polypeptide fragment" refers to a polypeptide that has an amino-terminal and/or carboxy-terminal deletion, in which the remaining amino acid sequence is usually identical to the corresponding positions in the naturally-occurring sequence. Fragments typically are at least 5, 6, 8 or 10 amino acids long, at least 14 amino acids long, at least 20 amino acids long, at least 50 amino acids long, or at least 70 amino acids long.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. In embodiments, the percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "identical" or percent "identity," in the context of two or more nucleic acids or polypeptide sequences, refer to two or more sequences or subsequences that are the same or have a specified percentage of amino acid residues or nucleotides that are the same (e.g., 50%, 55%, 60%, 65%, 70%, 75%, 80%, 85%, 90%, 91%, 92%, 93%, 94%, 95%, 96%, 97%, 98%, 99%, or more identity over a specified region, e.g., of an entire polypeptide sequence or an individual domain thereof), when compared and aligned for maximum correspondence over a comparison window, or designated region as measured using a sequence comparison algorithm or by manual alignment and visual inspection. In embodiments, two sequences are 100% identical. In embodiments, two sequences are 100% identical over the entire length of one of the sequences (e.g., the shorter of the two sequences where the sequences have different lengths). In embodiments, identity may refer to the complement of a test sequence. In embodiments, the identity exists over a region that is at least about 10 to about 100, about 20 to about 75, about 30 to about 50 amino acids or nucleotides in length. In embodiments, the identity exists over a region that is at least about 50 amino acids or nucleotides in length, or more preferably over a region that is 100 to 500, 100 to 200, 150 to 200, 175 to 200, 175 to 225, 175 to 250, 200 to 225, 200 to 250 or more amino acids or nucleotides in length.

Exemplary peptides useful in the formulations provided herein include, without limitation, the peptides of Table 1.

TABLE 1

Peptide sequences

| SEQ ID NO: | Sequence |
|---|---|
| 6 | GLFEALLELLESLWELLLEA |
| 7 | GLFEALLELLESLYELLLEA |
| 8 | GLFEALLELLESLWELLLEAWYG |
| 9 | GLFEALLELLESLWELLLEAKK |
| 10 | GLFEALLELLESLWELLLEAKKKK |
| 11 | GLFEALLELLESLWELLLEAKKKKKK |
| 12 | GLFEALLELLESLWELLLEAKKKKKKKK |
| 13 | GLFEALLELLESLWELLLEAEE |
| 14 | GLFEALLELLESLWELLLEAEEEE |
| 15 | GLFEALLELLESLWELLLEAEEEEEE |
| 16 | GLFEALLELLESLWELLLEAEEEEEEEE |
| 17 | GLFEALLELLESLWELLLEARR |
| 18 | GLFEALLELLESLWELLLEARRRR |
| 19 | GLFEALLELLESLWELLLEARRRRRR |
| 20 | GLFEALLELLESLWELLLEARRRRRRRR |
| 21 | GLFEALLELLESLWELLL |
| 22 | GLLEELLELLEELWEELLEG |

TABLE 1-continued

| Peptide sequences | |
|---|---|
| SEQ ID NO: | Sequence |
| 23 | GLFEALLELLESLWELLLEAGSGSGSGSRRRRRRRRRRRR |
| 24 | GLFEALLELLESLWELLLEAGSSSGSSSGSSSRRRRRRRRRRRR |

In some embodiments, any of the SEQ ID NO: 1-22 peptides may further comprise arginine residues or additional arginine residues (e.g., R2, R4, R6, R8, R12) at the N or C terminus. In other embodiments, any of SEQ ID NO: 1-22 may further comprise lysine residues or additional lysine (e.g., K2, K4, K6, K8, K12) at the N or C terminus. In other embodiments, any of the SEQ ID NO: 1-22 peptides may comprise multiple histidine residues (e.g., H2, H4, H6, H8, H12) at the N or C terminus. In other embodiments, any of the SEQ ID NO: 1-22 peptides may comprise multiple ornithine residues at the N or C terminus. In certain embodiments, the SEQ ID NO: 1-22 sequence is connected to the multiple arginine, lysine, histidine or ornithine residues by a spacer or linker molecule.

In some embodiments, in addition to the peptide comprising one or more of SEQ ID NO: 1-5 or to the peptide that has at least 80% sequence identity to any one of SEQ ID NO: 6-24, formulations may include additional transfection enhancing agents such as a cell surface ligand peptide and/or a nuclear localization agent such as a nuclear receptor ligand peptide. Examples of such transfection enhancing agents include, but are not limited to, reovirus-related fusogenic peptides, insulin, a transferrin, epidermal growth factor, fibroblast growth factor, a cell targeting antibody, a lactoferrin, a fibronectin, an adenovirus penton base, Knob, a hexon protein, a vesicular stomatitis virus glycoprotein, a Semliki Forest Virus core protein, a influenza hemagglutinin, a hepatitis B core protein, an HIV Tat protein, a herpes simplex virus VP22 protein, a histone protein, a arginine rich cell permeability protein, a high mobility group protein, and invasin protein, and internalin protein, an endotoxin, a diphtheria toxin, a *shigella* toxin, a melittin, a magainin, a gramicidin, a cecrophin, a defensin, a protegrin, a tachyplesin, a thionin, a indolicidin, a bactenecin, a drosomycin, an apidaecin, a cathelicidin, a bactericidal-permeability-increasing protein, a nisin, a buforin, and fragments thereof, and those disclosed in US Application Publication No. 2018/0340188 (which is hereby incorporated by reference in its entirety).

Exemplary transfection enhancing peptides useful in the formulations provided herein include, peptides comprising one or more sequences of PSYYRYD (SEQ ID NO: 25) and/or PSYYRGD (SEQ ID NO: 26) including, without limitation, the exemplary peptides of Table 2.

TABLE 2

| SEQ ID NO: | Sequence |
|---|---|
| 27 | AARSPSYYRGDYGPYYAMDYD RRRRRRRRRRRR |
| 28 | AARSPSYYRGDYGPYYAMDYD |
| 29 | AARSPSYYRGDAGPYYAMDYD RRRRRRRRRRRR |

TABLE 2-continued

| SEQ ID NO: | Sequence |
|---|---|
| 30 | AARSPSYYRGDAGPYYAMDYD |
| 31 | AARSPSYYRYDYGPYYAMDYD RRRRRRRRRRRR |
| 32 | AARSPSYYRYDYGPYYAMDYDR |
| 33 | PSYYRGDGAPSYYRGDGAPSYYRGDGARRRRRRRRRRRR |
| 34 | PSYYRGDGAPSYYRGDGAPSYYRGDGA |
| 35 | PSYYRYDYGPSYYRYDYGPSYYRYDYGRRRRRRRRRRRR |
| 36 | PSYYRYDYGPSYYRYDYGPSYYRYDYG |

In some embodiments, the transfection enhancing peptide comprises at least two PSYYRYD (SEQ ID NO: 25) and/or PSYYRGD (SEQ ID NO: 26) sequences or at least three PSYYRYD (SEQ ID NO: 25) and/or PSYYRGD (SEQ ID NO: 26) sequences. In some examples, the transfection enhancing peptide has at least 80% sequence identity to any one of SEQ ID NO: 27-36. In other examples, the transfection enhancing peptide includes any one of SEQ ID NO: 27-36, or fragments thereof. In other examples, the transfection enhancing peptide has at least 85% sequence identity to any one of SEQ ID NO: 27-36. In other examples, the transfection enhancing peptide has at least 90% sequence identity to any one of SEQ ID NO: 27-36. In other examples, the transfection enhancing peptide has at least 95% sequence identity to any one of SEQ ID NO: 27-36. In other examples, the transfection enhancing peptide has 100% sequence identity to any one of SEQ ID NO: 27-36. In some embodiments, any of the SEQ ID NO: 27-36 peptides may further comprise additional arginine residues (e.g., R2, R4, R6, R8, R10, R12, R14, R16, R18, R20) at the N or C terminus. In other embodiments, any of SEQ ID NO: 28, 30, 32, 34, and 36 may further comprise lysine residues (e.g., K2, K4, K6, K8, K10, K12, K14, K16, K18, K20) at the N or C terminus. In other embodiments, any of the SEQ ID NO: 27-36 peptides may comprise multiple histidine residues (e.g., H2, H4, H6, H8, H12) at the N or C terminus. In other embodiments, any of the SEQ ID NO: 27-36 peptides may comprise multiple ornithine residues at the N or C terminus. In certain embodiments, the SEQ ID NO: 27-36 sequence is connected to the multiple arginine, lysine, histidine or ornithine residues by a spacer or linker molecule.

In some embodiments, the lipid compositions provided include a peptide that has comprises LLELLESL (SEQ ID NO: 1) and a peptide that comprises at least one or more sequences of PSYYRYD (SEQ ID NO: 25) and/or PSYYRGD (SEQ ID NO: 26). In some embodiments, the lipid compositions provided include a peptide that has at least 80% sequence identity to SEQ ID NO: 6 and a peptide that has at least 80% sequence identity to SEQ ID NO: 27. In other embodiments, the lipid compositions include a peptide that has at least 80% sequence identity to SEQ ID NO: 6 and a peptide that has at least 80% sequence identity to SEQ ID NO: 33. In some embodiments, the lipid compositions include a peptide selected from the peptides of SEQ ID NOs: 6-24 and a peptide selected from the peptides of SEQ ID NOs: 27-36.

In some embodiments, the endosomal release peptides and/or cell surface ligand peptides for use in the provided compositions may be linked to a glycosylphosphatidylinositol (GPI) anchor peptide, such as for example, FTLTGLLGTLVTMGLLT (SEQ ID NO: 37).

In some embodiments, the peptides described herein are attached directly to the nucleic acid binding molecule by covalent bonding, or are connected to the binding molecule via a spacer. The term "spacer," or "linker," which are used interchangeably herein, as used herein refers to a chemical structure that links two molecules to each other. In some embodiments, the spacer binds each molecule on a different part of the spacer molecule. In other embodiments, the spacer is a hydrophilic moiety and comprises about 6 to 30 carbon atoms. In other embodiments, the spacer comprises a polyether, for example $—CH_2—O—(CH_2—CH_2—O—)_iCH_2—$. In other embodiments, the spacer comprises a hydrophilic polymer, for example $[(gly)_i(ser)_j]_k$. In these formulae, i ranges from 1 to 6, j ranges from 1 to 6, and k ranges from 3 to 20. In some embodiments, the spacer is a peptide of sequence APYKAWK (SEQ ID NO: 38). In other embodiments, the spacer is a sequence that is degraded in vivo by a peptidase.

The peptides for use in the compositions provided herein are at least 10 amino acids in length. In some embodiments, the peptides are at least 10 to about 100, at least 10 to about 75, at least 10 to about 50, at least 10 to about 40, at least 10 to about 30, or at least 10 to about 20 amino acids in length. In certain embodiments, the peptides are about 15 to about 25, about 15 to about 30, about 15 to about 40, about 15 to about 50, about 15 to about 60, or about 15 to about 70 amino acids in length. In some embodiments, the peptides are about 20 to about 30, about 20 to about 40, about 20 to about 50, about 20 to about 60, about 20 to about 70, or about 20 to about 80 amino acids in length.

In some embodiments, the lipid compositions provided include a peptide, wherein peptide is at a concentration from about 0.001 to about 0.5 mg/mL. In embodiments, the peptide is at a concentration from about 0.05 mg/mL to about 0.5 mg/mL. In examples, the lipid composition includes a peptide, wherein peptide is at a concentration from about 0.001 to about 0.05 mg/mL. In examples, the lipid composition includes a peptide, wherein peptide is at a concentration from about 0.001 to about 0.1 mg/mL. In examples, the lipid composition includes a peptide, wherein peptide is at a concentration from about 0.01 to about 0.5 mg/mL. In examples, the lipid composition includes a peptide, wherein peptide is at a concentration from about 0.01 to about 0.4 mg/mL. In examples, the lipid composition includes a peptide, wherein peptide is at a concentration from about 0.01 to about 0.3 mg/mL. In examples, the lipid composition includes a peptide, wherein peptide is at a concentration from about 0.01 to about 0.2 mg/mL. In examples, the lipid composition includes a peptide, wherein peptide is at a concentration from about 0.01 to about 0.1 mg/mL. In embodiments, the peptide is at a concentration from about 0.05 mg/mL to about 0.1 mg/mL. In embodiments, the peptide is at a concentration from about 0.05 mg/mL to about 0.2 mg/mL. In embodiments, the peptide is at a concentration from about 0.05 mg/mL to about 0.3 mg/mL. In embodiments, the peptide is at a concentration from about 0.05 mg/mL to about 0.4 mg/mL. In embodiments, the peptide is at a concentration from about 0.1 mg/mL to about 0.5 mg/mL. In embodiments, the peptide is at a concentration from about 0.1 mg/mL to about 0.4 mg/mL. In embodiments, the peptide is at a concentration from about 0.1 mg/mL to about 0.3 mg/mL. In embodiments, the peptide is at a concentration from about 0.1 mg/mL to about 0.2 mg/mL.

As used herein the term "ionizable lipid" refers to a lipid having one or more functional groups that can reversibly be ionized (protonated or deprotonated) depending on the pH of the medium containing the lipid. The functional group may be basic, such as an amino function, or may be acidic, such as a carboxylic acid moiety. The skilled artisan will be aware that other ionizable functional groups also may be used. An ionizable lipid may contain both basic and acid moieties. Advantageously, an ionizable lipid carries an overall positive charge at physiological pH.

Ionizable lipids described herein refer to lipids that have at least one protonatable or deprotonatable group, such that the lipid is positively charged at a pH at or below physiological pH (e.g., pH 7.4) and neutral at a second pH, preferably at or above physiological pH. Preferably, the ionizable lipids provided herein have a pKa of the protonatable group in the range of about 4 to about 11, e.g., about 4 to about 7, e.g., between about 5 and 7, such as between about 5.5 and 6.9, when incorporated into the lipid compositions, for example, liposomes, lipid nanoparticles or other lipid complexes. Ionizable lipids include, for example amine-containing lipids that can be readily protonated.

The ionizable lipid may be selected from, for example, the group consisting of DOTMA, DOTAP, DMRIE, DC-Chol, DDAB, DOSPA, DOSPER, DOGS, TMTPS, TMTOS, TMTLS, TMTMS, TMDOS, N-1-dimethyl-N-1-(2,3-diaoleoyloxypropyl)-2-hydroxypropane-1,3-diamine, N-1-dimethyl-N-1-(2,3-diamyristyloxypropyl)-2-hydroxypropane-1,3-diamine, N-1-dimethyl-N-1-(2,3-diapalmityloxypropyl)-2-hydroxypropane-1,3-diamine, N-1-dimethyl-N-1-(2,3-diaoleoyloxypropyl)-2-(3-amino-2-hydroxypropyloxy) propane-1,3-diamine, N-1-dimethyl-N-1-(2,3-diamyristyloxypropyl)-2-(3-amino-2-hydroxypropyloxy) propane-1,3-diamine, N-1-dimethyl-N-1-(2,3-diapalmityloxypropyl)-2-(3-amino-2-hydroxypropyloxy) propane-1,3-diamine, L-spermine-5-carboxyl-3-(DL-1,2-dipalmitoyl-dimethylaminopropyl-β-hydroxyethylamine, 3,5-(N,N-di-lysyl)-diaminobenzoyl-glycyl-3-(DL-1,2-dipalmitoyl-dimethylaminopropyl-β-hydroxyethylamine), L-Lysine-bis(O,O'-oleoyl-β-hydroxyethyl)amide dihydrochloride, L-Lysine-bis-(O,O'-palmitoyl-β-hydroxyethyl) amide dihydrochloride, 1,4-bis[(3-(3-aminopropyl)-alkylamino)-2-hydroxypropyl]piperazine, L-Lysine-bis-(O,O'-myristoyl-β-hydroxyethyl)amide dihydrochloride, L-Ornithine-bis-(O,O'-myristoyl-β-hydroxyethyl)amide dihydrochloride, L-Ornithine-bis-(O,O'-oleoyl-β-hydroxyethyl)amide dihydrochloride, 1,4-bis[(3-(3-aminopropyl)-oleylamino)-2-hydroxypropyl]piperazine, L-Ornithine-bis-(O,O'-palmitoyl-β-hydroxyethyl)amide dihydrochloride, 1,4,-bis[(3-amino-2-hydroxypropyl)-oleylamino]-butane-2,3-diol, 1,4,-bis[(3-amino-2-hydroxypropyl)-palmitylamino]-butane-2,3-diol, 1,4,-bis[(3-amino-2-hydroxypropyl)-myristylamino]-butane-2,3-diol, 1,4-bis[(3-oleylamino) propyl]piperazine, L-Arginine-bis-(O,O'-oleoyl-β-hydroxyethyl)amide dihydrochloride, bis[(3-(3-aminopropyl)-myristylamino) 2-hydroxypropyl]piperazine, L-Arginine-bis-(O,O'-palmitoyl-β-hydroxyethyl)amide dihydrochloride, L-Serine-bis-(O,O'-oleoyl-β-hydroxyethyl)amide dihydrochloride, 1,4-bis[(3-(3-aminopropyl)-palmitylamino)-2-hydroxypropyl]piperazine, Glycine-bis-(O,O'-palmitoyl-β-hydroxyethyl)amide dihydrochloride, Sarcosine-bis-(O,O'-palmitoyl-β-hydroxyethyl)amide dihydrochloride, L-Histidine-bis-(O,O'-palmitoyl-β-hydroxyethyl)amide dihydrochloride, cholesteryl-3β-carboxyl-amidoethylenetrimethylammonium iodide, 1,4-bis[(3-myristylamino) propyl]piperazine, 1-dimethylamino-3-trimethylammonio-DL-2-propyl-cholesteryl carboxylate iodide, cholesteryl-3β-carboxyamidoethyleneamine, cholesteryl-3β-oxysuccinamidoethylenetrimethylammonium iodide, 1-dimethylamino-3-trimethylammonio-DL-2-propyl-cholesteryl-3β-oxysuccinate iodide, 2-[(2-trimethylammonio)-ethylmethylamino]ethyl-cholesteryl-3β-oxysuccinate iodide, 3β[N-(N',N' -dimethylaminoethane) carbamoyl] cholesterol, and 3β-[N-(polyethyleneimine)-carbamoyl] cholesterol, 1,4-bis[(3-palmitylamino) propyl]piperazine, L-Ornithylglycyl-N-(1-heptadecyloctadecyl)glycinamide, $N^2$,$N^5$-Bis(3-aminopropyl)-L-ornithylglycyl-N-(1-heptadecyloctadecyl)glycinamide, 1,4-bis[(3-(3-amino-2-hydroxypropyl)-alkylamino)-2-hydroxypropyl]piperazine $N^2$-[$N^2$,$N^5$-Bis(3-aminopropyl)-L-ornithyl]-N,N-dioctadecyl-L-glutamine, $N^2$-[$N^2$,$N^5$-Bis(aminopropyl)-L-ornithyl]-N—N-dioctadecyl-L-α-glutamine, 1,4-bis[(3-(3-amino-2-hydroxypropyl)-oleylamino)2-hydroxypropyl]piperazine, $N^2$-[$N^2$,$N^5$-Bis(aminopropyl)-L-ornithyl]-N—N-dioctadecyl-L-α-asparagine, N—[$N^2$—[$N^2$,$N^5$-Bis[(1,1-dimethylethoxy)carbonyl]-$N^2$,$N^5$-bis[3-[(1,1-dimethylethoxy)carbonyl]aminopropyl]-L-ornithyl-N—N-dioctadecyl-L-glutaminyl]-L-glutamic acid, $N^2$—[$N^2$,$N^5$-Bis(3-aminopropyl)-L-ornithyl]-N,N-diolyl-L-glutamine, $N^2$—[$N^2$,$N^5$-Bis(aminopropyl)-L-ornithyl]-N—N-dioleyl-L-α-glutamine, 4-bis[(3-(3-amino-2-hydoxypropyl)-myristylamino)-2-hydroxypropyl]piperazine, $N^2$—[$N^2$,$N^5$-Bis(aminopropyl)-L-ornithyl]-N—N-dioleyl-L-α-asparagine, N—[$N^2$—[$N^2$,$N^5$-Bis[(1,1-dimethylethoxy) carbonyl]-$N^2$,$N^5$-bis[3-[(1,1-dimethylethoxy)carbonyl] aminopropyl]-L-ornithyl-N—N-dioleyl-L-glutaminyl]-L-glutamic acid, 1,4-bis[(3-(3-aminopropyl)-oleylamino) propyl]piperazine, $N^2$—[$N^2$,$N^5$-Bis(3-aminopropyl)-L-ornithyl]-N,N-dipalmityl-L-glutamine, $N^2$—[$N^2$,$N^5$-Bis(aminopropyl)-L-ornithyl]-N—N-dipalmityl-L-α-glutamine, $N^2$—[$N^2$,$N^5$-Bis(aminopropyl)-L-ornithyl]-N—N-dipalmityl-L-α-asparagine, N—[$N^2$—[$N^2$,$N^5$-Bis[(1,1-dimethylethoxy) carbonyl]-$N^2$,$N^5$-bis[3-[(1,1-dimethylethoxy)carbonyl] aminopropyl]-L-ornithyl-N—N-dipalmityl-L-glutaminyl]-L-glutamic acid, $N^2$—[$N^2$,$N^5$-Bis(3-aminopropyl)-L-ornithyl]-N,N-dimyristyl-L-glutamine, $N^2$—[$N^2$,$N^5$-Bis (aminopropyl)-L-ornithyl]-N—N-dimyristyl-L-α-glutamine, $N^2$—[$N^2$,$N^5$-Bis(aminopropyl)-L-ornithyl]-N—N-dimyristyl-L-α-asparagine, 1,4-bis[(3-(3-amino-2-hydroxypropyl)-palmitylamino)-2-hydroxypropyl] piperazine, N—[$N^2$—[$N^2$,$N^5$-Bis[(1,1-dimethylethoxy) carbonyl]-$N^2$,$N^5$-bis[3-[(1,1-dimethylethoxy)carbonyl] aminopropyl]-L-ornithyl-N—N-dimyristyl-L-glutaminyl]-L-glutamic acid, 1,4-bis[(3-(3-aminopropyl)-myristylamino) propyl]piperazine, $N^2$—[$N^2$,$N^5$-Bis(3-aminopropyl)-L-ornithyl]-N,N-dilaureyl-L-glutamine, $N^2$—[$N^2$,$N^5$-Bis(aminopropyl)-L-ornithyl]-N—N-dilaureyl-L-α-glutamine, $N^2$—[$N^2$,$N^5$-Bis(aminopropyl)-L-ornithyl]-N—N-dilaureyl-L-α-asparagine, N—[$N^2$—[$N^2$,$N^5$-Bis[(1,1-dimethylethoxy)carbonyl]-$N^2$,$N^5$-bis[3-[(1,1-dimethylethoxy)carbonyl]aminopropyl]-L-ornithyl-N—N-dilaureyl-L-glutaminyl]-L-glutamic acid, 3-[N',N''-bis(2-tertbutyloxycarbonylaminoethyl) guanidino]-N,N-dioctadec-9-enylpropionamide, 3-[N',N''-bis(2 -tertbutyloxycarbonylaminoethyl) guanidino]-N,N-dipalmitylpropionamide, 3-[N',N''-bis(2-tertbutyloxycarbonylaminoethyl) guanidino]-N,N-dimyristylpropionamide, 1,4-bis [(3-(3-aminopropyl)-palmitylamino) propyl]piperazine, 1,4-bis[(3-(3-amino-2-hydroxypropyl)-oleylamino) propyl] piperazine, N,N-(2-hydroxy-3-aminopropyl)-N-2-hydroxypropyl-3-N,N-diolylaminopropane, N,N-(2-hydroxy-3-aminopropyl)-N-2-hydroxypropyl-3-N,N-dipalmitylaminopropane, N,N-(2-hydroxy-3-aminopropyl)-N-2-hydroxypropyl-3-N,N-dimyristylaminopropane, 1,4-bis[(3-(3-amino-2-hydoxypropyl)-myristylamino) propyl] piperazine, [(3-aminopropyl)-bis-(2-tetradecyloxyethyl)] methyl ammonium bromide, [(3-aminopropyl)-bis-(2-oleyloxyethyl)]methyl ammonium bromide, [(3-aminopropyl)-bis-(2-palmityloxyethyl)]methyl ammonium bromide, Oleoyl-2-hydroxy-3-N,N-dimethyamino propane, 2-didecanoyl-1-N,N-dimethylaminopropane, palmitoyl-2-hydroxy-3-N,N-dimethyamino propane, 1,2-dipalmitoyl-1-N,N-dimethylaminopropane, myristoyl-2-hydroxy-3-N,N-dimethyamino propane, 1,2-dimyristoyl-1-N,N-dimethylaminopropane, (3-Amino-propyl)→4-(3-amino-propylamino)-4-tetradecylcarbamoyl-butylcarbamic acid cholesteryl ester, (3-Amino-propyl)→4-(3-amino-propylamino-4-carbamoylbutylcarbamic acid cholesteryl ester, (3-Amino-propyl)→4-(3-amino-propylamino)-4-(2-dimethylamino-ethylcarbamoyl)-butylcarbamic acid cholesteryl ester, Spermine-5-carboxyglycine (N'-stearyl-N'-oleyl) amide tetratrifluoroacetic acid salt, Spermine-5-carboxyglycine (N'-stearyl-N'-elaidyl)amide tetratrifluoroacetic acid salt, Agmatinyl carboxycholesterol acetic acid salt, Spermine-5-carboxy-β-alanine cholesteryl ester tetratrifluoroacetic acid salt, 2,6-Diaminohexanoeyl β-alanine cholesteryl ester bistrifluoroacetic acid salt, 2,4-Diaminobutyroyl β-alanine cholesteryl ester bistrifluoroacetic acid salt, N,N-Bis (3-aminopropyl)-3-aminopropionyl β-alanine cholesteryl ester tristrifluoroacetic acid salt, [N,N-Bis(2-hydroxyethyl)-2-aminoethyl]aminocarboxy cholesteryl ester, Stearyl carnitine ester, Palmityl carnitine ester, Myristyl carnitine ester, Stearyl stearoyl carnitine ester chloride salt, L-Stearyl Stearoyl Carnitine Ester, Stearyl oleoyl carnitine ester chloride, Palmityl palmitoyl carnitine ester chloride, Myristyl myristoyl carnitine ester chloride, L-Myristyl myristoyl carnitine ester chloride, 1,4-bis[(3-(3-amino-2-hydroxypropyl)-palmitylamino) propyl]piperazine, N-(3-aminopropyl)-N, N'-bis-(dodecyloxyethyl)-piperazinium bromide, N-(3-aminopropyl)-N,N'-bis-(oleyloxyethyl)-piperazinium bromide, N-(3-aminopropyl)-N,N'-bis-(palmityloxyethyl)-piperazinium bromide, N-(3-aminopropyl)-N,N'-bis-(myristyloxyethyl)-piperazinium bromide, N-(3-aminopropyl)-N' -methyl-N,N'-(bis-2-dodecyloxyethyl)-piperazinium bromide, N-(3-aminopropyl)-N'-methyl-N,N'-(bis-2-oleyloxyethyl)-piperazinium bromide, N-(3-aminopropyl)-N'-methyl-N,N'-(bis-2-palmityloxyethyl)-piperazinium bromide, N-(3-aminopropyl)-N'-methyl-N,N'-(bis-2-myristyloxyethyl)-piperazinium bromide, 1,4-bis[(3-(3-aminopropyl)-oleylamino)-2-hydroxy-propyl]piperazine, 1,4-bis [(3-(3-aminopropyl)-myristylamino)-2-hydroxy-propyl] piperazine, and 1,4-bis[(3-(3-aminopropyl)-palmitylamino)-2-hydroxy-propyl]piperazine, KL22, KL25, 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA or MC3), 2,2-dilinoleyl-4-(2-dimethylaminoethyl)-[1,3]-dioxolane (DLin-KC2-DMA), 1,2-dioleyloxy-N,N-dimethylamino-propane (DODMA), 2-({8-[(3.beta.)-cholest-5-en-3-yloxy] octyl}oxy)-N,N-dimethyl-3-[(9Z,12Z)-octadeca-9,12-dien-1-yloxy]propan-1-amine (Octyl-CLinDMA), (2R)-2-({8-[(3.beta.)-cholest-5-en-3-yloxy]octyl}oxy)-N,N-dimethyl-3-[(9Z-,12Z)-octadeca-9,12-dien-1-yloxy]propan-1-amine (Octyl-CLinDMA (2R)), and (2S)-2-({8-[(3)-cholest-5-en-3-yloxy]octyl}oxy)-N,N-dimethyl-3-[(9Z,12Z)-octadeca-9,12-dien-1-yloxy]propan-1-amine (Octyl-CLinDMA (2S)).

In some embodiments, ionizable lipids described in U.S. Pat. Nos. 7,173,154, 9,856,496, and U.S. Publication No: US 2019/0060482 are contemplated for use in the present compositions and methods (wherein the reference is incorporated by reference in their entireties).

In some preferred though non-limiting embodiments, lipid compositions can include at least a first ionizable lipid and at least a first neutral lipid, wherein said lipid composition is suitable for forming a complex with a nucleic acid under aqueous conditions, wherein said the ionizable lipids have the structure of Formula (I):

(Formula (I))

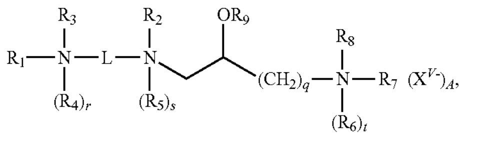

and salts thereof; where:

R1 and R2, independently, are an alkyl, alkenyl or alkynyl groups, having from 8 to 30 carbon atoms;

an alkyl, alkenyl or alkynyl groups, having from 8 to 30 carbon atoms and optionally substituted by one or more of an alcohol, an aminoalcohol, an amine, an amide, an ether, a polyether, an ester, a mercaptan, alkylthio, or a carbamoyl group or where R1 is —$(CH2)_q$-$N(R6)_tR_7R_8$;

$R_3$ and $R_4$, independently, are hydrogens, or alkyl, alkenyl or alkynyl groups having from 8 to 30 carbon atoms and optionally substituted by one or more of an alcohol, an aminoalcohol, an amine, an amide, an ether, a polyether, an ester, a mercaptan, alkylthio, or a carbamoyl group;

$R_5$-$R_8$, independently, are hydrogens, or alkyl, alkenyl or alkynyl groups;

$R_9$ is a hydrogen, or an alkyl, alkenyl or alkynyl group, a carbohydrate or a peptide;

r, s and t are 1 or 0 to indicate the presence or absence of the indicated R group, when any of r, s or t are 1 the nitrogen to which the indicated R group is attached is positively charged and wherein at least one of r, s or tis 1;

q is an integer ranging from 1 to 6, inclusive;

$X^{v-}$ is an anion, where v is the valency of the anion and A is the number of anions;

L is a divalent organic radical capable of covalently linking the two nitrogens selected from: (CH2)n, where n is an integer ranging from 1 to 10, inclusive, which is optionally substituted with one or more $ZR_{10}$ groups, where Z is O or S, and $R_{10}$ is hydrogen or an alkyl, alkenyl or alkynyl group; or $\{—(CH2)_k$-Y—$(CH_2)_m\}_p$—, where k and m, independently, are integers ranging from 1 to 10, inclusive, and p is an integer ranging from 1 to 6, inclusive, and Y is O, S, CO, COO, $CONR_{11}$, $NR_{11}CO$, or $NR_{11}COR_{11}N$ where $R_{11}$, independent of any other $R_{11}$, is hydrogen or an alkyl group;

wherein one or more $CH_2$ groups of the alkyl, alkenyl or alkynyl groups of R1-R10 can be replaced with an O, S, S—S, CO, COO, $NR_{12}CO$, $NR_{12}COO$, or $NR_{12}CONR_{12}$ where $R_{12}$, independent of any other $R_{12}$, is hydrogen or an alkyl, alkenyl or alkynyl group; and wherein the alkyl, alkenyl or alkynyl groups of $R_1$-$R_{12}$ are optionally substituted with one or more $OR_{13}$, CN, halogens, $N(R_{13})_2$, peptide, or carbohydrate groups where R13, independently of other R13, is hydrogen or an alkyl, alkenyl or alkynyl group, and wherein at least one of R3 and R4, when present as alkyl groups, are substituted with both $OR_{13}$ and $N(R_{13})_2$ groups.

The synthesis of these compounds and methods for the preparation of lipid compositions incorporating same may be achieved by any means known to those skilled in the art without limitation. Exemplary though non-limiting methods to synthesize such compounds, and methods for the formation of lipid aggregates incorporating same, may be found in, for example, U.S. Pat. No. 7,166,745 and PCT Publication No. WO 00/27795, both of which are expressly incorporated by reference in their entirety as though fully set forth herein.

In some embodiments of the present lipid aggregates, a particularly preferred though non-limiting ionizable lipid used in the formation of complexes has the structure Formula IA:

(Formula IA)

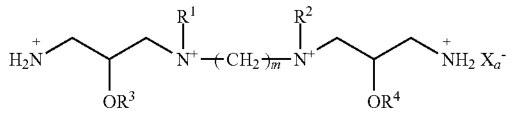

and salts thereof, wherein $R^1$ and $R^2$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ and $R^4$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; m is an integer from 1 to 6; $X_a^-$ is an anion.

In some embodiments of the present lipid aggregates, a particularly preferred though non-limiting ionizable lipid used in the formation of complexes has the structure Formula IB:

(Formula IB)

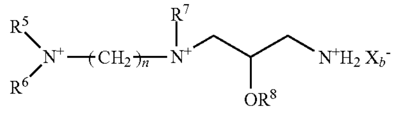

and salts thereof, wherein $R^5$ and $R^8$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^6$ and $R^7$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; n is an integer from 1 to 6; and $X_b^-$ is an anion.

In embodiments, $R^1$ and $R^2$ are independently substituted or unsubstituted alkyl. In embodiments, $R^1$ and $R^2$ are independently unsubstituted alkyl. $R^1$ and $R^2$ are independently unsubstituted $C_1$-$C_{20}$ alkyl. In embodiments, $R^1$ and $R^2$ are independently unsubstituted $C_5$-$C_{20}$ alkyl. In embodiments, $R^1$ and $R^2$ are independently unsubstituted $C_{10}$-$C_{20}$ alkyl. In embodiments, $R^1$ and $R^2$ are independently unsubstituted $C_{12}$-$C_{18}$ alkyl. In embodiments, $R^1$ and $R^2$ are independently unsubstituted $C_{14}$-$C_{16}$ alkyl. In embodiments, $R^1$ is unsubstituted $C_{14}$ alkyl. In embodiments, $R^2$ is unsubstituted $C_{14}$ alkyl. In embodiments, $R^1$ is unsubstituted $C_{15}$ alkyl. In embodiments, $R^2$ is unsubstituted $C_{15}$ alkyl. In embodiments, $R^1$ is unsubstituted $C_{16}$ alkyl. In embodiments, $R^2$ is unsubstituted $C_{16}$ alkyl. In embodiments, $R^1$ is $—(CH_2)_{13}CH_3$. In embodiments, $R^2$ is $—(CH_2)_{13}CH_3$.

In embodiments, $R^3$ and $R^4$ are independently hydrogen or substituted or unsubstituted alkyl. In embodiments, $R^3$ and $R^4$ are independently hydrogen.

In embodiments, $R^5$, $R^6$ and $R^7$ are independently hydrogen, substituted or unsubstituted alkyl. In embodiments, $R^5$, $R^6$ and $R^7$ are independently hydrogen or unsubstituted alkyl. In embodiments, $R^5$, $R^6$ and $R^7$ are independently hydrogen or unsubstituted $C_1$-$C_{20}$ alkyl. In embodiments, $R^5$, $R^6$ and $R^7$ are independently hydrogen or unsubstituted $C_5$-$C_{20}$ alkyl. In embodiments, $R^5$, $R^6$ and $R^7$ are independently hydrogen or unsubstituted $C_{10}$-$C_{20}$ alkyl. In embodiments, $R^5$, $R^6$ and $R^7$ are independently hydrogen or unsubstituted $C_{12}$-$C_{18}$ alkyl. In embodiments, $R^5$, $R^6$ and $R^7$ are independently hydrogen or unsubstituted $C_{14}$-$C_{16}$ alkyl. In embodiments, $R^5$, $R^6$ and $R^7$ are independently hydrogen or unsubstituted $C_{14}$ alkyl. In embodiments, $R^5$, $R^6$ and $R^7$ are independently hydrogen or unsubstituted $C_{15}$ alkyl. In embodiments, $R^5$, $R^6$ and $R^7$ are independently hydrogen or unsubstituted $C_{16}$ alkyl. In embodiments, $R^5$ is unsubstituted $C_{14}$ alkyl. In embodiments, $R^7$ is unsubstituted $C_{14}$ alkyl. In embodiments, $R^5$ is $—(CH_2)_{13}CH_3$. In embodiments, $R^6$ is hydrogen. In embodiments, $R^7$ is $—(CH_2)_{13}CH_3$.

In embodiments, $R^8$ is hydrogen or substituted or unsubstituted alkyl. In embodiments, $R^8$ is hydrogen.

In embodiments, m is an integer from about 1 to 6. In embodiments, m is an integer from about 1 to 5. In embodiments, m is an integer from about 1 to 4. In embodiments, m is an integer from about 1 to 3. In embodiments, m is an integer from 1 to 6. In embodiments, m is an integer from 1 to 5. In embodiments, m is an integer from 1 to 4. In embodiments, m is an integer from 1 to 3. In embodiments, m is 1. In embodiments, m is 2. In embodiments, m is 3. In embodiments, m is 4. In embodiments, m is 5. In embodiments, m is 6.

In embodiments, n is an integer from about 1 to 6. In embodiments, n is an integer from about 1 to 5. In embodiments, n is an integer from about 1 to 4. In embodiments, n is an integer from about 1 to 3. In embodiments, n is an integer from 1 to 6. In embodiments, n is an integer from 1 to 5. In embodiments, n is an integer from 1 to 4. In embodiments, n is an integer from 1 to 3. In embodiments, n is 1. In embodiments, n is 2. In embodiments, n is 3. In embodiments, n is 4. In embodiments, n is 5. In embodiments, n is 6.

In one embodiment, $R^1$ is $—(CH_2)_{13}CH_3$, $R^2$ is $—(CH_2)_{13}CH_3$, $R^3$ is hydrogen, $R^4$ is hydrogen, m is 4 and $X_a$ is $CH_3COO^-$.

In one embodiment, $R^5$ is $—(CH_2)_{13}CH_3$, $R^6$ is hydrogen, $R^7$ is $—(CH_2)_{13}CH_3$, $R^8$ is hydrogen, n is 4 and $X_b^-$ is $CH_3COO^-$.

Examples of compounds of Formula I structure for use as an ionizable lipid in the provided lipid compositions and methods include, without limitation, the following:

Compound 1-1

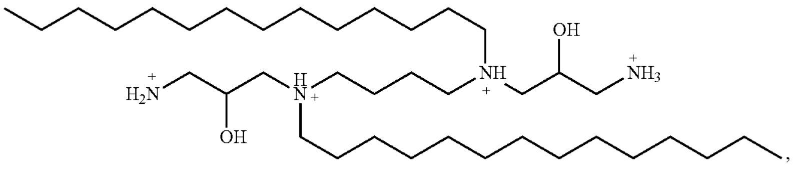

,

Compound 1-2

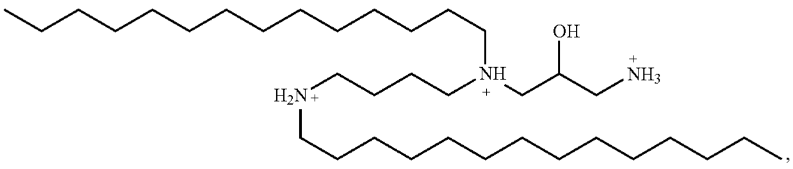

,

Compound 1-3

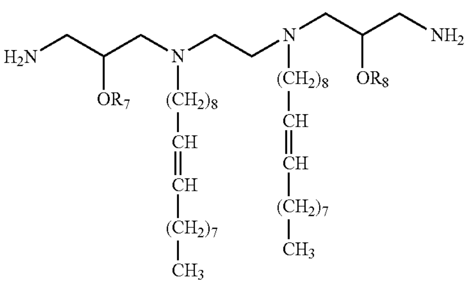

Compound 1-4

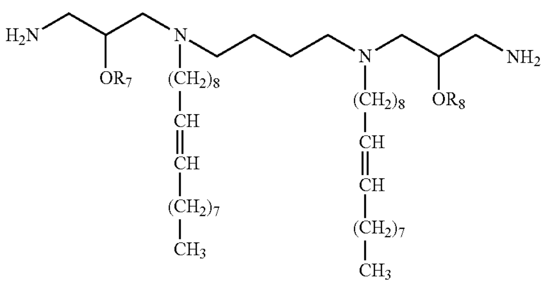

-continued

Compound 1-5

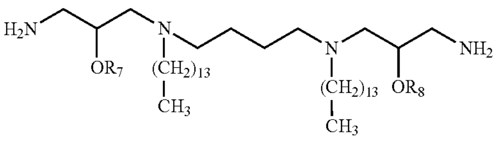

and

Compound 1-6

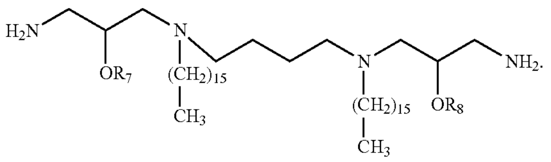

In some embodiments, ionizable lipids described in U.S. Pat. Nos. 9,259,475 and 10,883,118 are contemplated for use in the present compositions and methods (wherein the references are incorporated by reference in their entirety). In some embodiments, such lipids are based on a core of N,N'-disubstituted 2,3-hihydroxy-1,4-butanediamine.

In some non-limiting embodiments, the lipid composition comprises a ionizable diaminobutane lipid molecule having the structure of Formula II:

(Formula II)

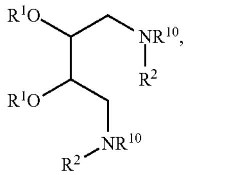

and salts thereof, where each $R^1$ independently is $C_1$-$C_{23}$ alkyl, $C_1$-$C_{23}$ alkenyl, —(CO)$C_1$-$C_{23}$ alkyl, or —(CO)$C_1$-$C_{23}$ alkenyl; and each $R^2$ independently is —$CH_2$—$(CHR_3)_{1-6}$—$CH_2$—$NHR^4$ or —$CH_2$—$(CHR_3)_{0-6}$—$CH_2$—OH, where each $R^3$ independently is H, OH, or $NH_2$, $R^4$ is H or $CH_3$; and $R^{10}$ is H or $C_1$-$C_8$ alkyl.

In one embodiment, $R^1$ may be $C_{14}$-$C_{20}$ alkyl or monounsaturated $C_{14}$-$C_{20}$-alkenyl. In this and other embodiments, $R^2$ may be —$CH_2$—$(CHR_3)_{1-6}$—$CH_2$—$NHR^4$ and $R^3$ is H or OH. In some embodiments, no more than 3 $R^3$ groups are OH in each $R^3$ moiety.

In any of these embodiments, each $R^1$ may be the same or different, and each $R^2$ may be the same or different. In specific embodiments, one or both $R^{10}$ may be H, or one or both $R^{10}$ may be $C_1$-$C_3$ alkyl, for example, one or both $R^{10}$ may be methyl.

In particular embodiment above, one or both $R^1$ may be $C_{12}$-$C_{20}$ alkenyl, and the alkenyl moieties may be cis alkenyl.

In specific embodiments, one or both $R^2$ may be —$CH_2$—CHOH—$(CHR^3)_{0-5}$—$CH_2$—$NHR^4$; for example one or both $R^2$ may be —$CH_2$—CHOH—$CH_2$—$NH_2$. In these compounds R advantageously is $C_{14-18}$ alkyl or $C_{14-18}$ monounsaturated alkenyl.

Each $R^1$, $R^2$ and/or each $R^{10}$ may be the same or different and thus the molecule may be symmetrical or non-symmetrical. In particular embodiments, $R^2$ may be $C_1$-$C_3$ alkyl and/or $R^1$ is monounsaturated $C_{12}$-$C_{20}$ alkenyl. One or both $C_{12}$-$C_{20}$ alkenyl moieties in R1, when present, may be cis alkenyl.

Also provided are molecules having the structure Formula IIA:

(Formula IIA)

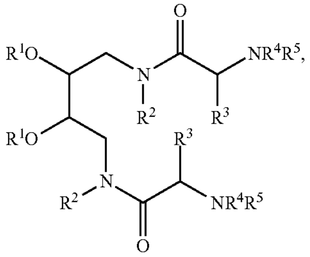

and salts thereof.

In this structure, each $R^1$ independently may be $C_1$-$C_{23}$ alkyl, $C_1$-$C_{23}$ alkenyl, —(CO)$C_1$-$C_{23}$ alkyl, or —(CO)$C_1$-$C_{23}$ alkenyl. Each R2 independently may be $C_1$-$C_6$ alkyl, or $C_1$-$C_6$ alkenyl, optionally interrupted by up to 2 O atoms. Each $R^3$ independently may be H, $C_1$-$C_6$ alkyl, $C_1$-$C_6$ alkenyl, $C_2$-$C_6$ alkynyl, $C_3$-$C_7$cycloalkyl, $C_3$-$C_7$cycloalkyl-$C_1$-$C_6$ alkyl, $C_5$-$C_7$-cycloalkenyl, $C_5$-$C_7$-cycloalkenyl-$C_1$-$C_6$ alkyl, —$(CH_2)_m NR^6(CH_2)_n NHR^7$, —$(CH_2)_{2-6}NHR^7$, —$(CH_2)_{3-6}$NHC(=NH)$NH_2$, $((CH_2)_m O_x)_y(CH_2)_2 O_x R^8$, or —$(CH_2)_{0-3}$Het. Each $R^4$ independently may be H, $C_1$-$C_6$ alkyl, or $C_1$-$C_6$ alkenyl and each $R^5$ independently may be H, an amine protecting group, —$(CH_2)_m NR^6(CH_2)_n NHR^7$, —$(CH_2)_{2-6}NHR^7$, —$(CH_2)_{3-6}$NHC(=NH)$NH_2$, —(CO)$C_1$-$C_{23}$ alkyl, —(CO)$C_1$-$C_{23}$ alkenyl, or a peptide containing 1-20 amino acid residues. The peptide advantageously contains multiple positively charged amino acid side chains. Thus, for example, the peptide may contain one or more lysine, arginine, and/or histidine residues. Other positively charged amino acids also may be used, whether or not naturally occurring. Thus, for example, ornithine, homoarginine and other amino acids containing amine, guanidine; imidazole and other basic heterocycles and the like can be used. Each m independently may be 2-5, and each n independently may be 2-5, while each x independently may be 0 or 1, each y may be 0-2, and each z may be 1-6. R6 and $R^7$ independently may be H, an amine protecting group, —(CO)$C_1$-$C_{23}$ alkyl, or —(CO)$C_1$-$C_{23}$ alkenyl, R8 may be H, $C_1$-$C_6$ alkyl, or $C_1$-$C_6$ alkenyl, and Het may be a 5-7 membered monocyclic basic heterocycle, or an 8-11 membered bicyclic basic heterocycle.

The molecule of structure Formula IIA may be symmetrical or non-symmetrical with regard to each or all of the substituents $R^1$-$R^5$ independently; that is each $R^1$ may be the same or different, each $R^2$ may be the same or different, each $R^3$ may be the same or different, each R4 may be the same or different, and/or each $R^5$ may be the same or different.

In specific embodiments of structure Formula IIA, $R^2$ may be $C_1$-$C_3$ alkyl and/or $R^1$ may be monounsaturated $C_{12}$-$C_{20}$ alkenyl; for example one or both $C_{12}$-$C_{20}$ alkenyl moieties in $R^1$ may be cis alkenyl.

In other embodiments of Formula II, $R^3$ may be —$(CH_2)_m NR^6(CH_2)_n NHR^7$ and/or $R^5$ may be —$(CH_2)_{2-6}NHR^7$. In these or other embodiments, m may be 3, n may be 3, and/or $R^5$ may be —$(CH_2)_3NHR^7$. In these and other embodiments, each $R^6$ and each $R^7$ may be H.

In still other embodiments of Formula II, at least one $R^6$ or $R^7$ may be —$(CO)C_1$-$C_{23}$ alkyl, or —$(CO)C_1$-$C_{23}$ alkenyl and the remainder are H. In a specific embodiment, each $R^1$ may be $C_{12}$-$C_{20}$ alkyl or $C_{12}$-$C_{20}$ monounsaturated alkenyl, each $R^2$ may be $C_1$-$C_3$ alkyl, each $R^3$ may be —$(CH_2)_3NH(CH_2)_3NH_2$, each $R^4$ may be H; and each $R^5$ may be —$(CH_2)_3NH_2$. In another specific embodiment, each $R^1$ may be $C_{12}$-$C_{20}$ alkyl or $C_{12}$-$C_{20}$ monounsaturated alkenyl, each $R^2$ may be $C_1$-$C_3$ alkyl, each $R^3$ may be —$(CH_2)_3NR^6(CH_2)_3NHR^7$, each $R^4$ may be H; each $R^5$ may be —$(CH_2)_3NHR^7$, and at least one $R^6$ or $R^7$ may be —$(CO)C_1$-$C_{23}$ alkyl, or —$(CO)C_1$-$C_{23}$ alkenyl and the remainder are H.

Specific examples of compounds of structure Formula II include compounds having the structure:

(Formula IIB)

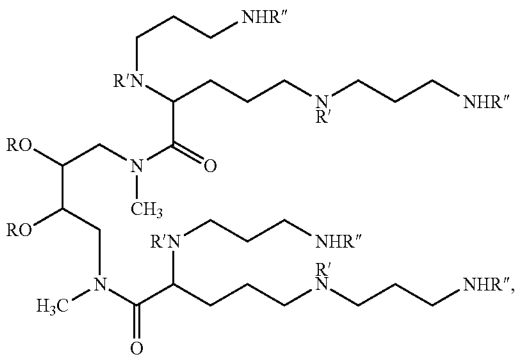

and salts thereof, where each R for example may be, but is not limited to, $C_{12-20}$ alkyl or $C_{12-20}$ alkenyl; and each R' and each R" independently may be, but is not limited to, H, an amine protecting group, —$(CO)C_1$-$C_{23}$ alkyl, or —$(CO)C_1$-$C_{23}$ alkenyl.

In these and other embodiments of structure (Formula IIB), R may be $C_{14}$-$C_{18}$ alkyl or $C_{14}$-$C_{18}$ alkenyl, and/or each R' and each R" independently may be H, $C_{14}$-$C_{18}$ alkyl or $C_{14}$-$C_{18}$ alkenyl.

Another specific example of the compounds of structure Formula II is the set of compounds having the structure:

(Formula IIC)

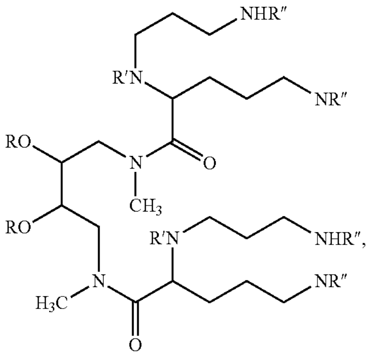

and salts thereof, where, for example, R may be, but is not limited to, $C_{12-20}$ alkenyl; and/or each R' and each R" independently may be, but is not limited to, H, an amine protecting group, —$(CO)C_1$-$C_{23}$ alkyl, or —$(CO)C_1$-$C_{23}$ alkenyl.

In these and other embodiments R may be oleyl and each R' and each R" independently may be H, or oleoyl. In still other embodiments at least one R' or R" may be oleoyl and the remainder are H.

In still other specific embodiments of structure (II), each $R^3$ independently may be —$(CH_2)_{2-6}NHR^7$, —$(CH_2)_{3-6}NHC(=NH)NH_2$, or —$(CH_2)_{1-3}$Het, each $R^4$ is H and each $R^5$ independently is H or a peptide containing 1-20 amino acid residues.

In these and other embodiments, each $R^1$ may be $C_{12}$-$C_{20}$ alkyl or $C_{12}$-$C_{20}$ alkenyl, each $R^2$ may be $C_1$-$C_3$ alkyl, and/or and each $R^5$ may be H. In still other embodiments, each $R^3$ may be —$(CH_2)_{2-6}NH_2$, —$(CH_2)_{3-6}NHC(=NH)NH_2$ or each $R^3$ may be —$(CH_2)_{1-3}$Het. In one specific embodiment, Het may be

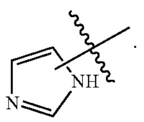

In some embodiments of the present lipid compositions, a non-limiting ionizable lipid used in the composition may be compounds having the following Formula II structures, where R is $C_{14}$, $C_{16}$, or $C_{18}$ alkyl, or $C_{14}$, $C_{16}$, or $C_{18}$ monounsaturated alkenyl:

Compound 2-1

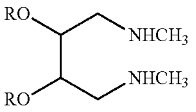

Compound 2-2

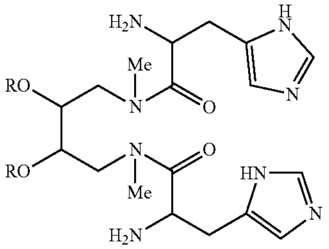

Compound 2-3

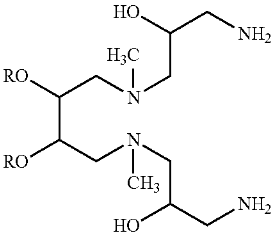

-continued

Compound 2-4

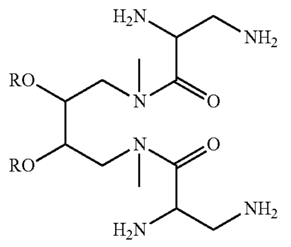

Compound 2-5

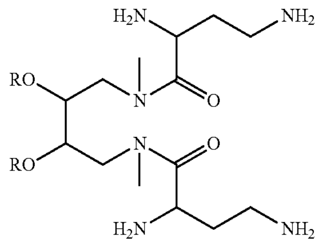

Compound 2-6

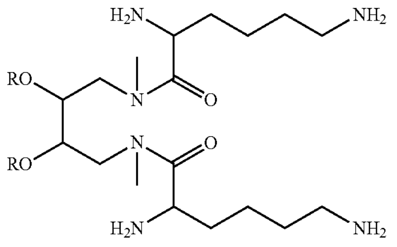

Compound 2-7

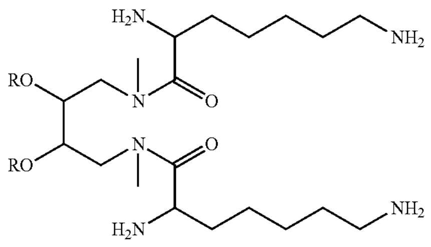

Compound 2-8

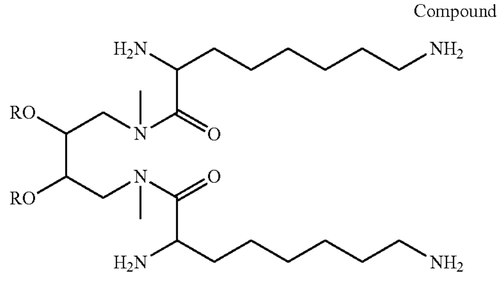

Compound 2-9

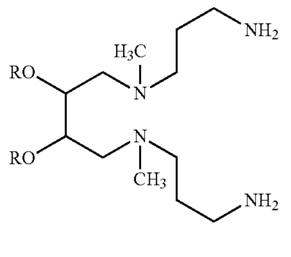

and

-continued

Compound 2-10

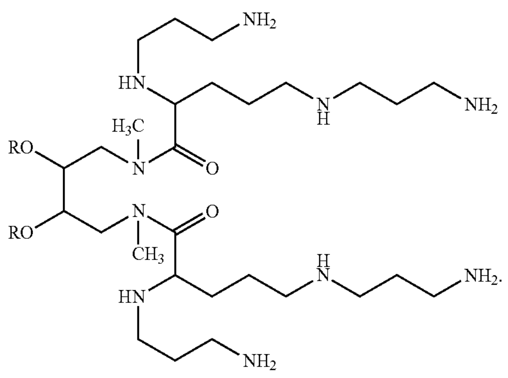

In some embodiments, lipids described in U.S. Pat. No. 8,759,499 are contemplated for use in the present compositions and methods (the contents of which is incorporated herein by reference in its entirety).

In some non-limiting embodiments, the lipid compositions can include at least a first ionizable lipid and optionally at least a first neutral lipid, wherein said lipid composition is suitable for forming a complex with a nucleic acid under aqueous conditions, wherein said the ionizable lipids have the structure of Formula III:

(Formula III)

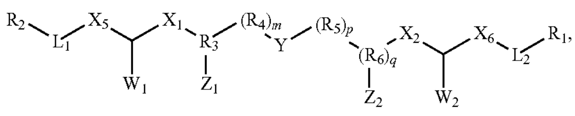

and salts thereof.

In compounds of Formula III, $X_1$ and $X_2$ may independently be selected from the group consisting of $(CH_2)_n$, $(CHOH)_n$, and CONH. $X_5$ and $X_6$ independently may be $(CH_2)_{1-6}$. $W_1$ and $W_2$ independently may be selected from the group consisting of, hydrogen, —OH, —O—($C_1$-$C_{30}$) alkyl, —O—($C_1$-$C_{30}$)alkenyl, —O—($C_1$-$C_{30}$)alkynyl, —$NH_2$, —$NH(CH_2)SCH_3$, —$N((CH_2)SCH_3)$, —SH, and —NH—$NH_2$. $R^3$ and $R^6$ independently may be selected from the group consisting of N, NH, CH, $N(CH_2)_sCH_3$, $(CH)_n$, $(COH)_n$, CON— and q=0-1. $R^4$ and $R^5$ independently may be selected from the group consisting of $(CH_2)_n$, $(CH_2$—CHOH—$CH_2)_n$, (CHOH)—, HNCO, CONH, CO, —O—, —S—, —S—S—, polyamide and an ester linkage. $L_1$ and $L_2$ independently may be selected from the group consisting of —NH—, —O—, —NHCO—, —CONH—, —OCO—, —COO—, —CO—, —S—, —S—S—, —NHC(O)O—, —OC(O)NH—, —NHCONH—, —NHC(=NH)NH—, —S(O)— and —$SO_2$—.

Y is a heterocyclic moiety containing at least one amine or amide moiety. The points of attachment of Y may be carbon and/or heteroatoms. Examples of suitable heterocyclic moieties include, but are not limited to, piperazine, piperidine, pyridine, pyrrolidine, and imidazole moieties and derivatives thereof. In specific embodiments, the heterocyclic moiety is a piperazine ring, where the points of attachment optionally are at one or both of the nitrogen atoms. The heterocyclic moiety may optionally be substituted with up to 4 substituents independently selected from the group consisting of OH, =O, a carboxylic acid, an ether, a polyether, an alkylaryl, an amino alcohol, an amide, an straight chain alkyl, branched alkyl, cycloalkyl, straight chain alkenyl, branched alkenyl, cycloalkenyl, straight chain alkynyl, branched alkynyl, primary alkylamine, secondary alkylamine, tertiary alkyl amine, quaternary alkylamine, alkenylamine, secondary alkenylamine, tertiary alkenyl amine, quaternary alkenylamine, alkynylamine, secondary alkynylamine, tertiary alkynylamine, quaternary alkynylamine, amino alcohol, alcohol, ether, polyether, aryl, benzyl, heterocycle, cycloalkyl, alkyl polyamine, alkenyl polyamine, alkynyl polyamine, spermidine, spermine, carboxy spermine, guanidinium, pyridinium, pyrollidinium, piperidinium, piperazinium, and amino acyl, where the alkyl, alkenyl, alkynyl and alkylamine groups are optionally substituted with at least one hydroxyl, or at least one amine, or at least one hydroxyl and at least one amine, $R_1$ and $R_2$ independently may be selected from the group consisting of hydrogen, primary alkylamine, secondary alkylamine, tertiary alkyl amine, quaternary alkylamine, alkenylamine, secondary alkenylamine, tertiary alkenyl amine, quaternary alkenylamine, alkynylamine, secondary alkynylamine, tertiary alkynylamine, quaternary alkynylamine amino alcohol, alkyl polyamine, alkenyl polyamine, alkynyl polyamine, spermidine, spermine, carboxy spermine, guanidinium, pyridinium, pyrollidinium, piperidinium, piperazinium, amino acyl, peptidyl, and protein. In the context of the present invention it will be understood that, unless specifically indicated otherwise, an alkylamine can be an amine containing a short or a long alkyl chain. Similarly, an alkenylamine will be understood to contain a short or long alkenyl chain, and the same is true for alkynylamines.

$Z_1$ and $Z_2$ independently may be selected from the group consisting of straight chain alkyl, branched alkyl, cycloalkyl, straight chain alkenyl, branched alkenyl, cycloalkenyl, straight chain alkynyl, branched alkynyl where m, n, p, and s independently are 0-6, with the proviso that when m, n, and p all are 0 then Y is eliminated and $R_3$ is bonded directly to $X_2$.

Y may have the following cyclic structure

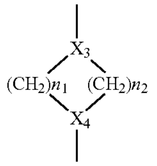

where $X_3$ and $X_4$ may independently be selected from N and CH and $n_1$ and $n_2$ independently are 1-10. Typically, Y is a 6-9 membered ring and, in exemplary specific embodiments, $X_3$ and $X_4$ are both N and $n_1$ and $n_2$ are both 2, i.e. Y is an optionally substituted piperazine moiety. This structure may optionally be substituted with 1-4 moieties as described above for Y.

In other specific embodiments Y can have the following cyclic structure:

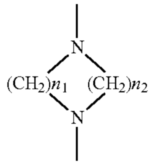

where $n_1$, and $n_2$ independently are 1-10. Typically, $n_1+n_2$ is 3-7. Such a cyclic structure may optionally be substituted with 1-4 moieties independently selected as described above for Y.

Examples of the lipids may be defined by the following structure, where $L_1$ and $L_2$ both are NH and $X_5$ and $X_6$ are $CH_2$:

(Formula IIIA)

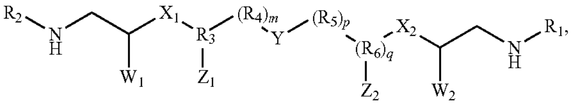

(Formula IIIA), and salts thereof.

In this structure $R_1$-$R_6$, $W_1$, $W_2$, $X_1$, $X_2$, $Z_1$, $Z_2$, Y, m, p, and q are as defined above.

A specific example of Formula IIIA structure for use as an ionizable lipid in the provided compositions and methods include 1,4-Bis[(3-(3-aminopropyl)-oleoylamino)-2-hydroxypropyl]piperazine, where $R_1$, $R_2$=H; $X_1$, $X_2$=$CH_2$; $R_4$, $R_5$=$CH_2$—CHOH—$CH_2$; $R_3$, $R_6$=N; $Z_1$, $Z_2$-oleoyl; $W_1$, $W_2$=H; q, p, m=1; and Y-piperazine. Other examples include ((Bis(3-{N-3-aminopropyl-N-palmityl}amino-2-hydroxypropyl)-piperazine)) and other compounds with alkyl groups varying in length from C12 to C18 including, but not limited to, compounds where $R_1$, $R_2$=H; $X_1$, $X_2$=$CH_2$; $R_4$, $R_5$=$CH_2$—CHOH—$CH_2$; $R_3$, $R_6$=N; $W_1$, $W_2$=H; q, p, m=1; Y-piperazine; and $Z_1$ and $Z_2$ both are palmityl, myristyl, lauryl, or stearyl.

Other specific examples of compounds of Formula III structure for use herein include, but are not limited to, the following:

Compound 3-1: $R_1$, $R_2$=H; $X_1$, $X_2$=$CH_2$; $R_4$, $R_5$=$CH_2$; —CHOH—$CH_2$; $R_3$, $R_6$=N; $Z_1$, $Z_2$=palmityl; $W_1$, $W_2$=H; q, p, m=1; and Y=piperazine;

Compound 3-2: R1, R2=H; X1, X2=CH2; R4, R5=CH2-CHOH—CH2; R3, R6=N; Z1, Z2=myristyl; W1, W2=H; q, p, m=1; and Y=piperazine;

Compound 3-3: R1, R2=H; X1, X2=CH2; R4, R5=CH2-CHOH—CH2; R3, R6=N; Z1, Z2=lauryl; W1, W2=H; q, p, m=1; and Y=piperazine;

Compound 3-4: R1, R2=H; X1, X2=CH2; R4, R5=CH2-CHOH—CH2; R3, R6=N; Z1, Z2=stearyl; W1, W2=H; q, p, m=1; and Y=piperazine;

Compound 3-5: R1, R2=H; X1, X2=CH2; R4, R5=CH2-CHOH—CH2; R3, R6=N; Z1, Z2=oleoyl; W1, W2=OH; q, p, m=1; and Y=piperazine;

Compound 3-6: R1, R2=H; X1, X2=CH2; R4, R5=CH2-CHOH—CH2; R3, R6=N; Z1, Z2-palmityl; W1, W2=OH; q, p, m=1; and Y-piperazine;

Compound 3-7: R1, R2=H; X1, X2=CH2; R4, R5=CH2-CHOH—CH2; R3, R6=N; Z1, Z2=myristyl; W1, W2=OH; q, p, m=1; and Y-piperazine;

Compound 3-8: R1, R2=H; X1, X2=CH2; R4, R5=CH2-CHOH—CH2; R3, R6=N; Z1, Z2=lauryl; W1, W2=OH; q, p, m=1; and Y=piperazine;

Compound 3-9: R1, R2=H; X1, X2=CH2; R4, R5=CH2-CHOH—CH2; R3, R6=N; Z1, Z2=stearyl; W1, W2=OH; q, p, m=1; and Y=piperazine;

Compound 3-10: R1, R2=H; X1, X2=CH2; R4, R5=CH2-CH2-CH2; R3, R6=N; Z1, Z2=oleoyl; W1, W2=H; q, p, m=1; and Y=piperazine;

Compound 3-11: R1, R2=H; X1, X2=CH2; R4, R5=CH2-CH2-CH2; R3, R6=N; Z1, Z2=palmityl; W1, W2=H; q, p, m=1; and Y=piperazine;

Compound 3-12: R1, R2=H; X1, X2=CH2; R4, R5-CH2-CH2-CH2; R3, R6=N; Z1, Z2=myristyl; W1, W2=H; q, p, m=1; and Y=piperazine;

Compound 3-13: R1, R2=H; X1, X2=CH2; R4, R5-CH2-CH2-CH2; R3, R6=N; Z1, Z2=lauryl; W1, W2=H; q, p, m=1; and Y=piperazine;

Compound 3-14: R1, R2=H; X1, X2=CH2; R4, R5=CH2-CH2-CH2; R3, R6=N; Z1, Z2=stearyl; W1, W2=H; q, p, m=1; and Y=piperazine;

Compound 3-15: R1, R2=H; X1, X2-CH2; R4, R5=CH2-CH2-CH2; R3, R6=N; Z1, Z2=oleoyl; W1, W2=OH; q, p, m=1; and Y-piperazine:

Compound 3-16: R1, R2=H; X1, X2=CH2; R4, R5=CH2-CH2-CH2; R3, R6=N; Z1, Z2=palmityl; W1, W2=OH; q, p, m=1; and Y=piperazine;

Compound 3-17: R1, R2=H; X1, X2=CH2; R4, $R^5$=CH2-CH2-CH2; R3, R6=N; Z1, Z2=myristyl; W1, W2=OH; q, p, m=1; and Y=piperazine;

Compound 3-18: R1, R2=H; X1, X2=CH2; R4, R5=CH2-CH2-CH2; R3, R6=N; Z1, Z2=lauryl; W1, W2=OH; q, p, m=1; and Y=piperazine;

Compound 3-19: R1, R2=H; X1, X2=CH2; R4, $R^5$=CH2-CH2-CH2; R3, R6=N; Z1, Z2=stearyl; W1, W2=OH; q, p, m=1; and Y-piperazine.

In the context of the lipids provided, a short chain alkyl group is typically, unless otherwise defined, $C_1$-$C_6$ alkyl. A long chain alkyl group is typically, unless otherwise defined, $C_{10}$-$C_{20}$ alkyl, or $C_{10}$-$C_{30}$ alkyl. When not specifically defined, either definition may be used, as appropriate. The skilled artisan also will appreciate that other derivative groups containing alkyl moieties, for example, alkoxy moieties and the like, also may contain short and/or long chain groups as appropriate in the context, unless otherwise defined. An alkenyl group contains at least one cis or trans carbon-carbon double bond and typically is $C_{10}$-$C_{30}$ in chain length. Exemplary alkenyl groups contain one or two cis double bonds where the double bonds are disubstituted. An alkynyl group contains at least one carbon-carbon triple bond and typically is $C_{10}$-$C_{30}$ in chain length. The alkyl, alkenyl or alkynyl groups may be straight chain or branched. The skilled artisan also will appreciate that other derivative groups containing alkyl moieties, for example, alkoxy moieties and the like, also may contain short and/or long chain groups as appropriate in the context, unless otherwise defined.

In some non-limiting embodiments, ionizable lipids contemplated for use in the present compositions and methods include lipid molecules having the structure of Formula IV:

(Formula IV)

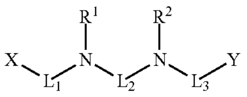

and salts thereof.

In this structure $L_1$ and $L_3$ independently are absent or independently may be: —$CO_q$—, $C_3$-$C_8$ alkyl optionally interrupted by N, O or —C(O)O—; monounsaturated $C_4$-$C_8$ alkenyl, —$CO_qC_3$-$C_8$ alkyl optionally interrupted by N, O or —C(O)O—; and —$CO_q$-monounsaturated $C_4$-$C_8$ alkenyl; where q is 1 or 2; or when $R^1$ and $R^2$ are not H then $L_1$X and $L_3$Y independently may be —$CR^3$=$C(R^4)R^5$. $L_2$ is $C_4$-$C_{12}$ alkylene, optionally substituted at up to 2 positions by $OR^9$.

X and Y independently may be selected from:

$L_4$-Het, where $L_4$ is $C_1$-$C_4$ alkylene and Het is a $C_4$-$C_{12}$ heterocycle containing at least one nitrogen atom;

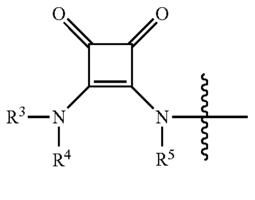

and

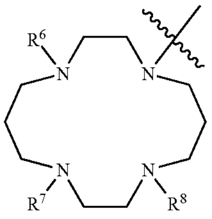

$R^1$ and $R^2$ independently may be H, $C_8$-$C_{20}$ alkyl, or monounsaturated $C_8$-$C_{20}$ alkenyl. $R^3$-$R^8$ independently may be selected from H, $C_1$-$C_6$ alkyl, and $C_3$-$C_6$ cycloalkyl. In specific examples, $R^3$-$R^8$ independently are H or $C_1$-$C_3$ alkyl.

$R^9$ may be H, —CO—$C_8$-$C_{20}$ alkyl, —CO-monounsaturated $C_8$-$C_{20}$ alkenyl, $C_8$-$C_{20}$ alkyl or monounsaturated $C_8$-$C_{20}$ alkenyl. Specific examples include: where $R^9$ is $C_{14}$-$C_{18}$ alkyl or monounsaturated alkenyl; where $R^9$ is H and $R^1$ and $R^2$ are not H; where $R^9$ is not H and $R^1$ and $R^2$ are H; and where $R^9$ is $C_{14}$-$C_{18}$ alkyl or —CO—$C_{14}$-$C_{18}$ alkyl and $R^1$ and $R^2$ are H. Advantageously, the double bond in $R^9$, when present, is a cis double bond. In these molecules X and Y may be the same or different, $L_1$ and $L_3$ independently may be the same or different, and $R^1$ and $R^2$ may be the same or different.

In particular embodiments, $L_2$ may be $C_4$-$C_{12}$ alkylene. In other embodiments, $L_2$ is advantageously —$(CH_2)_mCHOR^9(CH_2)_nCHOR^9(CH_2)_p$—, where m, and p are 1-6 and n is 0-6, and wherein m+n+p=2-8. In a specific example, $L_2$ is —$CH_2CH(OR^9)CH(OR^9)CH_2$—.

In further embodiments, the molecules may contain heterocyclic moieties linked via an amide or carbamate linkage, where $L_1$ is —CO— or —$CO_2$— and X is $L_4$Het, where Het is a heterocyclic ring as defined below. In still further embodiments, when $R^1$ and/or $R^2$ are not H, the molecules may contain enamine moieties, in which $L_1$X is —$CR^5$=$C(R^3)R^4$. In such enamine moieties R3 and R5 may together form a $C_3$-$C_7$ carbocyclic ring.

The molecule of structure Formula IV may be symmetrical or non-symmetrical with regard to each or all of the substituents $R^1$, $R^2$, $L_{2-3}$ and X and Y independently; that is each $R^1$ may be the same or different, each $R^2$ may be the same or different, $L_1$ and $L_3$ may be the same or different $R^3$, and X and Y may be the same or different. In addition, the structure of $L_2$ need not be symmetrical.

Specific examples of compounds of Formula IV structure for use herein include:
Compound 4-1
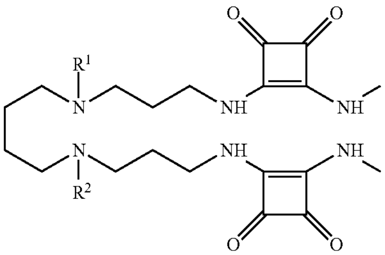
Compound 4-2
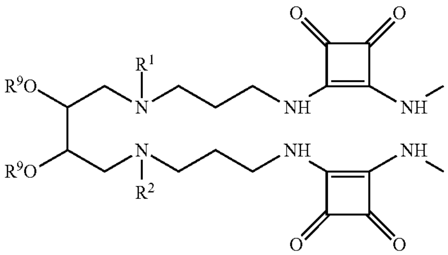
Compound 4-3
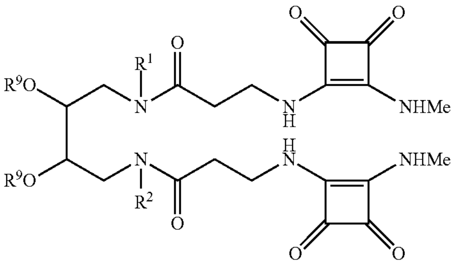
Compound 4-4
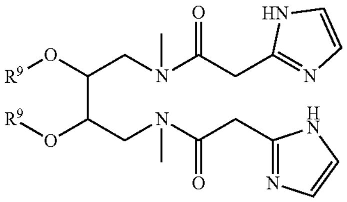
Compound 4-5
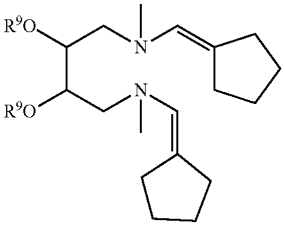
Compound 4-6
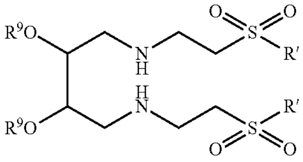
R′ = C-C6 Alkyl, alkenyl
Compound 4-4
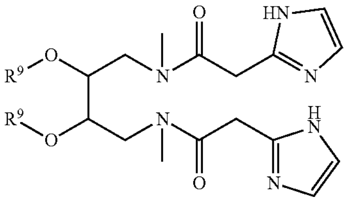
Compound 4-7
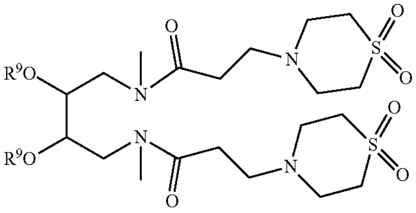
Compound 4-8
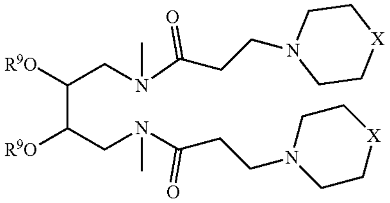
X = NH, S, O
Compound 4-9
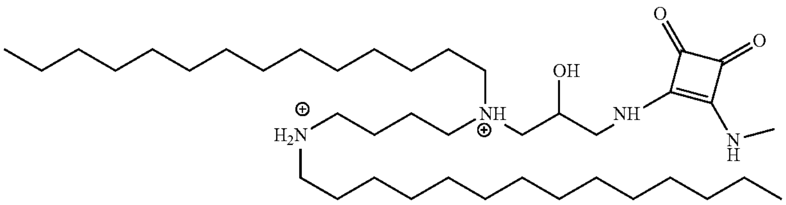

-continued
Compound 4-10
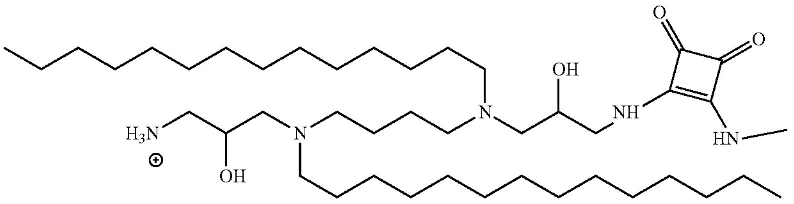
Compound 4-11
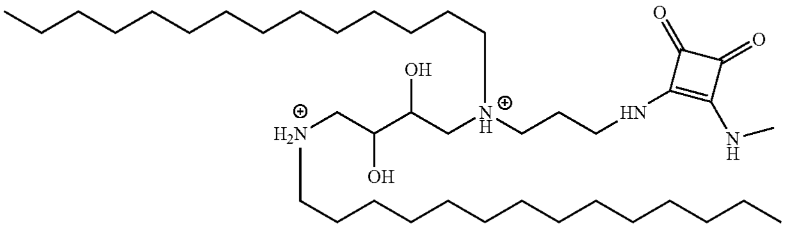
Compound 4-12
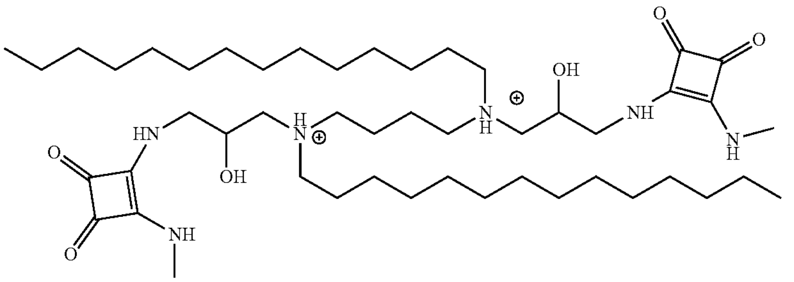
Compouns 4-13
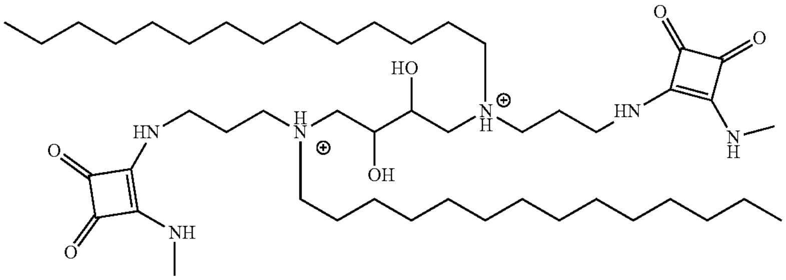
and
Compound 4-14
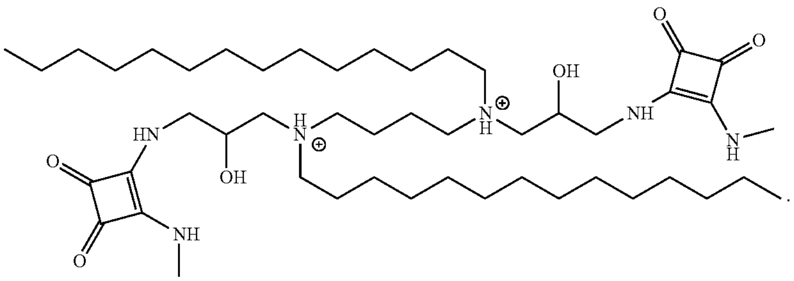
.

In these molecules each $R^1$ or $R^2$ for example may be, but is not limited to, $C_{14-18}$ alkyl or $C_{14-18}$ alkenyl; and each $R^9$ independently may be, but is not limited to, H, —(CO)$C_{14}$-$C_{18}$ alkyl, or —(CO)$C_{14}$-$C_{18}$ alkenyl.

In some embodiments, lipids described in U.S. Pat. No. 8,034,977 are contemplated for use in the present compositions and methods (the contents of which is incorporated herein by reference in its entirety).

In some non-limiting embodiments, the lipid compositions can include at least a first ionizable lipid and optionally at least a first neutral lipid, wherein said lipid composition is suitable for forming a complex with a nucleic acid under aqueous conditions, wherein said the ionizable lipids have the structure of Formula (V):

(Formula V)

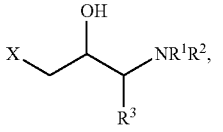

or salts thereof, wherein X is N(R4R5R6) or dialkylphophatidyl, or X is

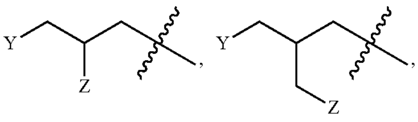

, or

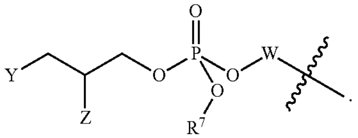

In structure Formula V, Y and Z independently may be selected from the group consisting of alkoxy, alkanoyloxy, alkylamine, alkyl urethane and alkyl guanidine. $R^1$ and $R^2$ independently may be selected from the group consisting of hydrogen, $C_1$-$C_6$ alkyl, $C_1$-$C_6$ alkylamine, alkylaminoalcohol, spermiyl, spermidyl and carboxyspermiyl. $R^3$ is H or $C_1$-$C_4$ alkyl. $R^4$, $R^5$, and $R^6$ independently are selected from the group consisting of hydrogen, alkyl, alkenyl, aryl, and alkylaryl, provided that at least one of $R^4$, $R^5$, and $R^6$ is a long chain alkyl or alkenyl. The alkyl, alkenyl, aryl, and alkylaryl groups may contain, for example, 6 to 30 carbon atoms, advantageously 10 to 18 carbon atoms, although the skilled artisan will recognize that the groups may contain fewer than 6 or more than 30 carbon atoms. W may be short chain ($C_1$-$C_6$)alkyl or alkylamino, and $R^7$ may be a negative charge or short chain ($C_1$-$C_6$)alkyl.

Example of the compounds of structure Formula V is the set of compounds having the structure Formula VA:

(Formula VA)

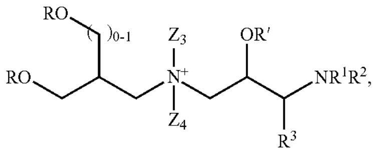

and salts thereof, wherein each R independently is $C_1$-$C_{30}$ alkyl, alkenyl or alkanoyl;

$Z_3$ and Z4 are independently $C_1$-$C_6$ alkyl;

$R^1$ and $R^2$ independently are selected from the group consisting of hydrogen, $C_1$-$C_6$ alkyl, alkylamine, alkylaminoalcohol, spermiyl, spermidyl and carboxyspermiyl, $R^3$ is H or $C_1$-$C_4$ alkyl, and R' is H or

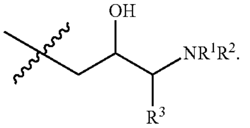

Specific examples of alkyaminoalcohol lipids of Formula VA include, without limitation, Compound 5-1

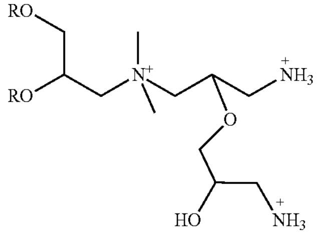

and

Compound 5-2

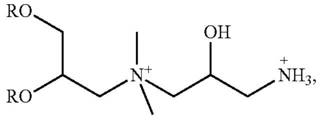

wherein each R independently is $C_{10}$-$C_{18}$ alkyl or alkenyl.

In some embodiments, additional ionizable lipids contemplated for use in the present compositions and methods are provided below (compounds X-1 to X-16) and any others from FIGS. 1 and 2 of Han et al (2021); "An ionizable lipid toolbox for RNA delivery; vol. 12, page 7233; incorporated by reference in its entirety.

Compound X-1
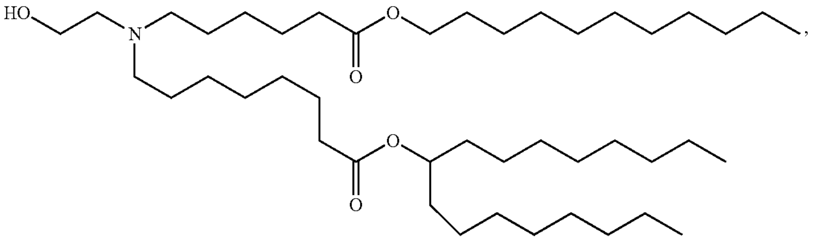
Compound X-2
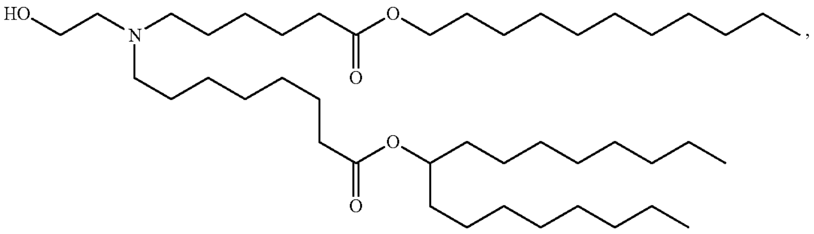
Compound X-3
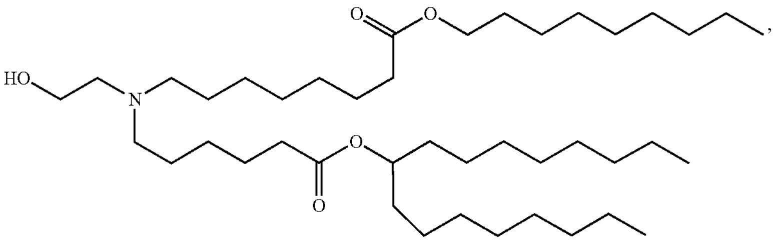
Compound X-4
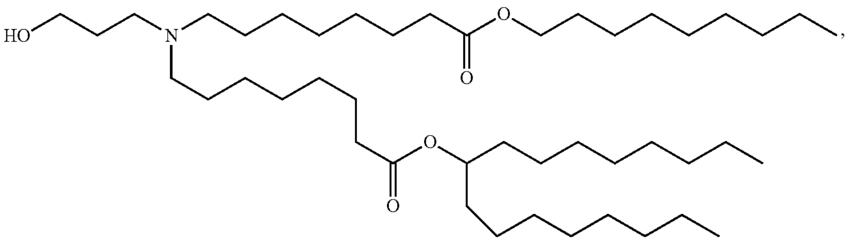
Compound X-5
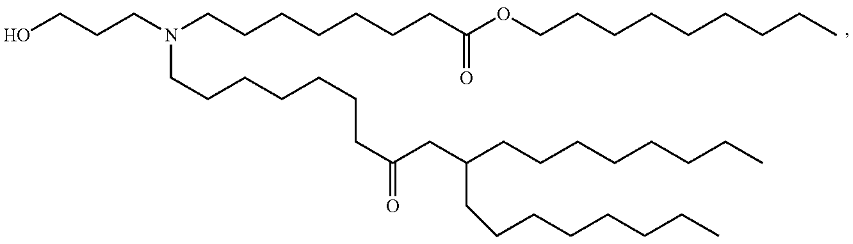
Compound X-6
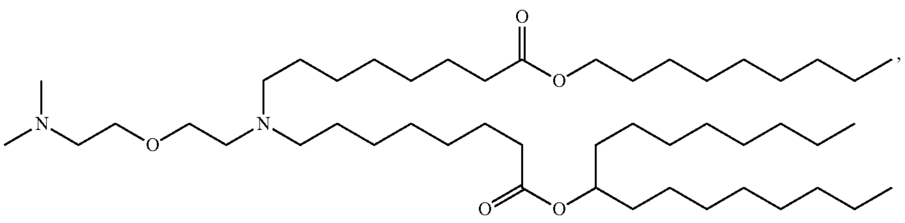

-continued
Compound X-7
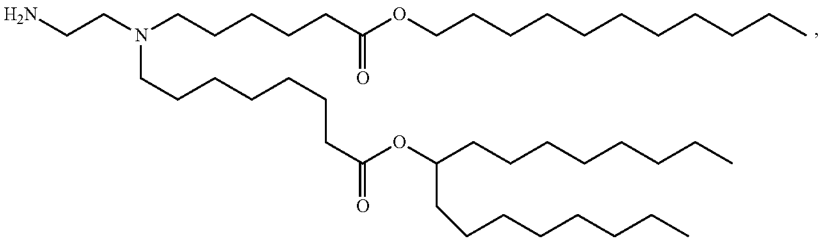
Compound X-8
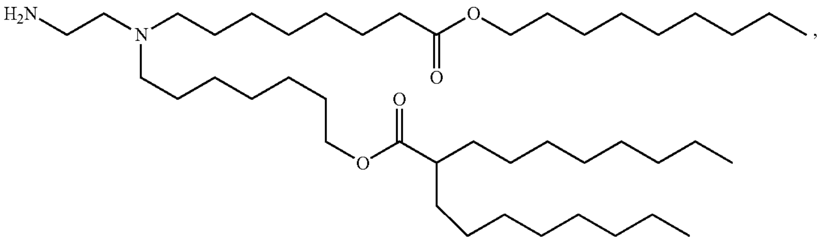
Compound X-9
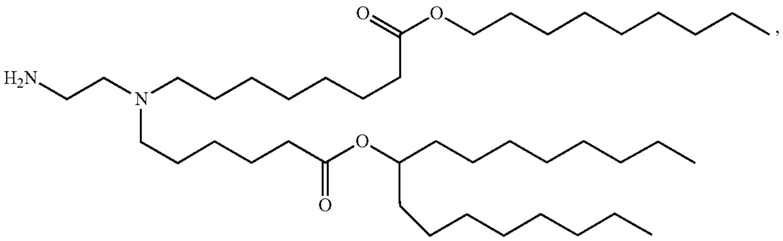
Compound X-10
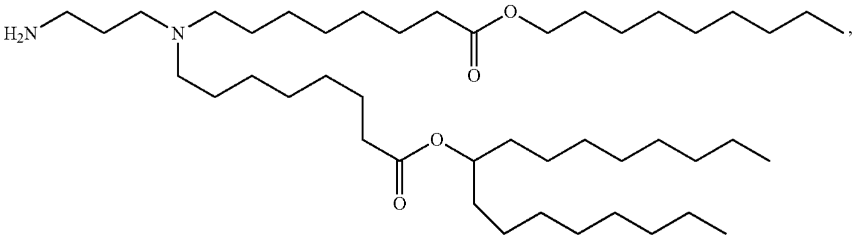
Compound X-11
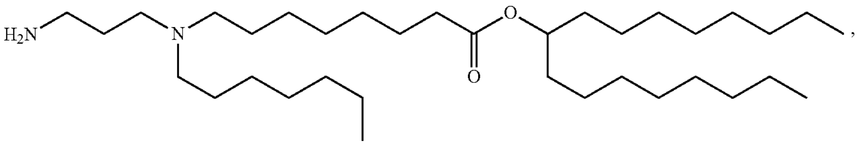
Compound X-12
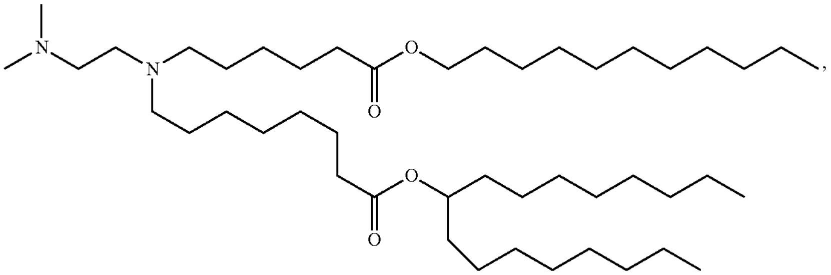

-continued

Compound X-13

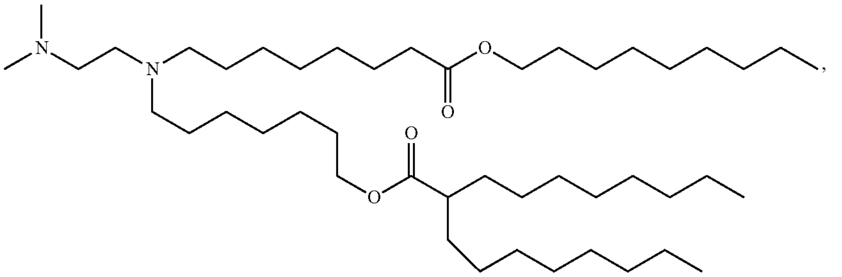

Compound X-14

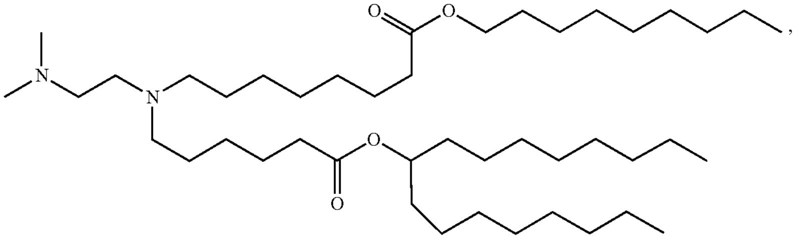

Compound X-15

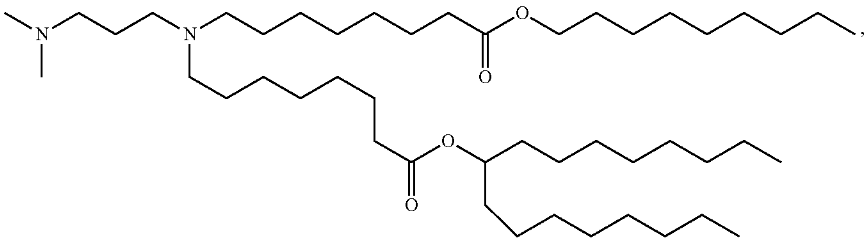

and

Compound X-16

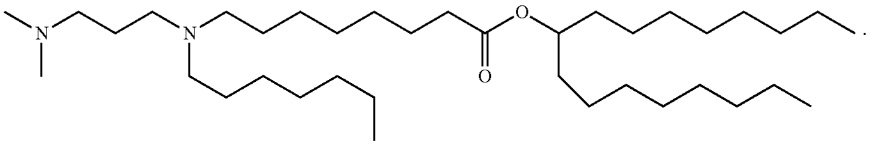

The central amine moieties of a lipid according to Formula (I), (IA), (IB), (II), (IIA), (IIB), (IIC), (III), (IIIA), (IV), (V) or the other N-containing lipid structures depicted herein may be protonated at a physiological pH. Thus, the lipid may have a positive or partial positive charge at physiological pH.

The skilled artisan will recognize that, although some of the ionizable lipid molecules are shown here for convenience in their neutral (unprotonated) forms, these molecules will exist in a partially or fully protonated form in solutions of appropriate pH, and that the present invention encompasses the molecules in all their protonated, unprotonated, ionized and non-ionized forms without limitation, unless specifically indicated otherwise.

Advantageously, in addition to the ionizable lipids, the lipid compositions include one or more neutral co-lipids, although the skilled artisan will recognize that other co-lipids may be used. The neutral lipid may be, for example, selected from the group consisting of a sterol or sterol derivative, a phospholipid, or a combination thereof.

The neutral lipid can be present at about 5-60 mol % of the overall lipid formulation. In some embodiments, neutral lipid(s) are present from about 15-50 mol %, e.g., 25-40 mol %. In certain embodiments, the amount of the neutral lipid in the lipid composition disclosed herein is at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 mol % of the overall lipid formulation.

In some embodiments, the lipid composition includes a neutral lipid, and the neutral lipid includes cholesterol. In some embodiments, the neutral lipid includes sterol. In some embodiments, the neutral lipid includes dioleoylphosphatidylethanolamine (DOPE). In some embodiments, the neutral lipid includes diphytanoylphosphatidylethanolamine (DPhPE). In some embodiments, the neutral lipid includes Lyso-PE (1-acyl-2-hydroxy-sn-glycero-3-phosphoethanolamine). In some embodiments, the neutral lipid includes Lyso-PC (1-acyl-3-hydroxy-sn-glycero-3-phosphocholine). In some embodiments, the neutral lipid includes distearoylphosphatidylcholine (DSPC). In some embodiments, the neutral lipid includes dioleoylphosphatidylcholine (DOPC). In some embodiments, the neutral lipid includes dipalmitoylphosphatidylcholine (DPPC). In some embodiments, the neutral lipid includes palmitoyloleoylphosphatidylcholine (POPC). In some embodiments, the neutral lipid includes palmitoyloleoyl-phosphatidylethanolamine (POPE) and dioleoyl-phosphatidylethanolamine 4 -(N-maleimidomethyl)-cyclohexane-1-carboxylate (DOPE-mal). In some embodiments, the neutral lipid includes dipalmitoyl phosphatidyl ethanolamine (DPPE). In some embodiments, the neutral lipid includes dimyristoylphosphoethanolamine (DMPE). In some embodiments, the neutral lipid includes distearoyl-phosphatidylethanolamine (DSPE). In some embodiments, the neutral lipid includes 16-O-monomethyl PE. In some embodiments, the neutral lipid includes 16-O-dimethyl PE. In some embodiments, the neutral lipid includes 18-1-trans PE. In some embodiments, the neutral lipid includes 1-stearoyl-2-oleoyl-phosphatidyethanol amine (SOPE). In some embodiments, the neutral lipid includes 1,2-dioleoyl-sn-glycero-3-phophoethanolamine (trans DOPE). In some embodiments, the neutral lipid includes any combinations thereof.

Exemplary phospholipids useful in the compositions disclosed herein include, but are not limited to, dioleoylphosphoethanolamine (DOPE), diphytanolphosphatidylethanolamine (DPhPE), Lyso-PE (1-acyl-2-hydroxy-sn-glycero-3-phosphoethanolamine), Lyso-PC (1-acyl-3-hydroxy-sn-glycero-3-phosphocholine), distearoylphosphatidylcholine (DSPC), dioleoylphosphatidylcholine (DOPC), dipalmitoylphosphatidylcholine (DPPC), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanolamine (SOPE), 1,2-dioleoyl-sn-glycero-3-phophoethanolamine (trans DOPE), 1-stearoyl-2-oleoyl-phosphatidylcholine (SOPC), dilinoleoylphosphocholine (DLPC), dimyristoylphosphocholine (DMPC), diundecanoylphosphocholine (DUPC), dioleoylphosphatidylglycerol (DOPG), dipalmitoylphosphatidylglycerol (DPPG), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, sphingomyelin, phosphatidylcholine, phosphatidylethanolamine, phosphatidylserine, phosphatidylinositol, phosphatidic acid, palmitoyloleoyl phosphatidylcholine, lysophosphatidylcholine, and lysophosphatidylethanolamine (LPE), or any combination thereof.

Phospholipids useful in the compositions provided herein can be present, for example at about 5 mol % to about 20 mol % of the lipid composition formulation. Advantageously, phospholipids are present at a range from about 1 mol % to about 40 mol %, e.g., from 1 mol % to about 25 mol %. Preferably, the amount of the phospholipid in the lipid composition formulations disclosed herein is at least about 0.5 mol %, 1 mol %, 2 mol %, 3 mol %, 4 mol %, 5 mol %, 6 mol %, 7 mol %, 8 mol %, 9 mol %, 10 mol %, 12 mol %, 14 mol %, 16 mol %, 18 mol %, or 20 mol %, or any amount in between, of the overall lipid composition formulations.

In some embodiments, the phospholipids useful in the composition can be present from about 5 mol % to about 15 mol %. In some embodiments, the phospholipids useful in the composition can be present from about 5 mol % to about 10 mol %. In some embodiments, the phospholipids useful in the composition can be present from about 5 mol % to about 12 mol %. In some embodiments, the phospholipids useful in the composition can be present from about 1 mol % to about 35 mol %. In some embodiments, the phospholipids useful in the composition can be present from about 1 mol % to about 30 mol %. In some embodiments, the phospholipids useful in the composition can be present from about 1 mol % to about 25 mol %. In some embodiments, the phospholipids useful in the composition can be present from about 1 mol % to about 20 mol %. In some embodiments, the phospholipids useful in the composition can be present from about 1 mol % to about 15 mol %. In some embodiments, the phospholipids useful in the composition can be present from about 1 mol % to about 10 mol %. In some embodiments, the phospholipids useful in the composition can be present from about 1 mol % to about 5 mol %.

In some embodiments, the amount of the phospholipid in the lipid composition formulations disclosed herein is at least about 0.5 mol %. In some embodiments, the amount of the phospholipid in the lipid composition formulations disclosed herein is at least about 1 mol %. In some embodiments, the amount of the phospholipid in the lipid composition formulations disclosed herein is at least about 2 mol %. In some embodiments, the amount of the phospholipid in the lipid composition formulations disclosed herein is at least about 3 mol %. In some embodiments, the amount of the phospholipid in the lipid composition formulations disclosed herein is at least about 4 mol %. In some embodiments, the amount of the phospholipid in the lipid composition formulations disclosed herein is at least about 5 mol %. In some embodiments, the amount of the phospholipid in the lipid composition formulations disclosed herein is at least about 10 mol %. In some embodiments, the amount of the phospholipid in the lipid composition formulations disclosed herein is at least about 12 mol %. In some embodiments, the amount of the phospholipid in the lipid composition formulations disclosed herein is at least about 15 mol %. In some embodiments, the amount of the phospholipid in the lipid composition formulations disclosed herein is at least about 16 mol %. In some embodiments, the amount of the phospholipid in the lipid composition formulations disclosed herein is at least about 17 mol %. In some embodiments, the amount of the phospholipid in the lipid composition formulations disclosed herein is at least about 18 mol %. In some embodiments, the amount of the phospholipid in the lipid composition formulations disclosed herein is at least about 19 mol %. In some embodiments, the amount of the phospholipid in the lipid composition formulations disclosed herein is at least about 20 mol %.

Other neutral lipids that can be advantageously included in the lipid composition formulations provided herein include sterols, or lipids containing sterol moieties ("sterol derivatives"). As defined herein, "sterols" are a subgroup of steroids consisting of steroid alcohols. Exemplary sterols and lipids containing sterol moieties useful in the lipid composition formulations provided herein include, but are not limited to cholesterol, fecosterol, sitosterol, ergosterol, campesterol, stigmasterol, brassicasterol, tomatidine, tomatine, ursolic acid, alpha-tocopherol, hopanoids, phytosterols, steroids, and mixtures thereof. In some embodiments, the structural lipid is a sterol. Some lipid composition formulations provided herein include a sterol or sterol derivative. The sterols or sterol derivatives can be present at about 5-60 mol % of the overall lipid composition formulation. Advantageously, the sterol or sterol derivatives are present from about 15-50 mol %, e.g., 25-40 mol %. Preferably, the amount of the sterol (such as cholesterol) or sterol derivative in the lipid composition disclosed herein is at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 mol % of the overall lipid formulation. Some lipid composition formulations provided herein do not include a sterol or sterol derivative.

The lipid complex compositions (e.g., lipid nanoparticles, liposomes and lipoplexes) provided herein can also include one or more compounds and/or compositions comprising cationic polymers such as polyethyleneimine (PEI), polymers of positively charged amino acids such as polylysine, polyornithine, and polyarginine, polyamidoamine, poly (beta-amino esters), oligoalkylamines, positively charged dendrimers and fractured dendrimers, cationic β-cyclodextrin containing polymers (CD-polymers), DEAE-dextran and the like. The lipid complex compositions may include linear PEIs, branched PEIs, and/or derivatives or modified forms thereof, such as cyclodextrin-PEI, stearic acid-PEI, aromatic-PEI, histidinyl-PEI, and PEI-PEG. Linear PEI, branched PEI, and derivatives thereof are commercially available at a variety of molecular weights.

The lipid complex compositions (e.g., lipid nanoparticles, liposomes and lipoplexes) provided herein can also be combined with one or more exosomes, or biological materials (e.g., lipids, proteins, nucleic acids, or the like) derived or purified from exosomes.

The term "exosome" refers to the small membrane vesicles secreted by most cells that contain cell specific payloads of proteins, lipids and, genetic material and other biomolecules that are transported to other cells in different location of the tissue. Exosomes can be considered liposomal particles. Exosomes or lipid mixtures obtained therefrom, can be used in combination with other transfection agents or helper lipid mixtures. Exosomes are also referred to as microvesicles, epididimosomes, argosomes, exosome-like vesicles, microparticles, promininosomes, prostasomes, dexosomes, texosomes, archeosomes and oncosomes.

Examples of lipid constituents isolated from exosomes include, but are not limited to, Lyso-PC (non-limiting examples of which C-18, C-16, C-14 and mixture), Lyso-bisphospahtidic acid (non-limiting example of which is C-18, C-16 and C-14), sphingomyelin, ceramides (non-limiting examples C-8-C-24), disaturated PC (non-limiting examples DSPC, DPPC, DMPC and others where Cn (n=8-25)), diunsaturated PC-MIX (non-limiting examples of which are DOPC, DP(db)PC) phosphatidyl serine (PS), phosphatidyl inositol (PI)), disaturated PE non-limiting example, DSPE, DPPE, DMPE), di-unsaturated PE-MIX (non-limiting example DOPE DP(db)PE), phosphatidyl glycerol (PG) (non-limiting examples of which are C-18-C-22), cholesterol, and diglycerides, such as cardiolipin.

Also contemplated are any mixtures of combination of the above listed ionizable lipids, neutral lipids, cationic polymers, exosomes, and/or lipid mixtures isolated from exosomes.

The lipid compositions provided herein can also include a stabilizing agent, such as a stabilizing lipid. Stabilizing lipids can be neutral lipids, or they can be charged. Stabilizing lipids that can advantageously be used in the formulations provided herein include, but are not limited to, polyethylene glycol (PEG)-modified lipids. Non-limiting examples of PEG-lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG-DMPE, PEG-DPPC, or a PEG-DSPE lipid. Other stabilizing lipids useful in the compositions disclosed herein include, e.g., polyglycol lipids, yoxyethylene alkyl ethers, diblock polyoxyethylene ether co-polymers, triblock polyoxyethylene alkyl ethers co-polymers, and amphiphilic branched polymers. In embodiments, stabilizing agent can be In polyoxyethylene (20) oleyl ether, polyoxyethylene (23) lauryl ether, polyoxyethylene (40) stearate ("Myrj52"), poly(propylene glycol) 11-block-poly (ethylene glycol) 16-block-poly(propylene glycol) 11, poly (propylene glycol) 12-block-poly(ethylene glycol) 28-block-poly(propylene glycol) 12, polysorbate 80 (also known as Tween 80, IUPAC name 2-[2-[3,4-bis(2-hydroxyethoxy)oxolan-2-yl]-2-(2-hydroxyethoxy) ethoxy]ethyl octadec-9-enoate), Myrj52 (Polyoxyethylene (40) stearate), Brij™ S10 (Polyoxyethylene (10) stearyl ether), BRIJ™ LA-Polyoxyethylene (4) lauryl ether; BRIJ™ S20=Polyoxyethylene (20) stearyl ether; BRIJ™ S35=Polyoxyethylene (23) lauryl ether; TPGS 1000=D-α-Tocopherol polyethylene glycol 1000 succinate; Tween 20/Polysorbate 80/Tridecyl-D-maltoside in equal ratios, and combinations thereof. In certain compositions, the stabilizing agent is present at about 0.1-5 mol % of the lipid composition. For example, in some compositions, the stabilizing agent is present at about 0.5 mol %, 1 mol %, 1.5 mol %, 2 mol %, 2.5 mol %, 3 mol %, 3.5 mol %, 4 mol %, 4.5 mol %, 5 mol %, or any value in between, of the lipid composition. In other examples, the stabilizing agent is present at about 0.5 mol % to about 5 mol % of the lipid composition. In other examples, the stabilizing agent is present at about 0.5 mol % to about 4 mol % of the lipid composition. In other examples, the stabilizing agent is present at about 0.5 mol % to about 3 mol % of the lipid composition. In other examples, the stabilizing agent is present at about 0.5 mol % to about 2 mol % of the lipid composition. In other examples, the stabilizing agent is present at about 0.5 mol % to about 1 mol % of the lipid composition. In other examples, the stabilizing agent is present at about 1 mol % to about 5 mol % of the lipid composition. In other examples, the stabilizing agent is present at about 1 mol % to about 4 mol % of the lipid composition. In other examples, the stabilizing agent is present at about 1 mol % to about 3 mol % of the lipid composition. In other examples, the stabilizing agent is present at about 1 mol % to about 2 mol % of the lipid composition.

In some embodiments of the payload-containing lipid composition, payload is complexed to the exterior of the lipid complex (e.g., liposomes, lipid nanoparticles). In some embodiments of the nucleic acid-containing lipid composition, nucleic acid is complexed to the exterior of the lipid complex (e.g., liposomes, lipid nanoparticles). In some embodiments, the compositions have from about 20% to about 50% of the nucleic acid complexed to the exterior of the lipid complex. In other embodiments, the compositions have about 20%, about 30%, about 40%, about 50%, about 60%, about 70%, or about 80% of the nucleic acid complexed to the exterior of the lipid complex. Exterior complexation of a nucleic acid can be measured by methods know in the art, such as in Blakney et al. (2019) Gene Therapy 26:363-372.

In some embodiments of the payload-containing lipid composition, payload is complexed on the interior of the lipid complex (e.g., liposomes, lipid nanoparticles). In some embodiments of the nucleic acid-containing lipid composition, nucleic acid is complexed on the interior of the lipid complex (e.g., liposomes, lipid nanoparticles). In some embodiments, the compositions have an encapsulation efficiency from about 75% to about 95%, or from about 85% to about 90%. In some examples, the encapsulation efficiency is from about 75% to about 100%. In some examples, the encapsulation efficiency is from about 75% to about 95%. In some examples, the encapsulation efficiency is from about 75% to about 90%. In some examples, the encapsulation efficiency is from about 75% to about 85%. In some examples, the encapsulation efficiency is from about 75% to about 80%. In some examples, the encapsulation efficiency is from about 80% to about 95%. In some examples, the encapsulation efficiency is from about 80% to about 90%. In some examples, the encapsulation efficiency is from about 80% to about 85%.

The encapsulation efficiency (EE %) can be measured using a fluorescence plate-based assay employing the RiboGreen reagent. This assay measures the quantity of mRNA in samples with intact LNPs to determine the quantity of unencapsulated RNA as well as in LNP samples disrupted by triton X-100 to measure the total RNA. The % of encapsulation efficiency was calculated as the difference between the total RNA and the unencapsulated RNA divided by the total RNA.

The efficiency of encapsulation of a therapeutic and/or prophylactic describes the amount of therapeutic and/or prophylactic that is encapsulated or otherwise associated with a lipid composition after preparation, relative to the initial amount provided. In some embodiments, the encapsulation efficiency is desirably high (e.g., close to 100%). The encapsulation efficiency may be measured, for example, by comparing the amount of therapeutic and/or prophylactic in a solution containing the lipid complex composition before and after breaking up the lipid complex composition with one or more organic solvents or detergents. Fluorescence may be used to measure the amount of free therapeutic and/or prophylactic (e.g., RNA) in a solution. In some embodiments for the lipid compositions described herein, the encapsulation efficiency of a therapeutic and/or prophylactic may be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency may be at least 80%. In certain embodiments, the encapsulation efficiency may be at least 90%.

Methods of Inducing an Immune Response

Provided herein are methods for inducing an immune response in a subject including administering to a subject the lipid composition described herein. In some embodiments, the lipid composition includes at least one ionizable lipid having a charge (N), at least one peptide, wherein the peptide comprises LLELLESL (SEQ ID NO: 6), and a nucleic acid molecule comprising a charge (P), wherein the composition comprises an N/P ratio of 0.01 to 5.0, or from 0.01 to 0.2, or from 0.05 to 0.5, or from 0.1 to 1.0, or from 0.5 to 2.0, or from 1.0 to 5.0. In some embodiments, the lipid composition includes at least one ionizable lipid having a charge (N), at least one peptide, wherein the peptide comprises at least 80% sequence identity to GLFEALLELLESLWELLLEA (SEQ ID NO: 6), and a nucleic acid molecule comprising a charge (P), wherein the composition comprises an N/P ratio of 0.01, 0.02, 0.04, 0.06, 0.08, 0.1, 0.12, 0.14, 0.16, 0.18, or 0.2. In other embodiments, the lipid composition comprises an N/P ratio of 0.4, 0.6, 0.8, 1.0, 2.0, 3.0, 4.0, 5.0, 6.0, 7.0 or 8.0. In some embodiments, the lipid composition comprises an N/P ratio from 0.01 to 1.0, from 0.5 to 2.0, or from 1.0 to 8.0. In some embodiments, the administered lipid composition further comprises at least one neutral lipid. In some embodiments, the administered lipid composition further comprises a transfection enhancing agent, such as a peptide comprising SEQ ID NO: 25 and/or SEQ ID NO: 26.

In some examples, administering the composition includes systemic administration or local administration. For example, the local administration includes intramuscular administration, or subcutaneous administration. In some embodiments, the administration includes administration to the brain, spinal cord, eye (e.g., intravitreal administration), or lymph node (e.g., intranodal administration) of a subject. In other examples, administration can include ex vivo administration, wherein immune cells (e.g., dendritic cells) are targeted ex vivo. In examples, the subject is a mammalian subject.

Also provided herein are methods for delivering a lipid composition to an immune cell of a subject, where the method includes administering the lipid composition described herein. In some embodiments, the lipid composition includes at least one ionizable lipid having a charge (N), at least one peptide, wherein the peptide comprises LLELLESL (SEQ ID NO: 6), and a nucleic acid molecule comprising a charge (P), wherein the composition comprises an N/P ratio of 0.01 to 5.0, or from 0.01 to 0.2, or from 0.05 to 0.5, or from 0.1 to 1.0, or from 0.5 to 2.0, or from 1.0 to 5.0. In some embodiments, the administered lipid composition includes at least one ionizable lipid having a charge (N), at least one peptide, wherein the peptide comprises at least 80% sequence identity to GLFEALLELLESLWELLLEA (SEQ ID NO: 6), and a nucleic acid molecule comprising a charge (P), wherein the composition comprises an N/P ratio 0.01, 0.02, 0.04, 0.06, 0.08, 0.1, 0.12, 0.14, 0.16, 0.18, or 0.2. In other embodiments, the lipid composition comprises an N/P ratio of 0.4, 0.6, 0.8, 1.0, 2.0, 3.0, 4.0, 5.0, 6.0, 7.0 or 8.0. In some embodiments, the lipid composition comprises an N/P ratio from 0.01 to 1.0, from 0.5 to 2.0, or from 1.0 to 8.0. In some embodiments, the administered lipid composition further comprises at least one neutral lipid. In some embodiments, the administered lipid composition further comprises a transfection enhancing agent, such as a peptide comprising SEQ ID NO: 25 and/or SEQ ID NO: 26.

Moreover, provided herein are methods for targeting a payload to an immune cell of a subject, the method comprising administering a payload-containing lipid composition described herein. For example, the immune cell includes T cell, B cell, dendritic cell (DC), T helper cell, cytotoxic T cells (CTL), natural killer cell (NK), macrophage including tissue-specific macrophage populations, or combinations thereof. In some examples, the immune cell includes DCs. In other examples, the immune cell includes a spleen immune cell.

In some embodiments, the lipid composition targets an immune cell of the subject of the subject 1.2× or more compared to targeting of a non-immune cell of the subject. In some embodiments, the lipid composition targets an immune cell of the subject of the subject 1.2×, 1.3×, 1.4×, 1.5×, 1.6×, 1.7×, 1.8×, 1.9×, 2.0×, 2.5× or more compared to targeting of a non-immune cell of the subject.

Relative to a control level, the level that is determined may an increased level. As used herein, the term "increased" with respect to level (e.g., protein or mRNA level) refers to any % increase above a control level. In various embodiments, the increased level may be at least or about a 5% increase, at least or about a 10% increase, at least or about a 15% increase, at least or about a 20% increase, at least or about a 25% increase, at least or about a 30% increase, at least or about a 35% increase, at least or about a 40% increase, at least or about a 45% increase, at least or about a 50% increase, at least or about a 55% increase, at least or about a 60% increase, at least or about a 65% increase, at least or about a 70% increase, at least or about a 75% increase, at least or about a 80% increase, at least or about a 85% increase, at least or about a 90% increase, at least or about a 95% increase, relative to a control level.

Relative to a control level, the level that is determined may a decreased level. As used herein, the term "decreased" with respect to level (e.g., protein or mRNA level) refers to any % decrease below a control level. In various embodiments, the decreased level may be at least or about a 5% decrease, at least or about a 10% decrease, at least or about a 15% decrease, at least or about a 20% decrease, at least or about a 25% decrease, at least or about a 30% decrease, at least or about a 35% decrease, at least or about a 40% decrease, at least or about a 45% decrease, at least or about a 50% decrease, at least or about a 55% decrease, at least or about a 60% decrease, at least or about a 65% decrease, at least or about a 70% decrease, at least or about a 75% decrease, at least or about a 80% decrease, at least or about a 85% decrease, at least or about a 90% decrease, at least or about a 95% decrease, relative to a control level.

For example, in a biodistribution study, female BALB/c mice aged 6-10 weeks received lipid formulations containing 5 μg of firefly luciferase mRNA via intramuscular (IM) or intravenous (IV) routes, respectively. At 4 hours after the injection, mice were injected with d-Luciferin (150 mg kg-1, intraperitoneal) and imaged using an IVIS Lumina III system (Perkin Elmer) to observe the signal of luciferase. To further observe the signal value of a specific organ, tissues including liver, spleen, muscle, and lymph node were collected immediately, and luminescence of the tissue samples were measured by IVIS Lumina III system. The luminescence intensities in each region of interest (ROIs) of the isolated organs were quantified using the Living Image 3.0 software (PerkinElmer, Waltham, USA).

Additionally, the targeted delivery of the immune cell to the spleen included biodistribution (described above), which confirmed efficient delivery specifically to the spleen after intravenous administration of luciferase mRNA. Targeted delivery was also evaluated using a reporter mRNA and analysis of efficiency by flow cytometry.

In some embodiments, methods for delivering a payload to a spleen cell in a subject, are provided, which include: (i) admixing at least one ionizable lipid, at least one peptide, wherein the peptide comprises the sequence LLELLESL (SEQ ID NO: 1); and a payload, to form a lipid complex; and (ii) administering the payload-containing lipid complex to a subject. In some embodiments, methods for delivering a nucleic acid to a spleen cell in a subject, are provided, which include: (i) admixing at least one ionizable lipid, at least one peptide, wherein the peptide comprises at least 80% sequence identity to GLFEALLELLESLWELLLEA (SEQ ID NO: 6); and a payload, to form a lipid complex; and (ii) administering the lipid complex to a subject. In some embodiments, at least one neutral lipid is mixed with the at least one ionizable lipid and at least one peptide to form the lipid complex. In some embodiments, the payload is a nucleic acid, for example an RNA or a DNA molecule. In other embodiments, the payload comprises a peptide or polypeptide molecule.

In further examples, methods for expressing a protein in spleen tissue in a subject are provided, which include administering the lipid composition (lipid complex) to the subject.

Methods of Preparing

In some embodiments, methods for preparing a population of lipid formulations containing a nucleic acid payload molecule are provided, which include (a) mixing a nucleic acid payload with a peptide in an aqueous solution, wherein the peptide comprises the sequence LLELLESL (SEQ ID NO: 1); (b) injecting a lipid solution comprising an ionizable lipid into the aqueous solution, wherein the injecting comprises extrusion, in-line mixing, microfluidic mixing, evaporation, or vortexing; and (c) producing the population of lipid formulations complexed with a nucleic acid payload. In some embodiments, the peptide is in an ethanol solution when added. In some embodiments, the lipid solution of (b) further comprises at least one neutral lipid. In some embodiments, the peptide comprises at least 80% sequence identity to GLFEALLELLESLWELLLEA (SEQ ID NO: 6). In some embodiments, the peptide is selected from the group consisting of SEQ ID NOs: 6-24. In some embodiments, step (a) further comprises a second peptide which comprises at least one of SEQ ID NO: 25 and/or SEQ ID NO: 26.

In some embodiments, methods for preparing a population of lipid formulations containing a nucleic acid molecule payload are provided, which include (a) contacting a peptide comprising the sequence LLELLESL (SEQ ID NO: 1) with a lipid phase, wherein the lipid phase comprises an ionizable lipid, (b) contacting the components of step (a) with the nucleic acid payload in an aqueous solution; (c) mixing the components of step (b) by extrusion, in-line mixing, microfluidic mixing, evaporation, or vortexing; and (d) producing the population of lipid formulations complexed with a nucleic acid payload. In some embodiments, the peptide and lipids are in an ethanol solution when mixed with the aqueous solution containing the nucleic acid molecules. In some embodiments, the lipid phase of (a) further comprises at least one neutral lipid. In some embodiments, the peptide comprises at least 80% sequence identity to GLFEALLELLESLWELLLEA (SEQ ID NO: 6). In some embodiments, the peptide is selected from the group consisting of SEQ ID NOs: 6-24. In some embodiments, step (a) further comprises contacting the components with a second peptide which comprises at least one of SEQ ID NO: 25 and/or SEQ ID NO: 26.

In some embodiments, the preparation methods produce a population of lipid nanoparticles with a payload molecule encapsulated therein. In other embodiments, the preparation methods produce a population of liposomes with the payload encapsulated therein. In some embodiments, the preparation methods produce a population of lipid nanoparticles with a payload molecule complexed to the exterior of the lipid nanoparticle. In other embodiments, the preparation methods produce a population of liposomes with the payload molecule complexed to the exterior of the liposome. In some embodiments, the payload is a nucleic acid, for example an RNA or a DNA molecule. In other embodiments, the payload comprises a peptide or polypeptide molecule.

Kits

In aspects, a kit comprising a lipid composition is provided. In embodiments, the kit comprises the at least one ionizable lipid, and at least one peptide, wherein the peptide comprises the sequence LLELLESL (SEQ ID NO: 1) and reagents. In some embodiments of the kit, the peptide comprises at least 80% sequence identity to GLFEALLELLESLWELLLEA (SEQ ID NO: 6). In some embodiments, the kit further comprises at least one neutral lipid. In embodiments, a lipid composition in the kit is suitable for delivery (e.g., local injection) to a subject.

The present invention also provides packaging and kits comprising pharmaceutical compositions for use in the methods of the present invention. The kit can comprise one or more containers selected from the group consisting of a bottle, a vial, an ampoule, a blister pack, and a syringe. The kit can further include one or more of instructions for use in treating and/or preventing a disease, condition or disorder of the present invention, one or more syringes, one or more applicators, or a sterile solution suitable for reconstituting a pharmaceutical composition of the present invention.

In some examples, the kit comprising a lipid composition provides that the ionizable lipid and neutral lipid are in a separate container from the peptide. In some examples, the kit comprising a lipid composition provides that the ionizable lipid and neutral lipid are in the same container as the peptide.

EXAMPLES

The following examples illustrate certain specific embodiments of the invention and are not meant to limit the scope of the invention. Embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference.

Example 1

Lipid-peptide complex formulations having at least one ionizable lipid and at least one peptide were screened and assessed by various in vivo functional testing using the RNA payload of the complex. Performance and transfection efficiency analyses included payload delivery, biodistribution, cellular uptake, and response to expression of the payload encoded protein. mRNAs used included those encoding firefly luciferase (fLuc), Cre recombinase, GFP, and influenza virus hemagglutinin (HA).

At least one ionizable lipid, a neutral lipid, and the peptide SEQ ID NO: 6 were complexed with an mRNA payload using standard complexation or lipid nanoparticle formation procedures. As exemplified herein, the formulations examined varied, for example, in the concentration of peptide, the N/P ratios, and/or in type of ionizable lipid.

TABLE 3

Exemplary lipid complex formulations:

| Formulation | Ionizable lipid type | Peptide concentration | |
|---|---|---|---|
| LP1 | Formula IB | 0.05 | mg/ml |
| LP2 | Formula II | 0.05 | mg/ml |
| LP3 | Formula IA | 0.05 | mg/ml |
| LP4 | Formula II | (no peptide) | |
| LP5 | Formula II | 0.05 | mg/ml |
| LP6 | Formula II | 0.1 | mg/ml |
| LP7 | Formula VA | (no peptide) | |
| LP8 | Formula VA | 0.05 | mg/ml |
| LP9 | Formula VA | 0.1 | mg/ml |
| LP10 | Formula VA | 0.15 | mg/ml |

TABLE 4

Exemplary lipid complex formulations:

| Formulation | Ionizable lipid type | Lipid concentration | | Peptide concentration | |
|---|---|---|---|---|---|
| LP11 | Formula IA + Formula IB | 0.8 | mg/ml | 0.05 | mg/ml |
| LP12 | Formula IA | 2 | mg/ml | 0.05 | mg/ml |
| LP13 | Formula IA | 2 | mg/ml | 0.1 | mg/ml |
| LP14 | Formula IA | 2 | mg/ml | 0.2 | mg/ml |
| LP15 | Formula IA | 2 | mg/ml | 0.4 | mg/ml |
| LP16 | Formula II | 2 | mg/ml | 0.1 | mg/ml |
| LP17 | Formula II | 2 | mg/ml | 0.2 | mg/ml |
| LP18 | Formula II | 2 | mg/ml | 0.4 | mg/ml |

TABLE 5

Exemplary lipid complex formulations:

| Formulation | Ionizable lipid type | Lipid concentration | Peptide concentration |
|---|---|---|---|
| LP19 | Formula II | 1 mg/ml | 1.5 mg/ml SEQ ID NO: 27 + 0.1 mg/ml SEQ ID NO: 6 |
| LP20 | Formula | 1 mg/ml | 0.5 mg/ml SEQ ID NO: 27 + 0.1 mg/ml SEQ ID NO: 6 |
| LP21 | Formula IA | 1 mg/ml | 1.5 mg/ml SEQ ID NO: 27 + 0.1 mg/ml SEQ ID NO: 6 |
| LP22 | Formula IA | 1 mg/ml | 0.5 mg/ml SEQ ID NO: 27 + 0.1 mg/ml SEQ ID NO: 6 |

Ionizable lipid concentrations in the formulations of Table 3 ranged from 0.8 mg/l to 2.0 mg/l and all of the formulations in Tables 3-5 included one or two neutral lipids. The ionizable lipid type refers to the structure formulas provided herein.

The formulations in the examples were formulated using reverse evaporation or microfluidization. Lipids were weighed out and dissolved in chloroform, followed by evaporation on rotary evaporator. Lipid film was hydrated with water. In some situations, liposomal preparation was passed through microfluidizer. Lipid formulation was incubated with peptide solution overnight and stored at 4° C. until use.

For complexation with nucleic acid, lipid formulation and nucleic acid were diluted in buffer, mechanically mixed by pipetting and/or vortexing, and incubated at room temperature for 10-20 minutes prior to delivery in rodent models or cells.

Female BALB/c mice aged 6-10 weeks old purchased from The Jackson Laboratory and were acclimatized for 7 days before study.

Example 2

Firefly luciferase mRNA was complexed with each lipid-peptide formulation. Mice were injected with 5 μg fLuc mRNA-formulated lipid complexes using intravenous tail vein injection in a total volume 100 ml. At 4 h post-injection, mice were anesthetized with isofluorane anaesthesia and imaged 10 min after intraperitoneal injection of 100 μL Redirect D-Luciferin (Perkin Elmer). Bioluminescence imaging was quantified in vivo and ex vivo using an IVIS Lumina III imaging system (Perkin Elmer) and analyzed using Living Image software.

Figure 1B:
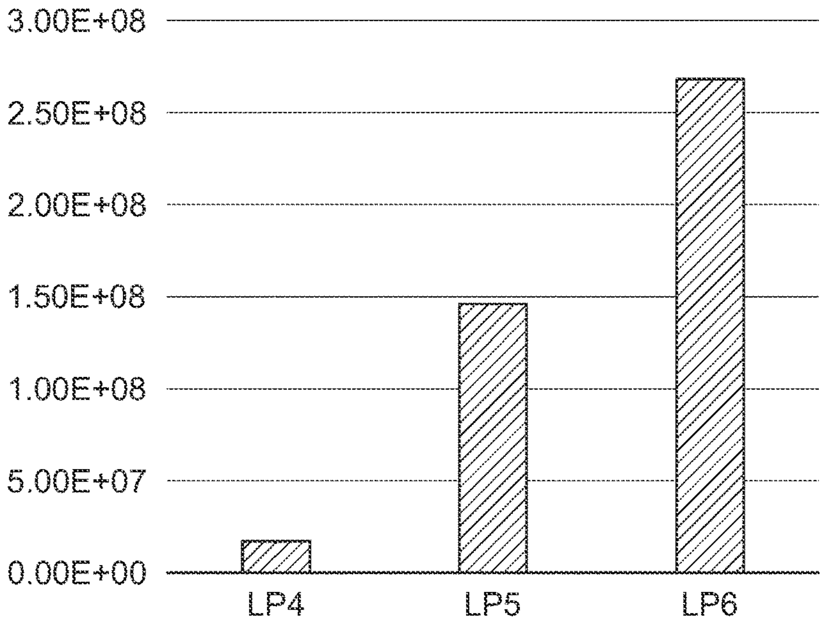
Figure 1C:
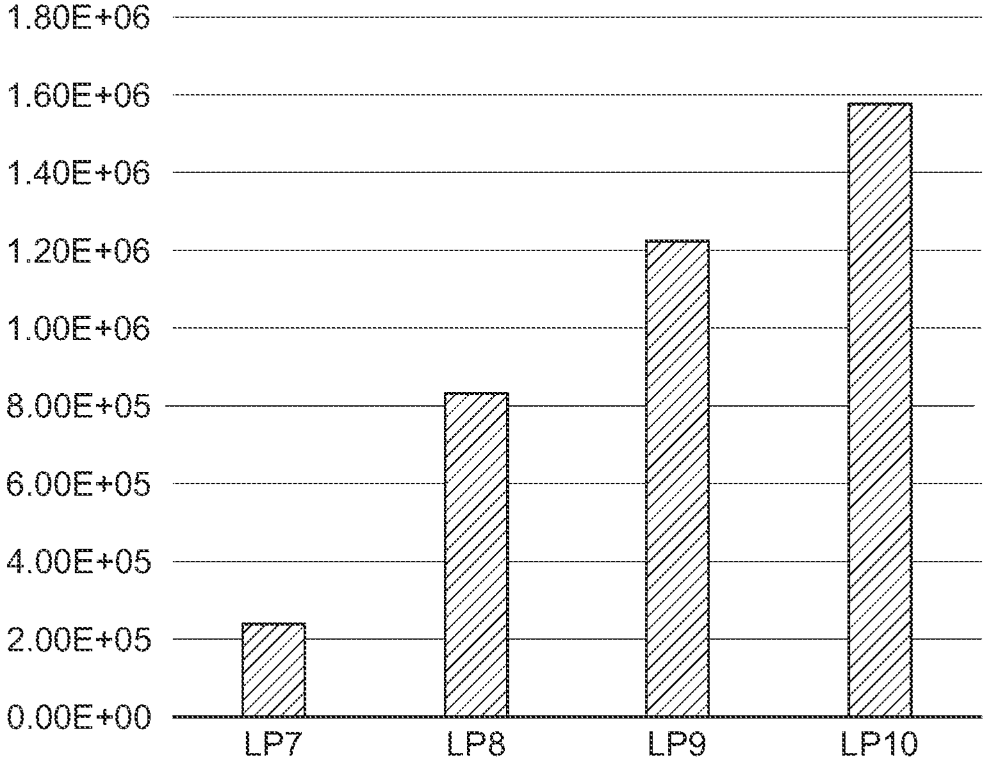
Figure 2:
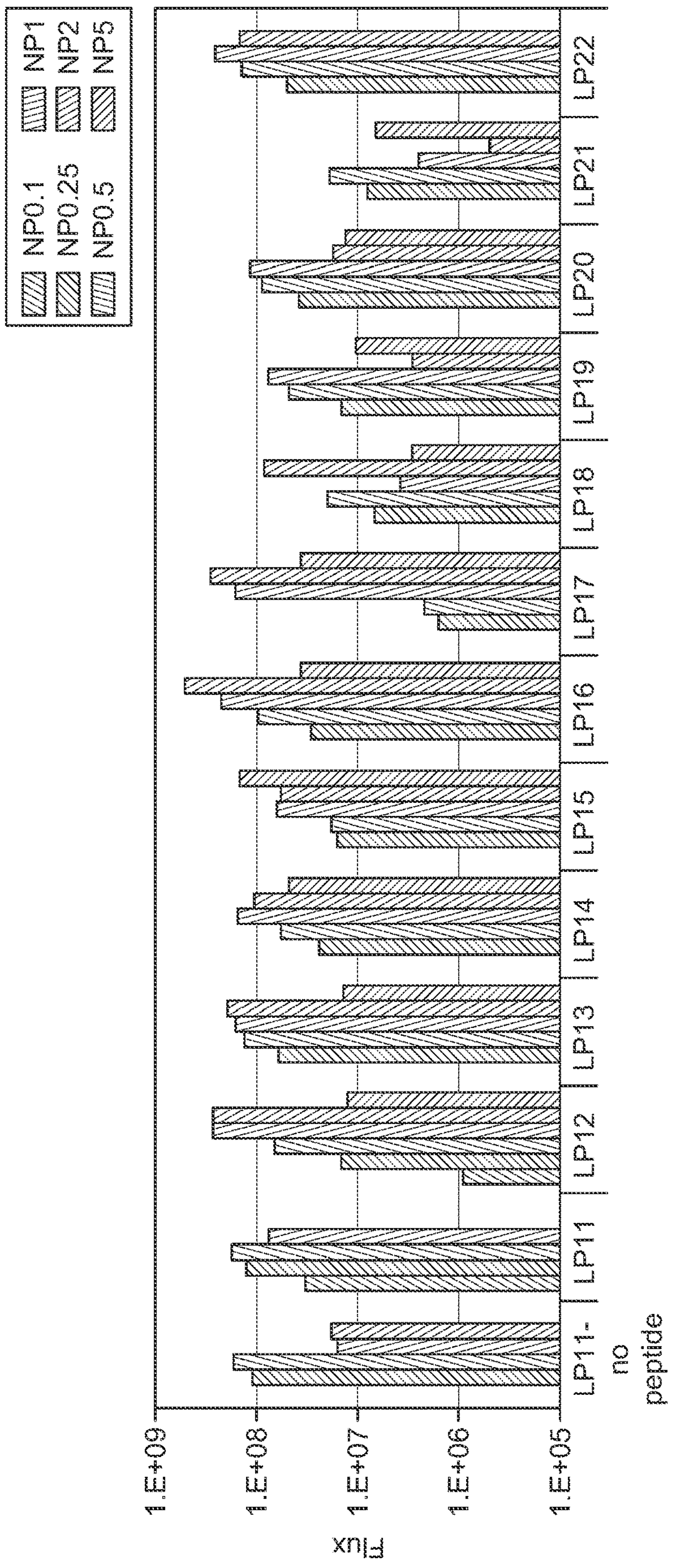
FIG. 2 is a graph depicting flux in spleens after intravenous administration of lipid-peptide formulations. The graph depicts results from formulations varying in N/P ratio from 0.1 to 5.0.

As shown in FIGS. 1A-1C, intravenous administration of various lipid complex-peptide formulations resulted in luciferase expression in the spleen. Formulations LP4, LP5 and LP6 all contain the same ionizable lipid and differ only in the amount of peptide. The presence of the peptide in the formulation significantly improved expression of the payload mRNA in spleen tissue compared to the lipid formulation without the peptide. For example, compare flux for LP4 (no peptide) to that for LP5 and LP6 in FIG. 1B.

Formulations LP7, LP8, LP9 and LP10 contain the same ionizable lipid and differ only in the amount of peptide. Although the overall expression in the spleen was less with the formulations shown in FIG. 1C compared to that with the formulations shown in FIGS. 1A and 1B, the presence of the peptide significantly improved the expression of the luciferase mRNA in spleen tissue for the Formula VA-based lipid formulations. For example, compare flux for LP7 (no peptide) to that for the formulations in FIG. 1C.

In vivo delivery performance of formulations LP11-LP22 with N/P ratios ranging from 0.1 to 5 was assessed following intravenous administration. The spleen flux results are shown in FIG. 2. The formulation results were compared to that obtained using mRNA-complexed formulation LP11 without SEQ ID NO:6 peptide ("LP11-no peptide" in FIG. 2).

Figure 3:
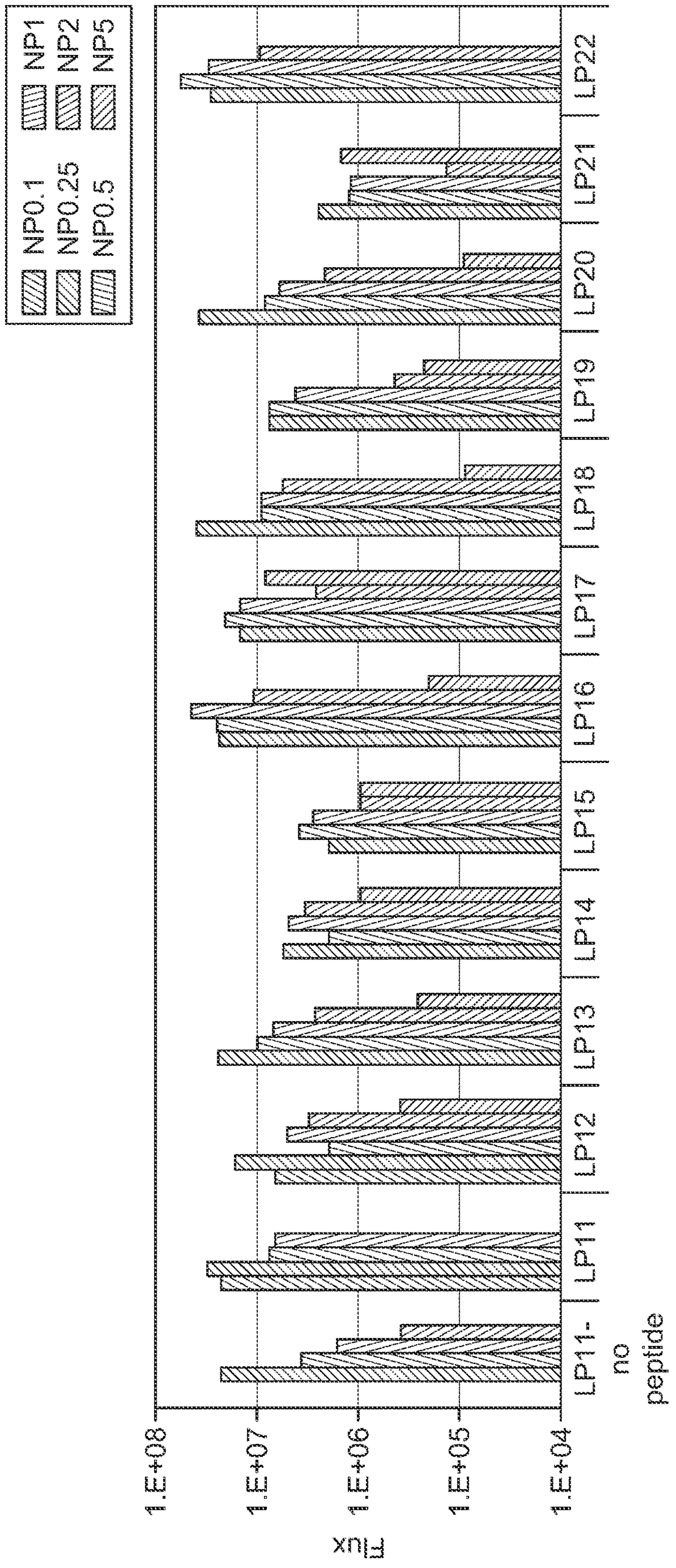
FIG. 3 is a graph depicting flux in muscle after intramuscular administration of lipid-peptide formulations. The graph depicts results from formulations varying in N/P ratio from 0.1 to 5.0.

Following intramuscular administration of formulations LP11-LP22 with N/P ratios ranging from 0.1 to 5, in vivo delivery performance was assessed following intramuscular administration. The luciferase signal was localized at injection region (muscle) and luciferase flux quantitation results are shown in FIG. 3. As above, formulation LP11 without SEQ ID NO: 6 peptide ("LP11-no peptide" in FIG. 3) was used as a control. No significant fLuc expression was observed in other organs up to 72 hours after intramuscular injection of the formulations, confirming highly specific non-hepatic targeting of the formulation.

Figure 4A:
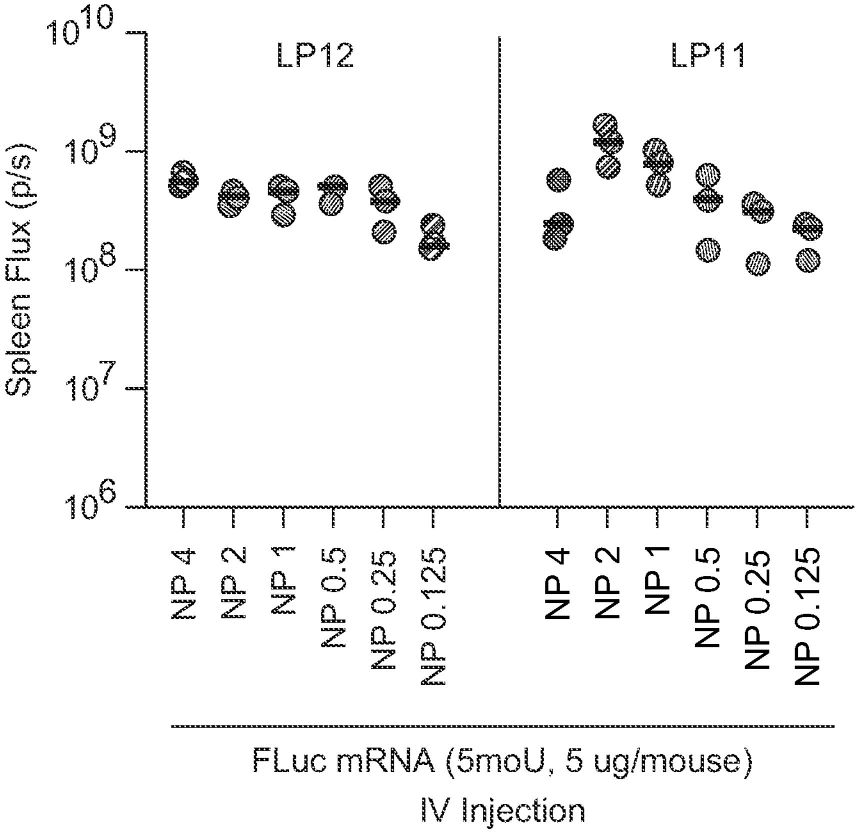
FIGS. 4A-4B are data showing the effect of different N/P ratios (a ionizable lipid comprising a charge N and a nucleic acid molecule comprising a charge P) on biodistribution and delivery efficacy for formulations LP11 and LP12 following intravenous injection.
Figure 4B:
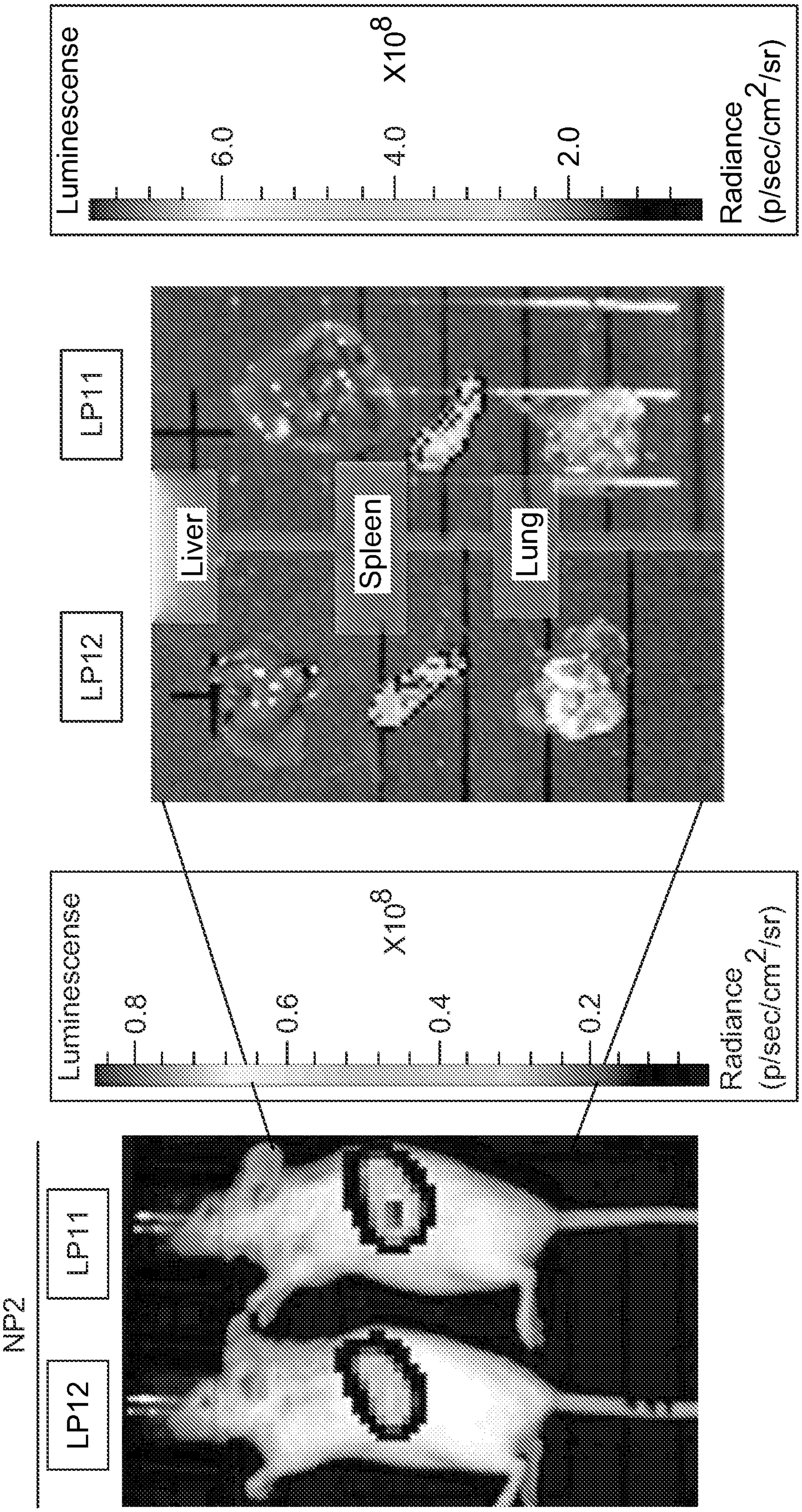

The N/P ratio was varied in fLuc mRNA-complexed LP11 and LP12 formulations and the effect on spleen delivery and biodistribution following intravenous injection was assessed. As shown in FIG. 4A, N/P ratios as low as 0.125 with these formulations were effective in delivering fLuc mRNA expression in the spleen. These formulations also resulted in delivery specifically to the spleen, rather than to the liver or lung (FIG. 4B).

Figure 5:
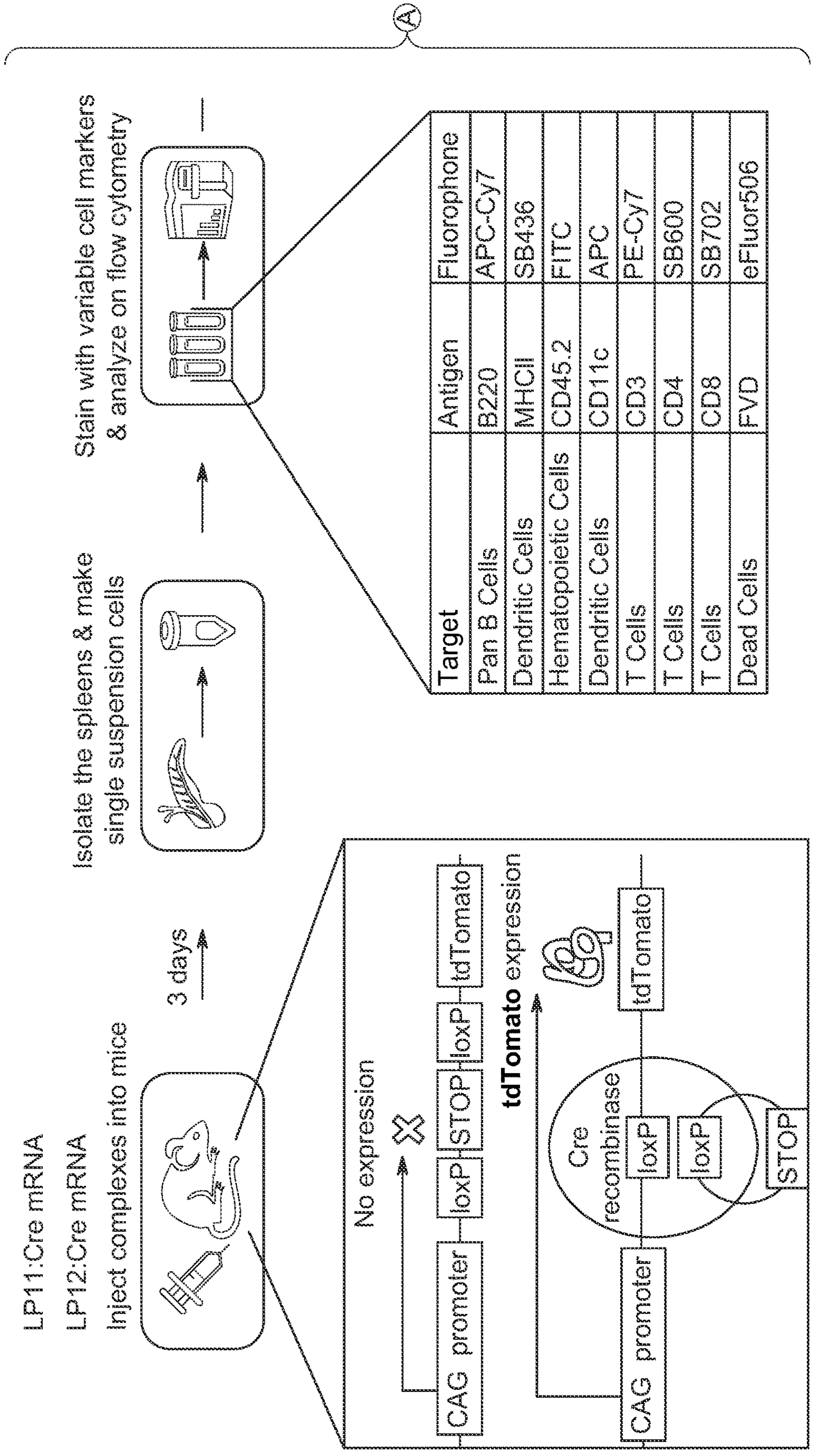
FIG. 5 is an image showing a schematic of using tdTomato reporter mice and Cre mRNA as lipid complex payload to analyze cell populations that are being targeted. For splenocyte analysis, splenocytes were partitioned into two staining groups and stained fluorescent antibodies for CD8 (APC), CD4 (PE), and B220 (FITC) or F480 (APC), CD11b (FITC), and CD11c (PE).
Figure 5:
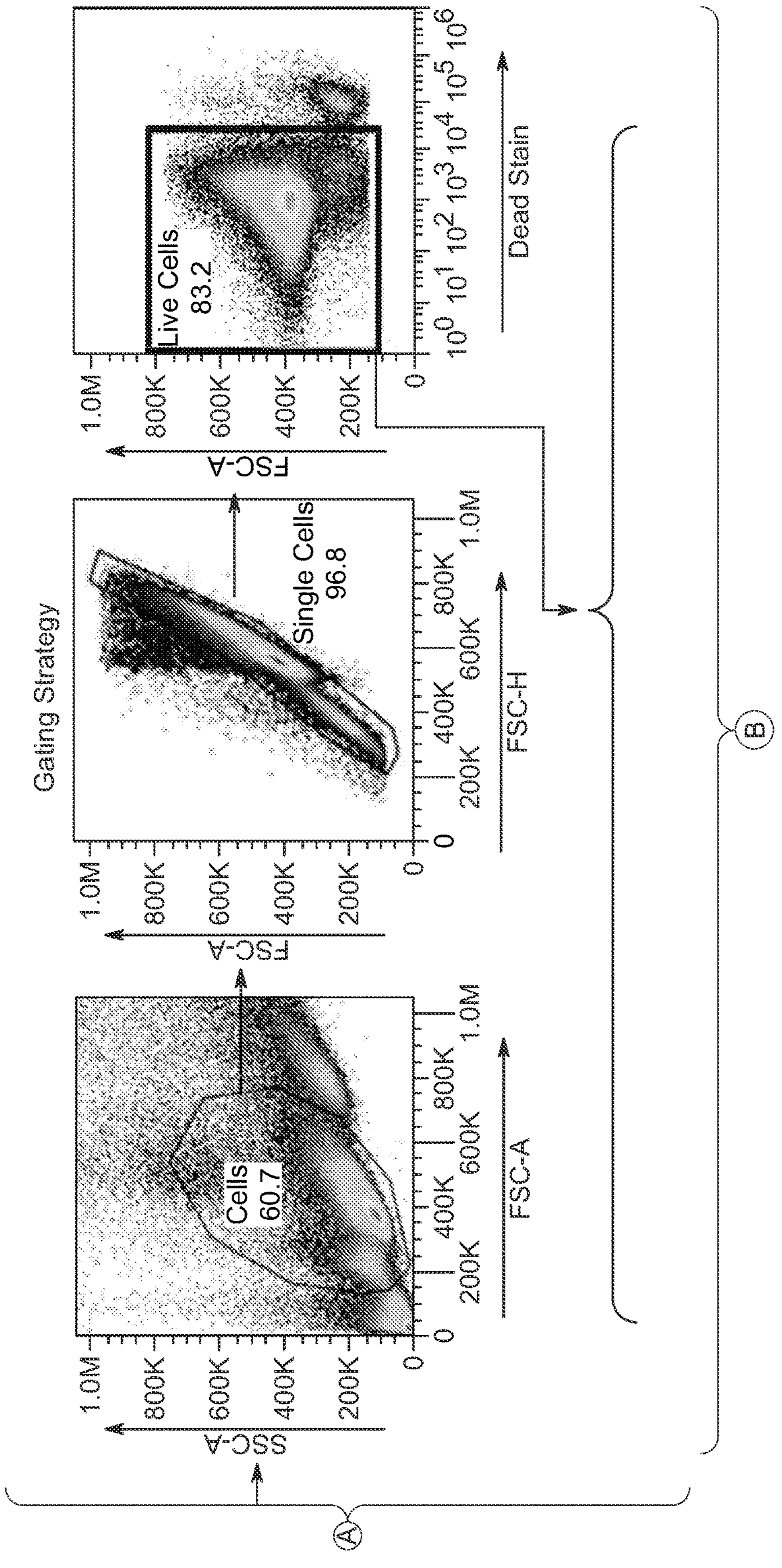
Figure 5:
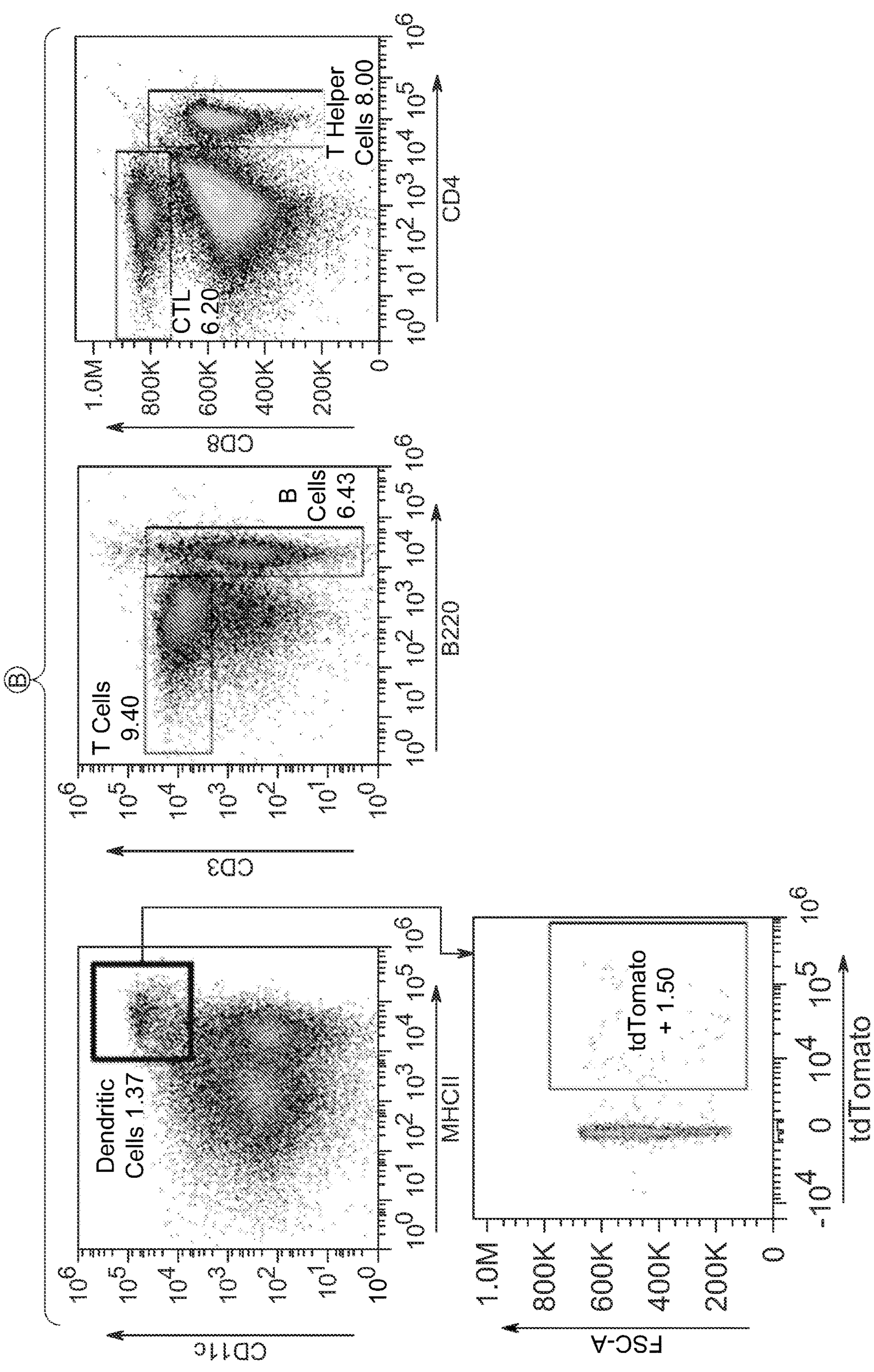

Example 3 tdTomato reporter mice were used to analyze spleen cell populations targeted by the lipid-peptide formulations. A schematic for the workflow and analysis is shown in FIG. 5. Cre mRNA was complexed with LP11 and LP12 formulations and the complexes administered to Ai14 mice intravenously. Five days after injection, the animals were killed and the spleens harvested.

For splenocyte analysis, single-cell suspensions were prepared by passing the spleens through 70-μm cell strainers followed by lysis of blood cells with ACK Lysing Buffer and washing two times with PBS. Splenocytes were partitioned into two staining groups and stained fluorescent antibodies for CD8 (APC), CD4 (PE), and B220 (FITC) or F480 (APC), CD11b (FITC), and CD11c (PE). Fluorescence of BDK-CART transfection in subpopulations was detected was detected on LSR-II.UV (BD Biosciences) using the Pacific Blue channel.

Figure 6:
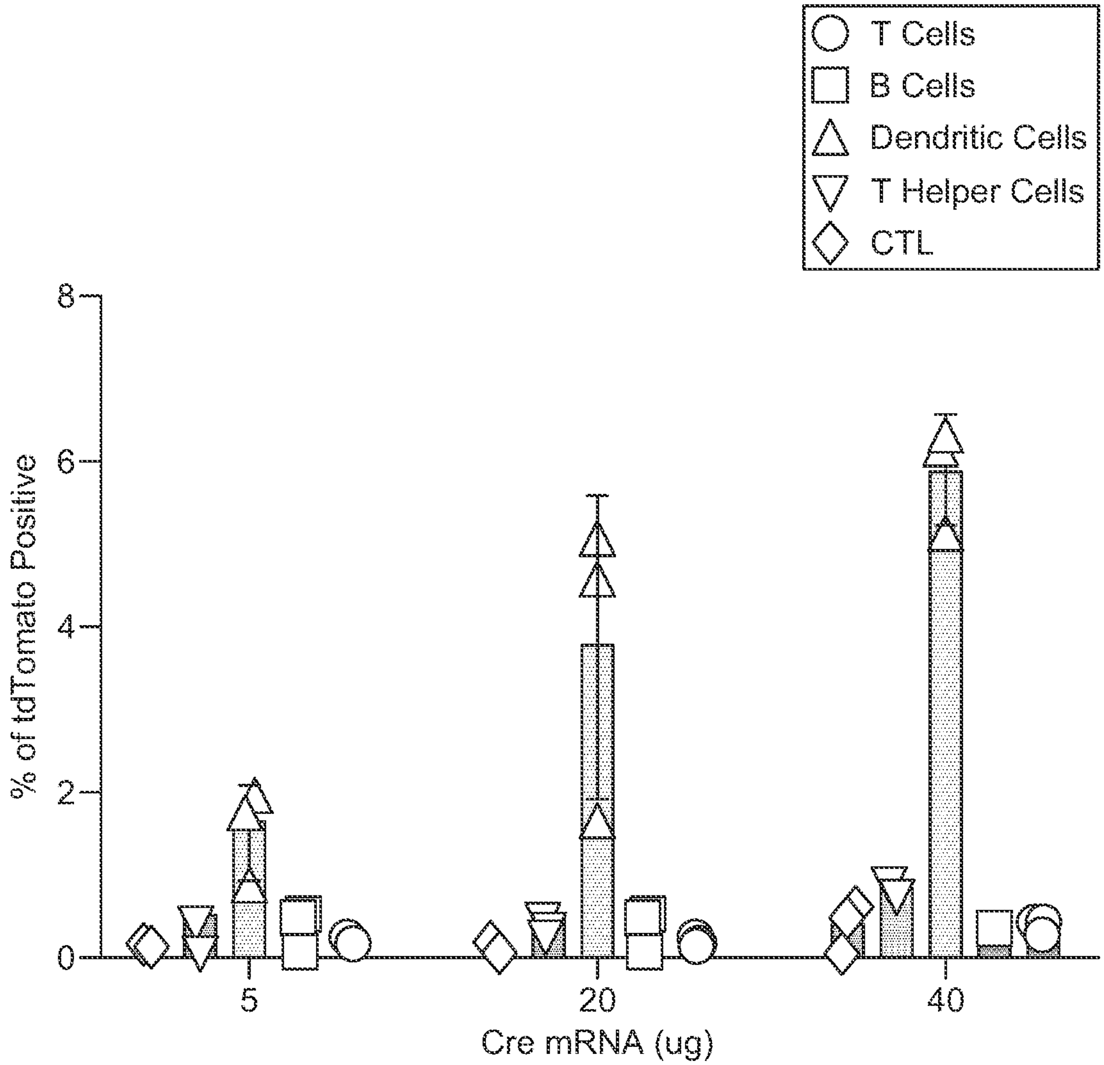
FIG. 6 is a graph showing the specific delivery of the Cre mRNA containing LP11 formulation composition to the dendritic cell (DC) population in the spleen at administered doses of 5 μg, 10 μg and 40 μg Cre mRNA.

As shown in FIG. 6, the Cre mRNA containing LP11 formulations delivered functional Cre mRNA to the dendritic cell population of the spleen. Delivery to dendritic cells of the spleen was significantly greater than delivery to the splenic B and T cell populations. A similar pattern was observed when GFP mRNA was used for delivery.

Figure 7A:
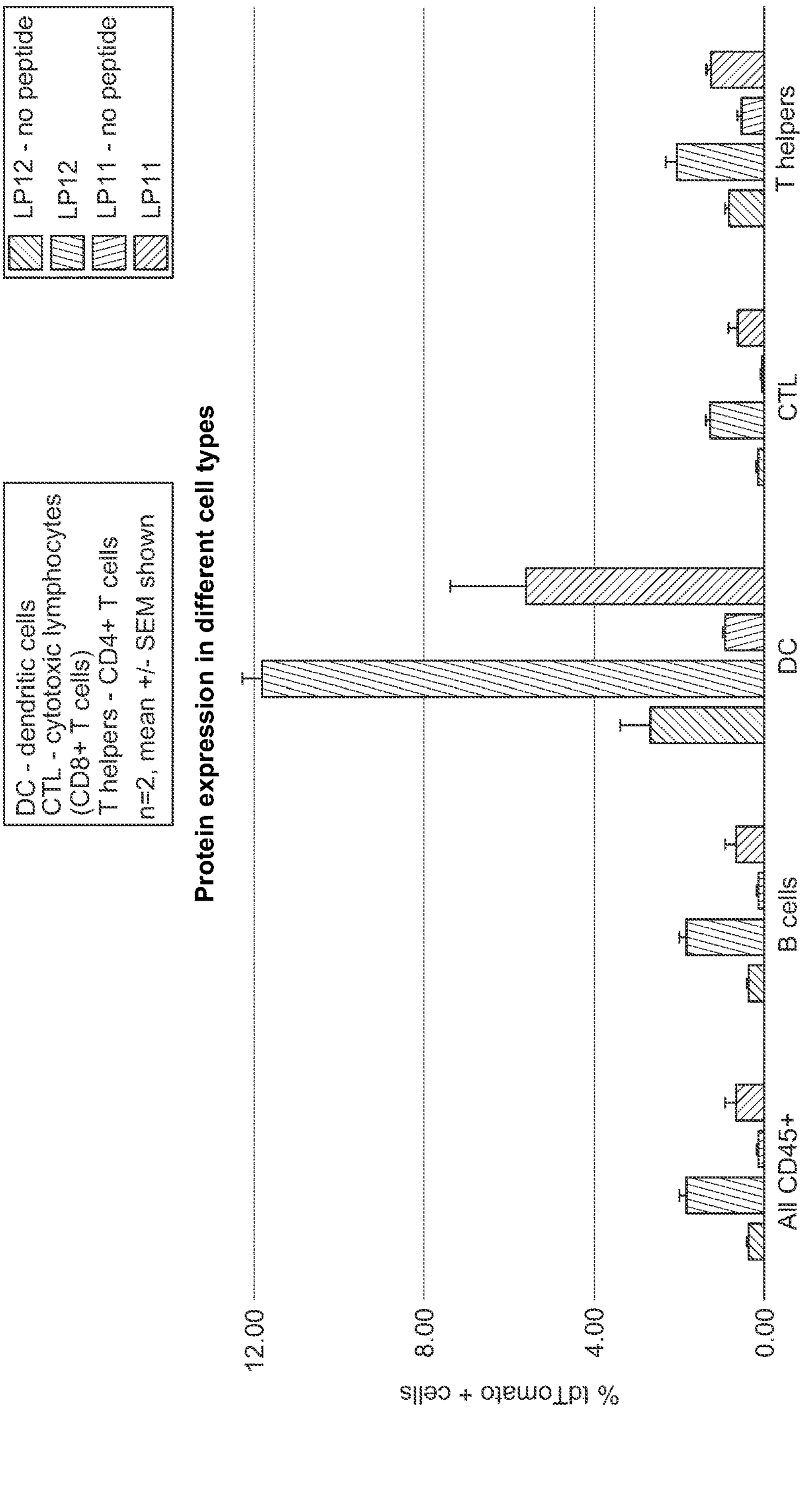
FIG. 7A is a bar graph showing tdTomato expression in different splenocyte populations following intravenous administration of Cre mRNA-formulated lipid compositions using LP11, LP12, and the LP11 and LP12 formulations without SEQ ID NO:6 peptide (LP11-no peptide and LP12-no peptide).
Figure 7B:
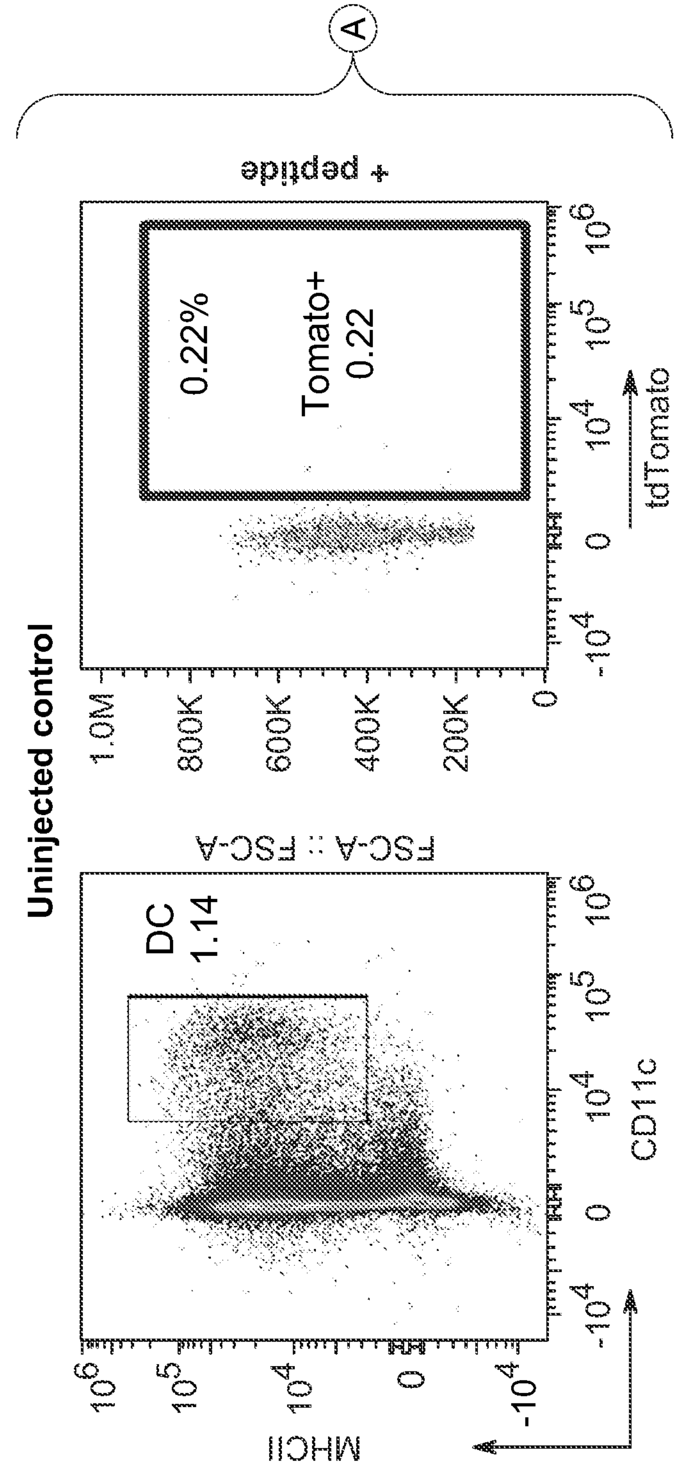
FIG. 7B are images showing representative gating in spleen dendritic cells (MHCII+/CD11C+ population) versus tdTomato expression following administration of Cre mRNA-formulated lipid compositions using LP11, LP12, LP11-no peptide, and LP12-no peptide.
Figure 7B:
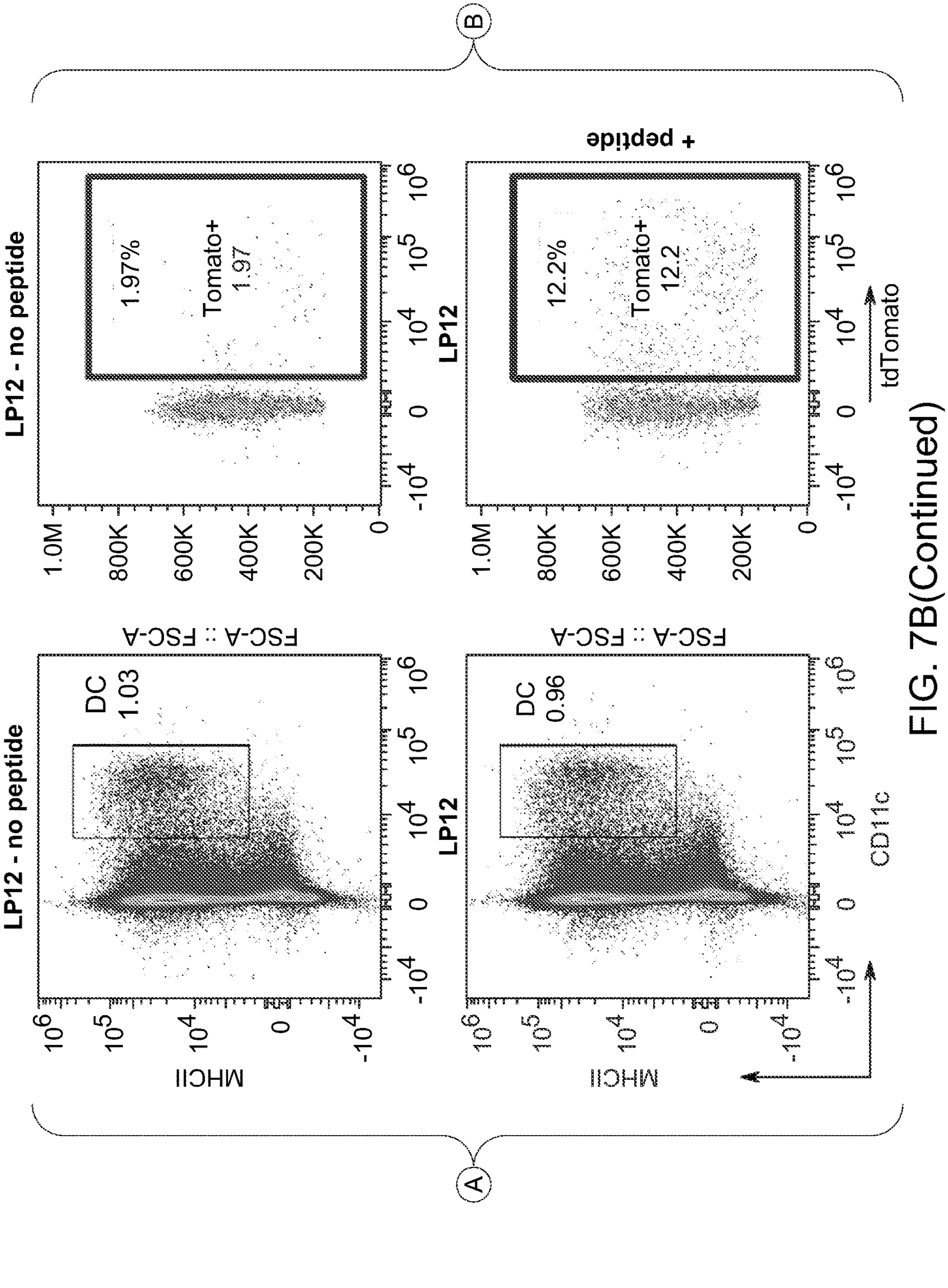
Figure 7B:
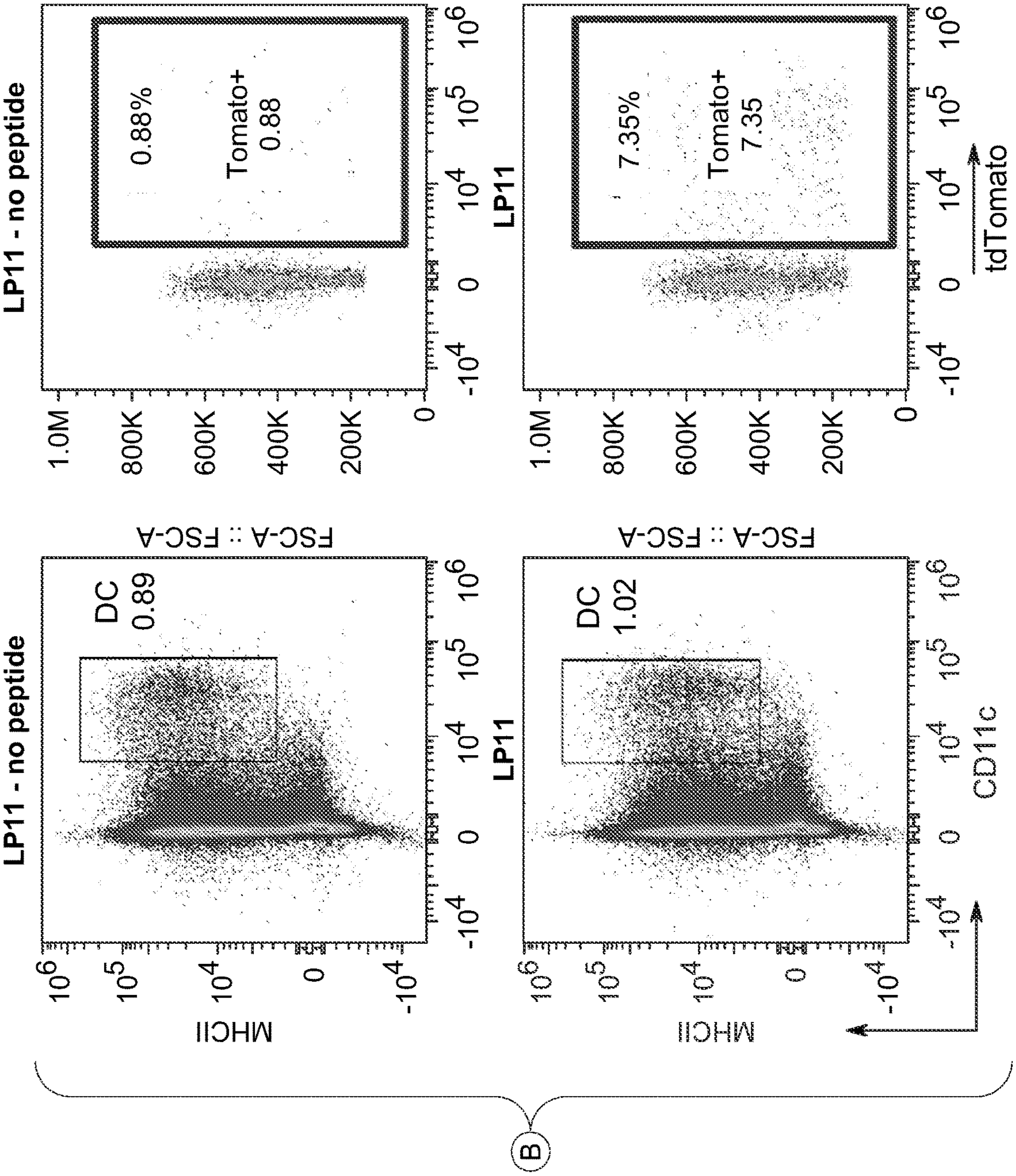

Performance of the LP11 and LP12 formulations in splenocyte delivery was compared to that using the LP11 and LP12 formulations without SEQ ID NO: 6 peptide ("LP11-no peptide" and "LP12-no peptide" in FIGS. 7A and 7B). The lipid formulations were complexed with Cre mRNA-formulated lipid compositions were administered intravenously to Ai14 mice. Five days after administration, splenocytes prepared as above and labeled with fluorescent antibodies against various immune cell types. Flow cytometric gating strategy was used to identify cell marker versus tdTomato expression.

Both LP11 and LP12 formulations were more effective in Cre mRNA delivery to all immune cell types of the spleen analyzed (as indicated by tdTomato expression) than either LP11 and LP12 formulations without SEQ ID NO: 6 peptide (FIG. 7A). As also shown in FIG. 7A, both LP11 and LP12 formulations were significantly more effective in delivering the mRNA to dendritic cells as compared to the other immune cells of the spleen. FIG. 7B shows representative flow cytometric gating results in the dendritic cell population (MHCII/CD11c) versus tdTomato expression.

Figure 8A:
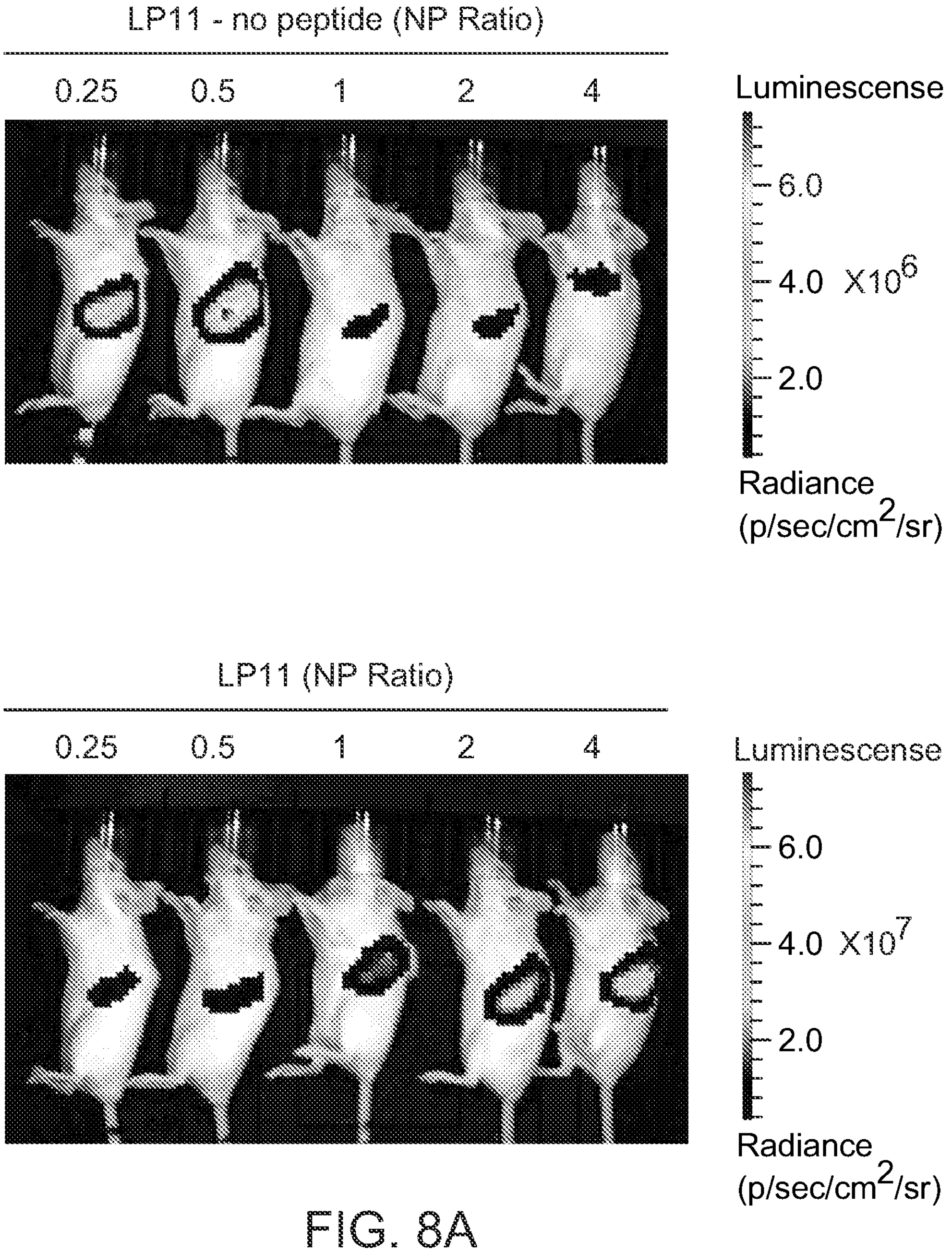
FIGS. 8A-8B are data showing in vivo expression of fLuc mRNA-formulated LP11 formulation or LP11 formulation without SEQ ID NO:6 peptide (LP11-no peptide) at different N/P ratios.
Figure 8B:
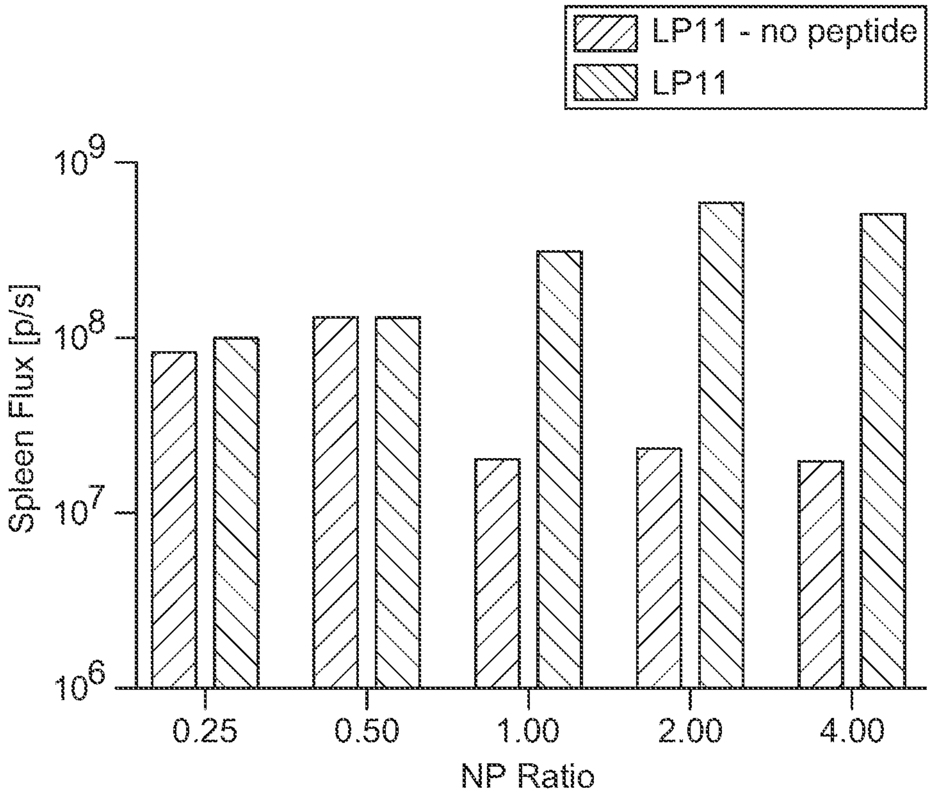

Firefly luciferase (fLuc) mRNA was formulated with LP11 formulation at varying N/P ratios. Similarly, fLuc mRNA was formulated with LP11 formulation without SEQ ID NO: 6 peptide at the same N/P ratios. The mRNA containing compositions were administered via intravenous (IV) injection and imaged at 4 h post-injection as described in Example 2. FIGS. 8A and 8B show exemplary results of the LP11 formulation and LP11 without peptide formulation with N/P ratios from 0.25 to 4.0. At N/P ratios of 1.0 to 4.0, the LP11 formulations showed enhanced over that of LP11 without peptide formulations.

In a repeat dosing experiment, two doses of a composition of fLuc mRNA formulated with LP11 formulation at N/P 2 were administered via IV injection to 4 mice with a two week time period between doses. The mice were imaged at 4 h post-injection as described in Example 2. Imaging of the bioluminescence intensity showed that the administered formulation delivered the fLuc mRNA payload specifically to the spleen. The bioluminescence imaging in the region of interest was used to calculate total flux (photons/second, p/s) from the expressed fLuc. The average total flux measured after the first injection was $1.103\times10^9$ p/s and after the second injection was $1.072\times10^9$ p/s. A control mouse receiving a single dose exhibited a total flux of $1.103\times10^9$ p/s. Accordingly, the formulation allows for repeated administrations and prime-boost dosing.

Example 4

Figure 9:
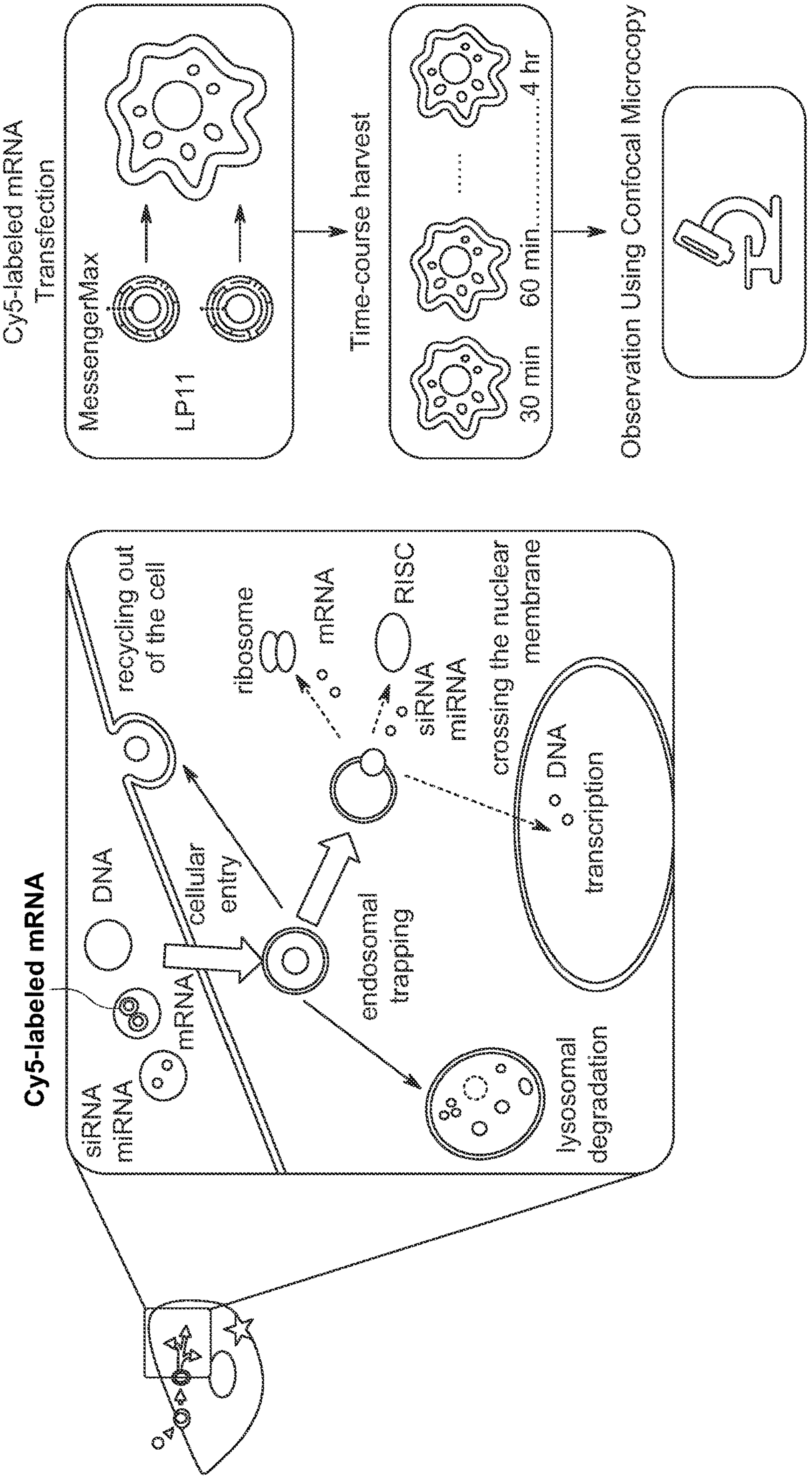
FIG. 9 depicts an image of a schematic of lipid complex uptake analysis of formulations provided herein.
Figure 11:
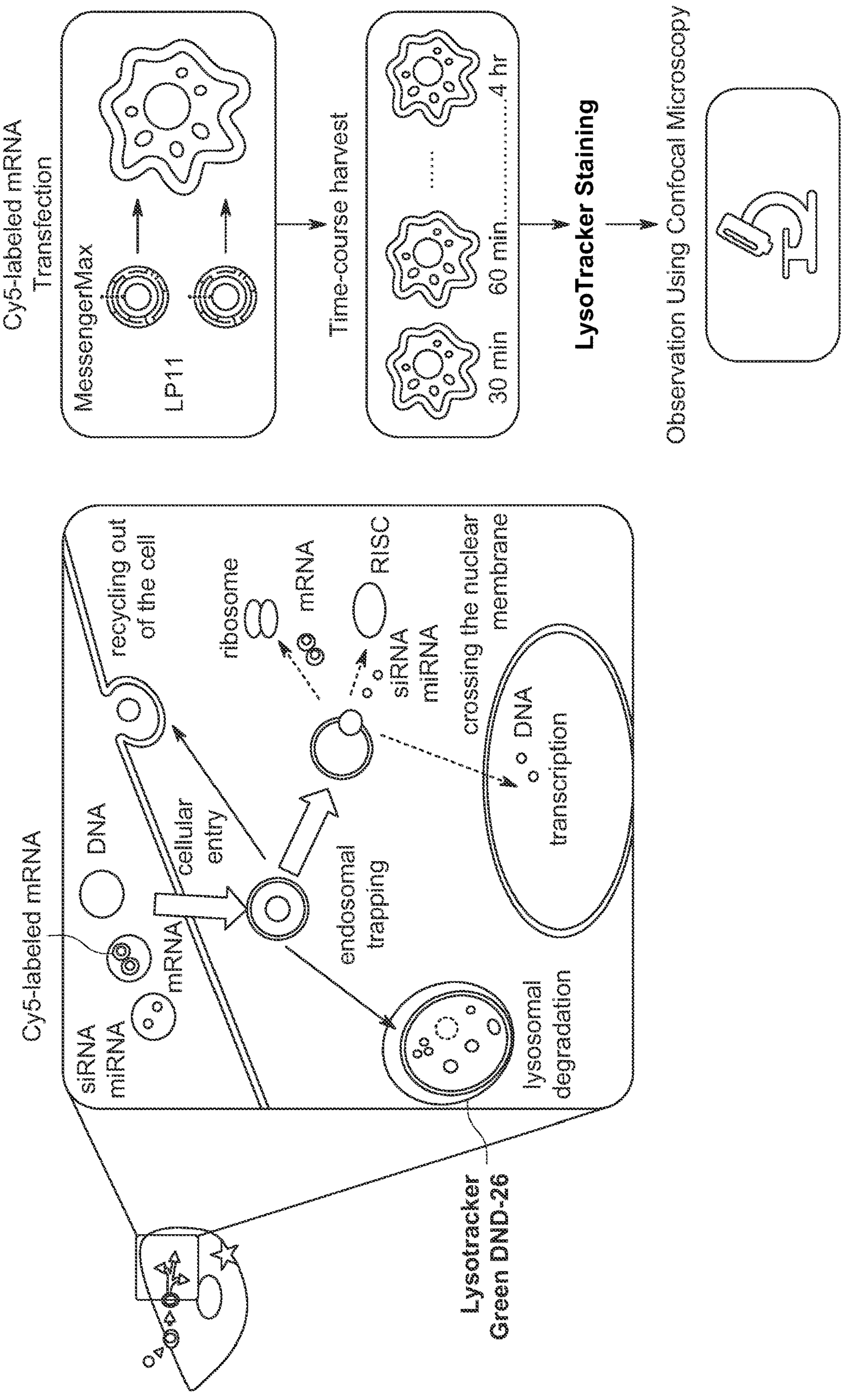
FIG. 11 depicts an image of a schematic of lipid complex uptake and endosomal escape analysis of formulations provided herein.

Intracellular endosomal uptake and release of nucleic acid-containing lipid complexes were examined using workflows depicted in FIGS. 9 and 11. For this analysis, HEK293 cells were transfected with Cy5-labeled mRNA complexed LP formulation or LP11 without SEQ ID NO: 6 peptide formulation and incubated at 37° C. and 5% $CO_2$. After 15 minutes, 30 minutes, 60 minutes and 90 minutes, cells were fixed with 4% formaldehyde and counterstained with DAPI to identify cell nuclei. Confocal laser-scanning microscope (Zeiss) was used for fluorescence imaging.

Figure 10A:
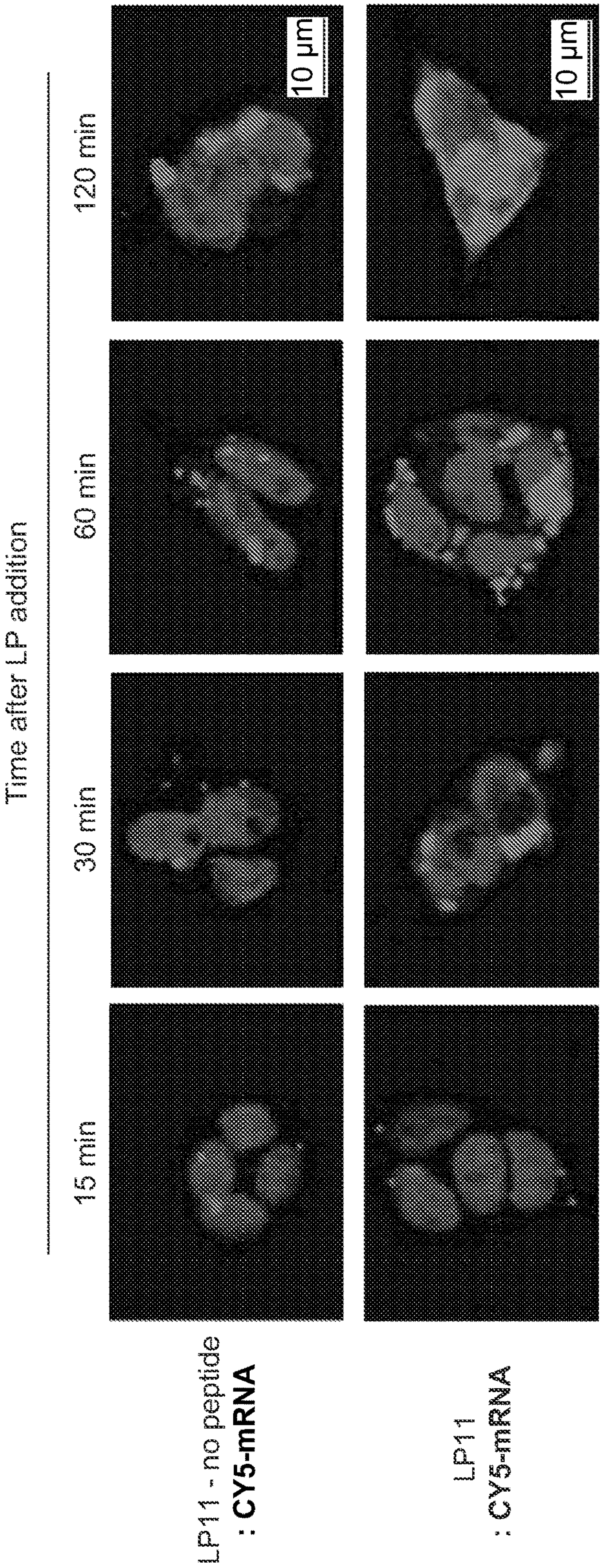
FIGS. 10A-10B are data showing cellular uptake of mRNA complexed LP11 formulations or of mRNA complexed LP11 without SEQ ID NO:6 peptide formulations (LP11-no peptide).
Figure 10B:
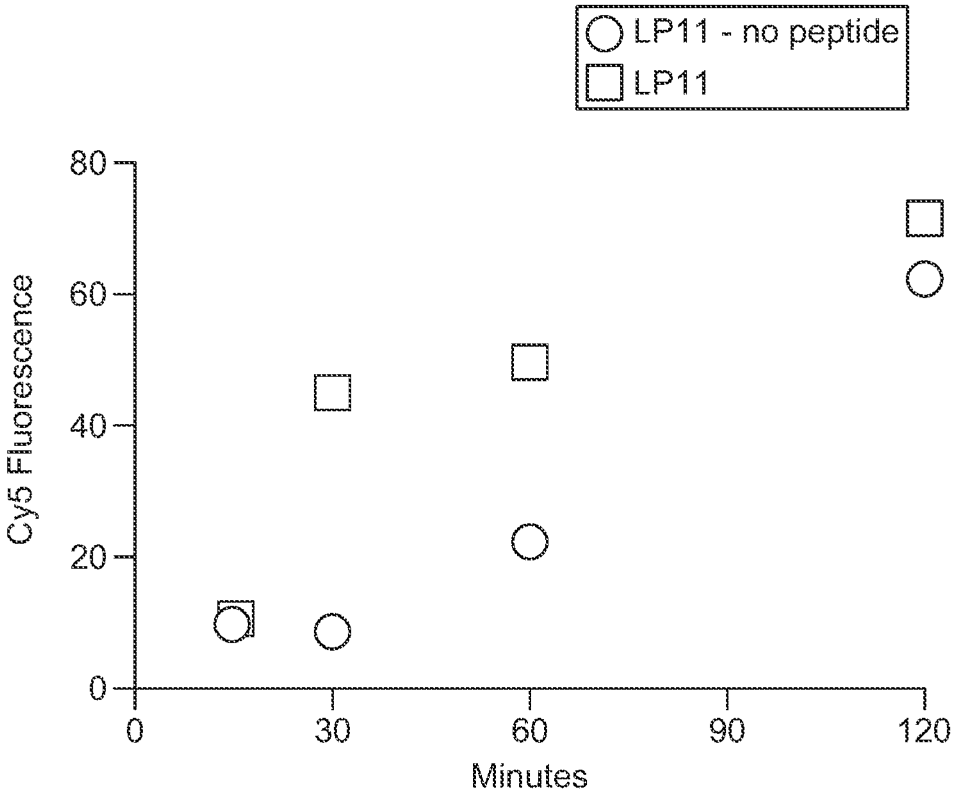

Exemplary results of uptake of mRNA-lipid complexes are shown in FIG. 10A, with red fluorescence indicating Cy5-mRNA and blue fluorescence indicating DAPI. Quantitation of the cellular uptake over time is shown in FIG. 10B. The LP11 formulation internalized at an earlier time relative to the LP11 formulation without peptide, indicating a more efficient cellular uptake for the complete LP11 formulation.

To examine endosomal escape of the complexes, HEK293 cells were transfected with Cy5-labeled mRNA complexed LP formulation or LP11 without SEQ ID NO: 6 peptide formulation and incubated at 37° C. and 5% $CO_2$ for 3 hours. 50 nM LysoTracker™ Green DND-26 (Invitrogen) was added to the cells for 30 minutes before fixation to identify late endosome in lysosomal degradation (FIG. 11). The cells were then fixed and counterstained with DAPI as above, and images were acquired using a confocal laser-scanning microscope.

Figure 12:
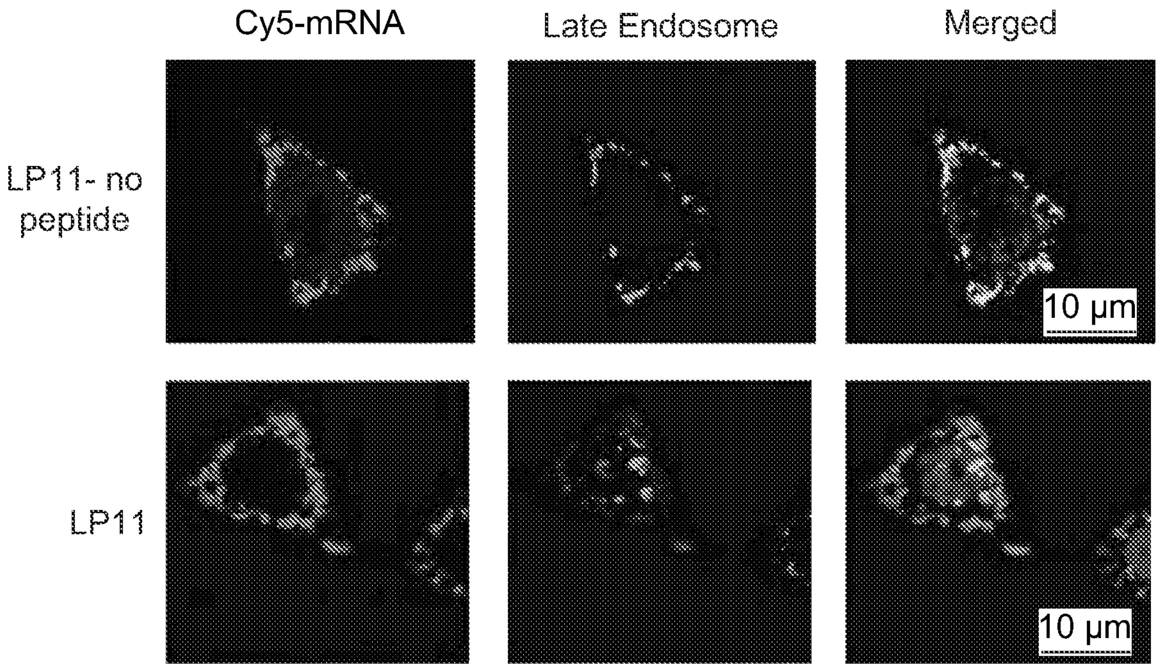
FIG. 12 depicts representative fluorescent images showing endosomal escape of mRNA complexed LP11 formulations or of mRNA complexed LP11 without SEQ ID NO:6 peptide formulations (LP11-no peptide) in transfected HEK293 cells. Red: Cy5 mRNA (left two panels); Green: late endosomal marker (center two panels); Merged: Red Cy5-mRNA, Green late endosomal marker and Blue DAPI nucleus (right two panels); scale bars 10 μm.

Exemplary results of endosomal escape of mRNA-lipid complexes are shown in FIG. 12, with red fluorescence indicating Cy5-mRNA (left two panels), green fluorescence indicating late endosomal marker (center two panels) and blue fluorescence indicating DAPI (right two panels). The LP11 formulation showed a more efficient endosomal escape than the LP11 formulation without peptide. As seen in the merged image (FIG. 12, right two panels), much less mRNA appeared free from LysoTracker staining using the complete LP11 formulation compared to the LP11 formulation without peptide.

Example 5

Immunogenicity is defined as the ability of a substance (e.g., vaccine) to elicit an adaptive immune response. Humoral immunity and cell-mediated immunity are two types of an adaptive immune response that enables a body to defend itself in a targeted way against foreign substance (antigen). Humoral immune response is an antibody-mediated response that occurs when antigens are detected in the body. This mechanism is primarily driven by B cells that produce antibodies after the detection of a specific antigen. Unlike humoral immunity, cellular immunity does not depend on antibodies. Cell-mediated immunity is primarily driven by mature T cells and the release of various cytokines (e.g., IFN-γ) in response to an antigen.

Figure 13:
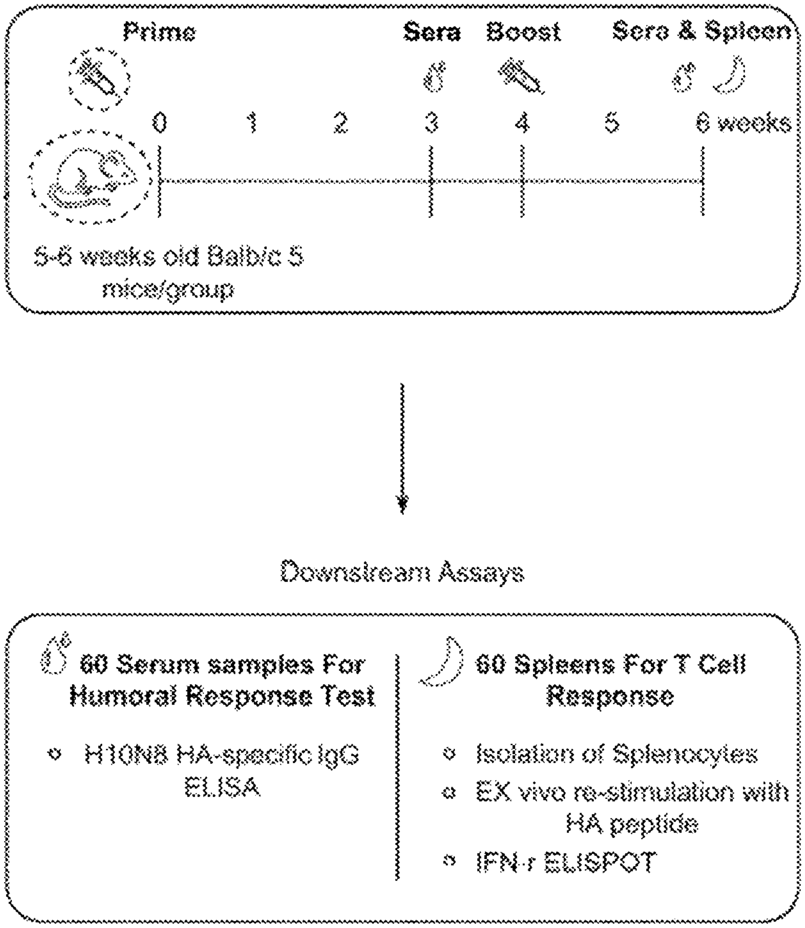
FIG. 13 depicts an image of a schematic for the immunogenicity study design.

The humoral and cellular immunogenicity of an antigen administered via an antigen-encoding mRNA formulated with lipid compositions was evaluated to demonstrate potential for such formulations for vaccine applications. The workflow and tested compositions for an immunogenicity study is shown in FIG. 13.

Lipid-mRNA complexes of H10N8 influenza Hemagglutinin (HA) mRNA complexed LP11 or LP12 formulations were prepared. The mRNA containing complexes were administered to BALB/c mice either intramuscularly (IM) or intravenously (IV) according to prime-boost immunization schedules with a 4-week interval. FIG. 13 indicates the immunization schedule, the mRNA doses and routes of complex administration, and subsequent assays performed for assessing humoral and cellular immune responses. The mRNA doses shown in FIG. 13 relate to those shown in FIGS. 14-15 as follows: 0.02 μg is 0.01 mg/kg (mRNA amount/mouse weight); 1 μg is 0.05 mg/kg, 5 μg is 0.25 mg/kg, 10 μg is 0.5 mg/kg, and 20 μg is 1 mg/kg.

Figure 14A:
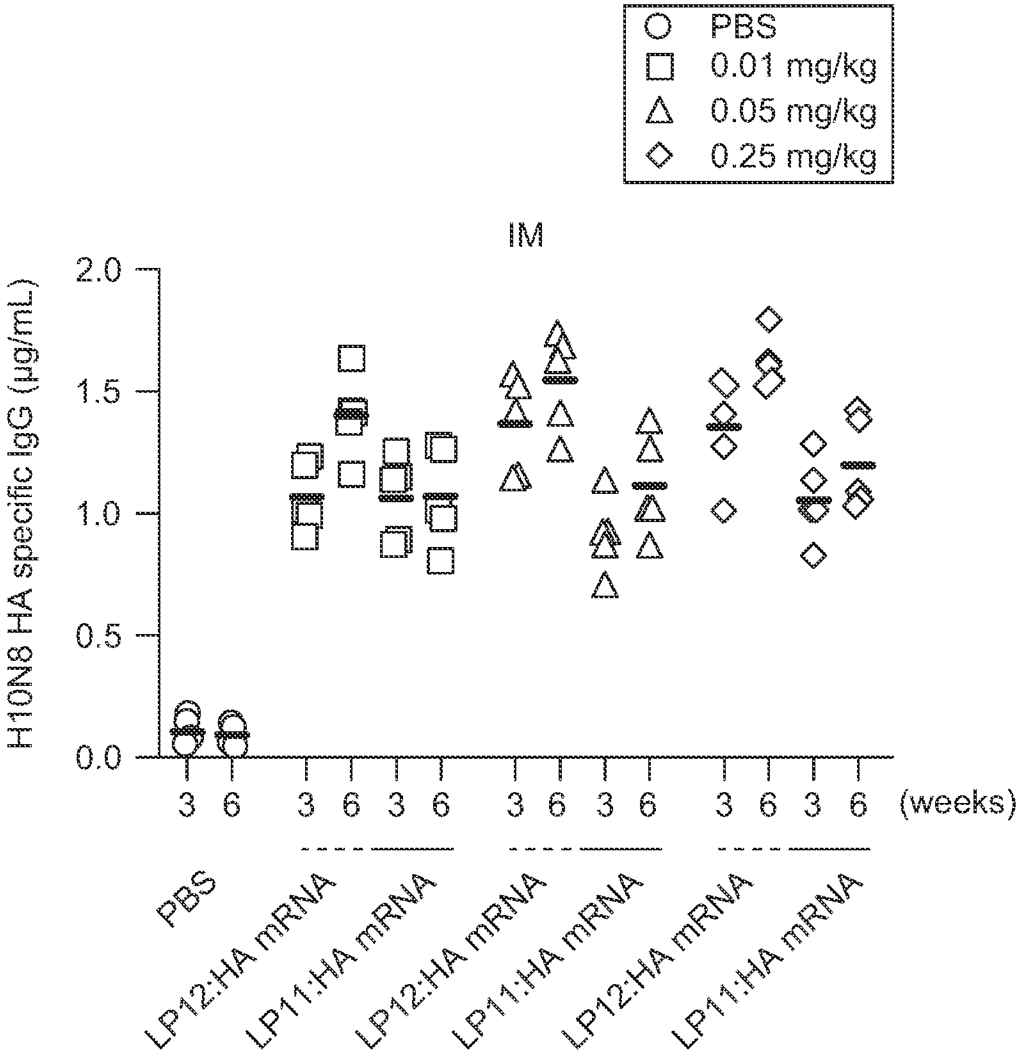
FIGS. 14A-14B are graphs showing the HA antigen-specific humoral immune response at 3 and 6 weeks.
Figure 14B:
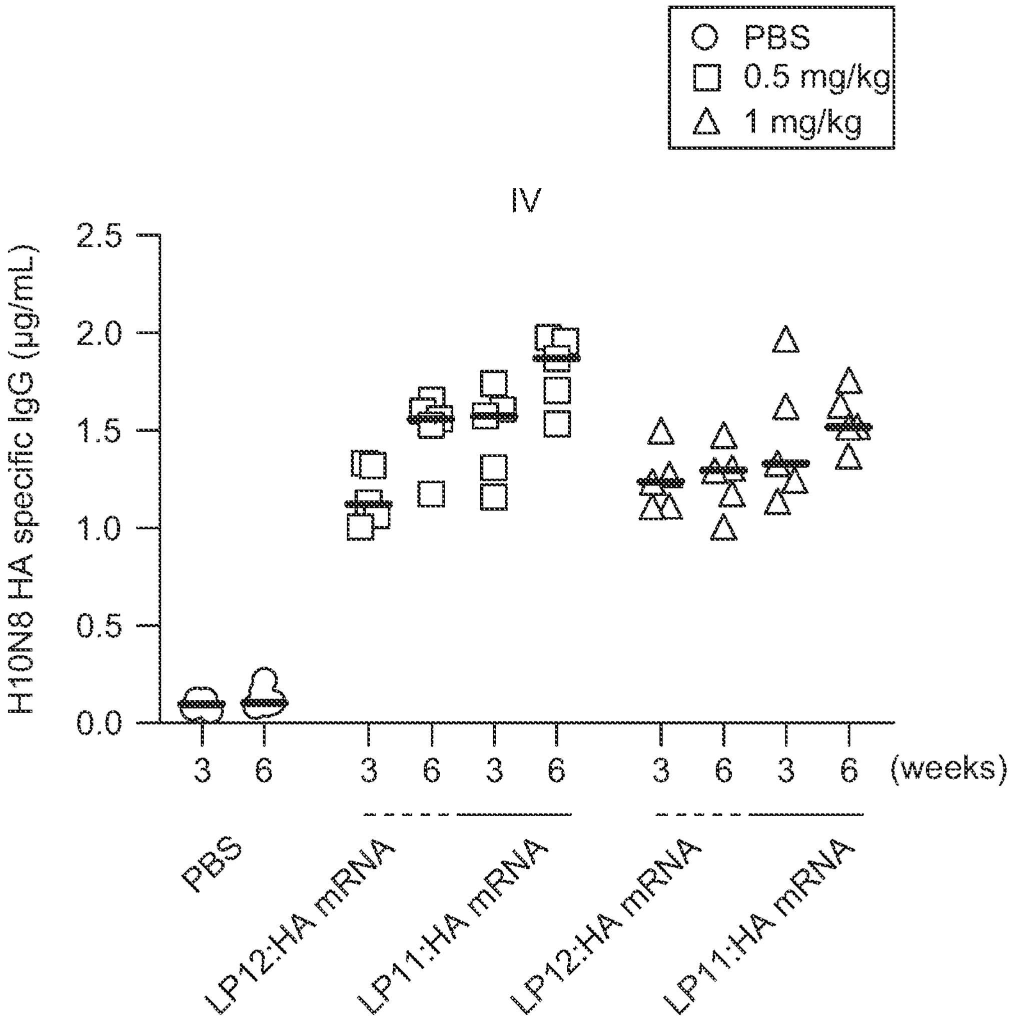

At week 3 after the prime injection and week 2 after booster injection (week 6 overall), serum IgG antibodies binding to the recombinant HA protein were detected in the mouse sera by enzyme-linked immunosorbent assay (ELISA). The HA-specific IgG responses following administration of the compositions are shown in FIG. 14A for IM administration and FIG. 14B for IV administration. The HA-specific IgG results are shown for the week 3 and week 6 sera samples from each mouse for each composition administered.

Figure 15A:
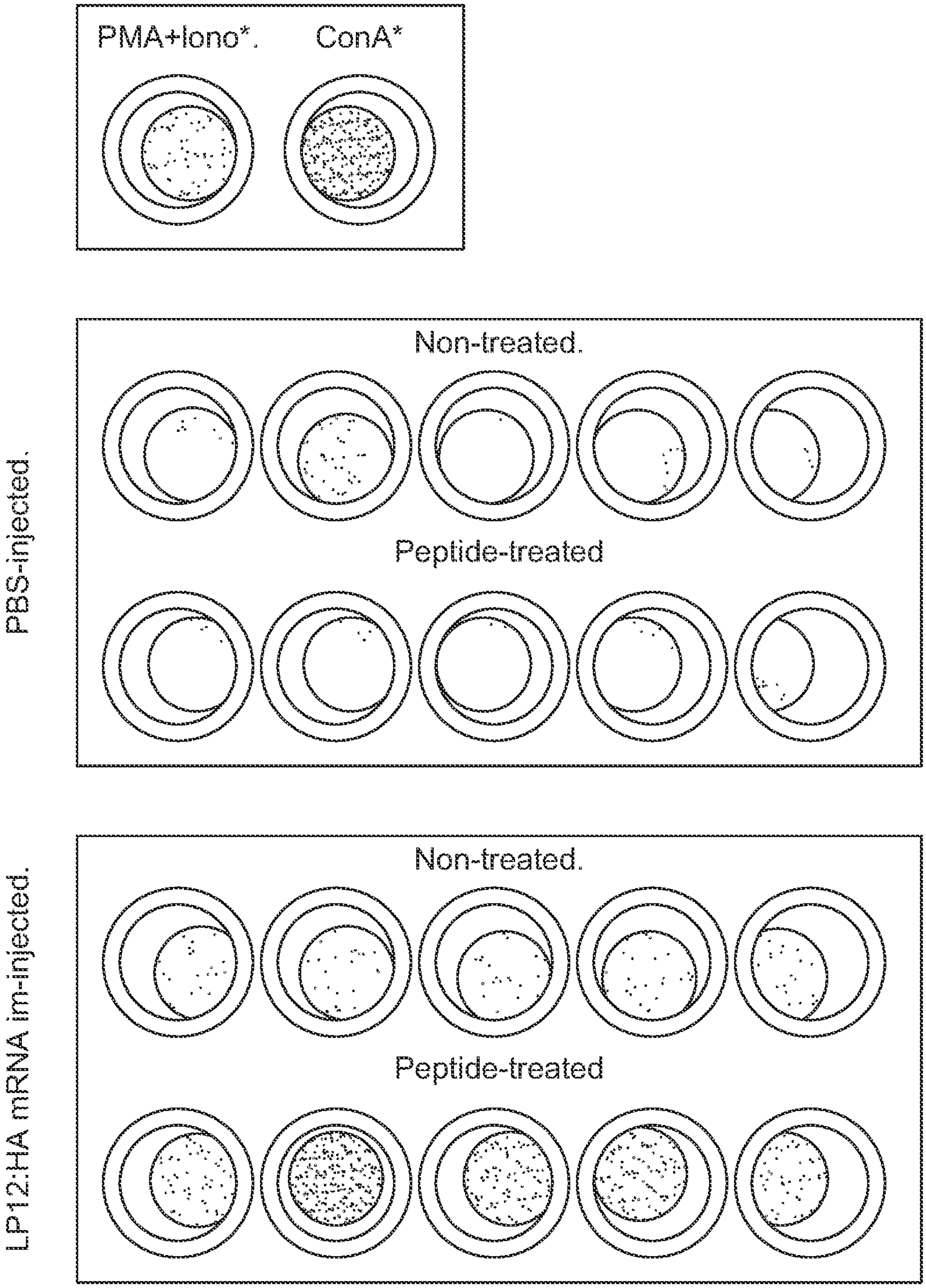
FIGS. 15A-15C are data showing the HA antigen-specific cellular immune response.
Figure 15B:
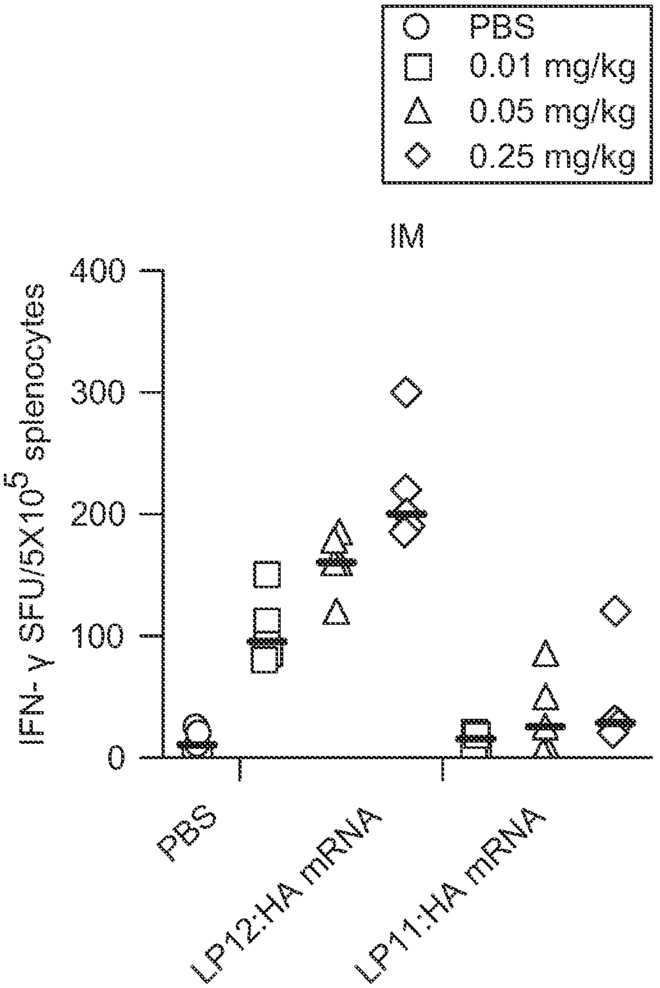
Figure 15C:
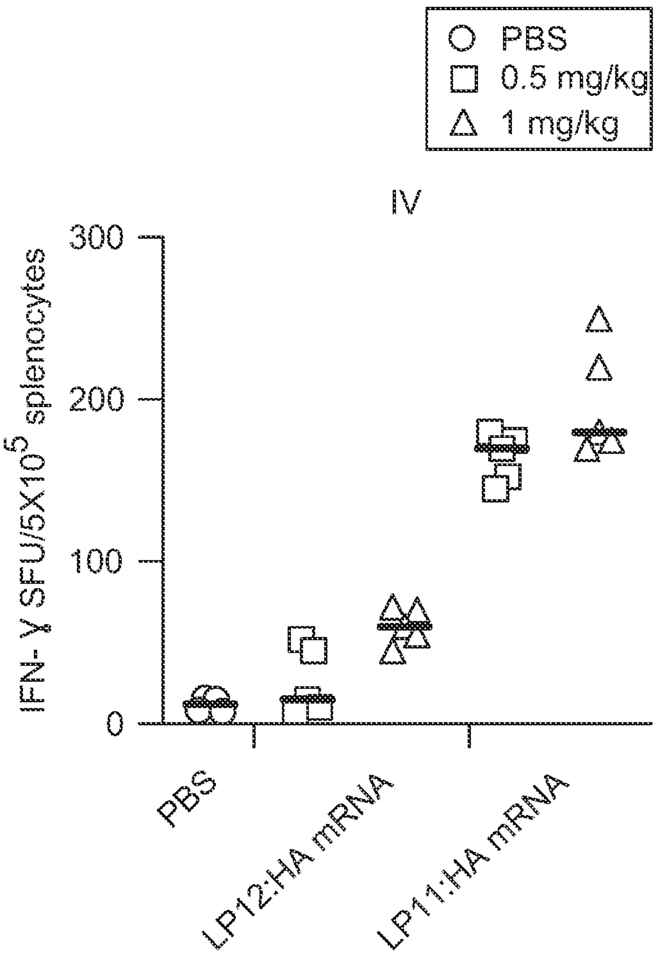

To assess HA antigen-specific cellular responses by interferon-γ (IFN-γ), splenocytes were isolated from the spleens at the end of prime-boost immunization schedule (week 6). HA-specific peptide stimulation was used for T cell activation in in vitro culture and released IFN-γ was detected by enzyme-linked immunosorbent spot (ELISPOT) assay. Exemplary results are shown in FIGS. 15A-15C.

Delivery of HA mRNA using both the LP11 and LP12 formulations resulted in antigen-specific humoral and cellular immune responses for all doses exemplified, even at the lowest dose tested.

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All references, e.g., U.S. patents, U.S. patent application publications, PCT patent applications designating the U.S., published foreign patents and patent applications cited herein are incorporated herein by reference in their entireties. GenBank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

While this invention has been particularly shown and described with references to preferred embodiments thereof, it will be understood by those skilled in the art that various changes in form and details may be made therein without departing from the scope of the invention encompassed by the appended claims.

SEQUENCE LISTING

```
Sequence total quantity: 38
SEQ ID NO: 1            moltype = AA  length = 8
FEATURE                 Location/Qualifiers
source                  1..8
                        mol_type = protein
                        organism = synthetic construct
SEQUENCE: 1
LLELLESL                                                            8

SEQ ID NO: 2            moltype = AA  length = 9
FEATURE                 Location/Qualifiers
```

-continued

```
source                1..9
                      mol_type = protein
                      organism = synthetic construct
SEQUENCE: 2
ALLELLESL                                                 9

SEQ ID NO: 3          moltype = AA  length = 9
FEATURE               Location/Qualifiers
source                1..9
                      mol_type = protein
                      organism = synthetic construct
SEQUENCE: 3
ELLELLESL                                                 9

SEQ ID NO: 4          moltype = AA  length = 9
FEATURE               Location/Qualifiers
source                1..9
                      mol_type = protein
                      organism = synthetic construct
SEQUENCE: 4
LLELLESLW                                                 9

SEQ ID NO: 5          moltype = AA  length = 9
FEATURE               Location/Qualifiers
source                1..9
                      mol_type = protein
                      organism = synthetic construct
SEQUENCE: 5
LLELLESLY                                                 9

SEQ ID NO: 6          moltype = AA  length = 20
FEATURE               Location/Qualifiers
source                1..20
                      mol_type = protein
                      organism = synthetic construct
SEQUENCE: 6
GLFEALLELL ESLWELLLEA                                     20

SEQ ID NO: 7          moltype = AA  length = 20
FEATURE               Location/Qualifiers
source                1..20
                      mol_type = protein
                      organism = synthetic construct
SEQUENCE: 7
GLFEALLELL ESLYELLLEA                                     20

SEQ ID NO: 8          moltype = AA  length = 23
FEATURE               Location/Qualifiers
source                1..23
                      mol_type = protein
                      organism = synthetic construct
SEQUENCE: 8
GLFEALLELL ESLWELLLEA WYG                                 23

SEQ ID NO: 9          moltype = AA  length = 22
FEATURE               Location/Qualifiers
source                1..22
                      mol_type = protein
                      organism = synthetic construct
SEQUENCE: 9
GLFEALLELL ESLWELLLEA KK                                  22

SEQ ID NO: 10         moltype = AA  length = 24
FEATURE               Location/Qualifiers
source                1..24
                      mol_type = protein
                      organism = synthetic construct
SEQUENCE: 10
GLFEALLELL ESLWELLLEA KKKK                                24

SEQ ID NO: 11         moltype = AA  length = 26
FEATURE               Location/Qualifiers
source                1..26
                      mol_type = protein
                      organism = synthetic construct
SEQUENCE: 11
GLFEALLELL ESLWELLLEA KKKKKK                              26

SEQ ID NO: 12         moltype = AA  length = 28
```

-continued

```
FEATURE                 Location/Qualifiers
source                  1..28
                        mol_type = protein
                        organism = synthetic construct
SEQUENCE: 12
GLFEALLELL ESLWELLLEA KKKKKKKK                                              28

SEQ ID NO: 13           moltype = AA  length = 22
FEATURE                 Location/Qualifiers
source                  1..22
                        mol_type = protein
                        organism = synthetic construct
SEQUENCE: 13
GLFEALLELL ESLWELLLEA EE                                                    22

SEQ ID NO: 14           moltype = AA  length = 24
FEATURE                 Location/Qualifiers
source                  1..24
                        mol_type = protein
                        organism = synthetic construct
SEQUENCE: 14
GLFEALLELL ESLWELLLEA EEEE                                                  24

SEQ ID NO: 15           moltype = AA  length = 26
FEATURE                 Location/Qualifiers
source                  1..26
                        mol_type = protein
                        organism = synthetic construct
SEQUENCE: 15
GLFEALLELL ESLWELLLEA EEEEEE                                                26

SEQ ID NO: 16           moltype = AA  length = 28
FEATURE                 Location/Qualifiers
source                  1..28
                        mol_type = protein
                        organism = synthetic construct
SEQUENCE: 16
GLFEALLELL ESLWELLLEA EEEEEEEE                                              28

SEQ ID NO: 17           moltype = AA  length = 22
FEATURE                 Location/Qualifiers
source                  1..22
                        mol_type = protein
                        organism = synthetic construct
SEQUENCE: 17
GLFEALLELL ESLWELLLEA RR                                                    22

SEQ ID NO: 18           moltype = AA  length = 24
FEATURE                 Location/Qualifiers
source                  1..24
                        mol_type = protein
                        organism = synthetic construct
SEQUENCE: 18
GLFEALLELL ESLWELLLEA RRRR                                                  24

SEQ ID NO: 19           moltype = AA  length = 26
FEATURE                 Location/Qualifiers
source                  1..26
                        mol_type = protein
                        organism = synthetic construct
SEQUENCE: 19
GLFEALLELL ESLWELLLEA RRRRRR                                                26

SEQ ID NO: 20           moltype = AA  length = 28
FEATURE                 Location/Qualifiers
source                  1..28
                        mol_type = protein
                        organism = synthetic construct
SEQUENCE: 20
GLFEALLELL ESLWELLLEA RRRRRRRR                                              28

SEQ ID NO: 21           moltype = AA  length = 18
FEATURE                 Location/Qualifiers
source                  1..18
                        mol_type = protein
                        organism = synthetic construct
SEQUENCE: 21
GLFEALLELL ESLWELLL                                                         18
```

-continued

```
SEQ ID NO: 22          moltype = AA  length = 20
FEATURE                Location/Qualifiers
source                 1..20
                       mol_type = protein
                       organism = synthetic construct
SEQUENCE: 22
GLLEELLELL EELWEELLEG                                            20

SEQ ID NO: 23          moltype = AA  length = 40
FEATURE                Location/Qualifiers
source                 1..40
                       mol_type = protein
                       organism = synthetic construct
SEQUENCE: 23
GLFEALLELL ESLWELLLEA GSGSGSGSRR RRRRRRRRRR                      40

SEQ ID NO: 24          moltype = AA  length = 44
FEATURE                Location/Qualifiers
source                 1..44
                       mol_type = protein
                       organism = synthetic construct
SEQUENCE: 24
GLFEALLELL ESLWELLLEA GSSSGSSSGS SSRRRRRRRR RRRR                 44

SEQ ID NO: 25          moltype = AA  length = 7
FEATURE                Location/Qualifiers
source                 1..7
                       mol_type = protein
                       organism = synthetic construct
SEQUENCE: 25
PSYYRYD                                                          7

SEQ ID NO: 26          moltype = AA  length = 7
FEATURE                Location/Qualifiers
source                 1..7
                       mol_type = protein
                       organism = synthetic construct
SEQUENCE: 26
PSYYRGD                                                          7

SEQ ID NO: 27          moltype = AA  length = 33
FEATURE                Location/Qualifiers
source                 1..33
                       mol_type = protein
                       organism = synthetic construct
SEQUENCE: 27
AARSPSYYRG DYGPYYAMDY DRRRRRRRRR RRR                             33

SEQ ID NO: 28          moltype = AA  length = 21
FEATURE                Location/Qualifiers
source                 1..21
                       mol_type = protein
                       organism = synthetic construct
SEQUENCE: 28
AARSPSYYRG DYGPYYAMDY D                                          21

SEQ ID NO: 29          moltype = AA  length = 33
FEATURE                Location/Qualifiers
source                 1..33
                       mol_type = protein
                       organism = synthetic construct
SEQUENCE: 29
AARSPSYYRG DAGPYYAMDY DRRRRRRRRR RRR                             33

SEQ ID NO: 30          moltype = AA  length = 21
FEATURE                Location/Qualifiers
source                 1..21
                       mol_type = protein
                       organism = synthetic construct
SEQUENCE: 30
AARSPSYYRG DAGPYYAMDY D                                          21

SEQ ID NO: 31          moltype = AA  length = 33
FEATURE                Location/Qualifiers
source                 1..33
                       mol_type = protein
                       organism = synthetic construct
SEQUENCE: 31
AARSPSYYRY DYGPYYAMDY DRRRRRRRRR RRR                             33
```

-continued

```
SEQ ID NO: 32          moltype = AA  length = 22
FEATURE                Location/Qualifiers
source                 1..22
                       mol_type = protein
                       organism = synthetic construct
SEQUENCE: 32
AARSPSYYRY DYGPYYAMDY DR                                   22

SEQ ID NO: 33          moltype = AA  length = 39
FEATURE                Location/Qualifiers
source                 1..39
                       mol_type = protein
                       organism = synthetic construct
SEQUENCE: 33
PSYYRGDGAP SYYRGDGAPS YYRGDGARRR RRRRRRRRR                 39

SEQ ID NO: 34          moltype = AA  length = 27
FEATURE                Location/Qualifiers
source                 1..27
                       mol_type = protein
                       organism = synthetic construct
SEQUENCE: 34
PSYYRGDGAP SYYRGDGAPS YYRGDGA                              27

SEQ ID NO: 35          moltype = AA  length = 39
FEATURE                Location/Qualifiers
source                 1..39
                       mol_type = protein
                       organism = synthetic construct
SEQUENCE: 35
PSYYRYDYGP SYYRYDYGPS YYRYDYGRRR RRRRRRRRR                 39

SEQ ID NO: 36          moltype = AA  length = 27
FEATURE                Location/Qualifiers
source                 1..27
                       mol_type = protein
                       organism = synthetic construct
SEQUENCE: 36
PSYYRYDYGP SYYRYDYGPS YYRYDYG                              27

SEQ ID NO: 37          moltype = AA  length = 17
FEATURE                Location/Qualifiers
source                 1..17
                       mol_type = protein
                       organism = synthetic construct
SEQUENCE: 37
FTLTGLLGTL VTMGLLT                                         17

SEQ ID NO: 38          moltype = AA  length = 7
FEATURE                Location/Qualifiers
source                 1..7
                       mol_type = protein
                       organism = synthetic construct
SEQUENCE: 38
APYKAWK                                                    7
```

What is claimed:

1. A method for delivering a payload to dendritic cells in the spleen of a subject, comprising:

(a) providing a lipid complex comprising:

at least one ionizable lipid, at least one peptide, wherein the peptide consists of SEQ ID NO: 6; and at least one payload molecule; and (b) administering the lipid complex to a subject.

2. The method of claim 1, wherein the lipid complex further comprises at least one neutral lipid.

3. The method of claim 1, wherein the lipid complex further comprises a second peptide which comprises at least one of SEQ ID NO: 25 and/or SEQ ID NO: 26.

4. The method of claim 1, wherein said peptide that consists of SEQ ID NO: 6 is at a concentration is at a concentration from about 0.001 to about 0.5 mg/mL, or from about 0.05 mg/mL to about 0.5 mg/mL.

5. The method of claim 1, wherein the payload molecule is a nucleic acid.

6. The method of claim 5, wherein the at least one ionizable lipid comprises a charge (N), the nucleic acid comprises a charge (P), and the lipid complex comprises an N/P ratio from 0.01 to 0.2, or from 0.05 to 0.5, or from 0.1 to 1.0, or from 0.5 to 2.0, or from 1.0 to 5.0.

7. The method of claim 1, wherein the payload comprises an RNA molecule.

8. The method of claim 1, wherein the lipid complex comprises a lipid nanoparticle population.

9. The method of claim 1, wherein the lipid complex comprises a liposome population.

10. The method of claim 1, wherein the administration comprises intravenous administration, intramuscular administration or subcutaneous administration.

* * * * *